United States Patent [19]

Aquino et al.

[11] Patent Number: 5,795,887

[45] Date of Patent: Aug. 18, 1998

[54] METHOD OF INDUCING CHOLECYSTOKININ AGONIST ACTIVITY USING 1,4- BENZODIAZEPINE COMPOUNDS

[75] Inventors: Christopher Joseph Aquino, Long Beach, Wash.; Milana Dezube, Chapel Hill, N.C.; Ronald George Sherrill, Cary, N.C.; Elizabeth Ellen Sugg, Durham, N.C.; Jerzy Ryszard Szewczyk, Chapel Hill, N.C.; Timothy Mark Willson, Durham, N.C.

[73] Assignee: Glaxo Wellcome Inc., Research Triangle Park, N.C.

[21] Appl. No.: 718,552

[22] PCT Filed: Apr. 13, 1995

[86] PCT No.: PCT/EP95/01335

§ 371 Date: Oct. 11, 1996

§ 102(e) Date: Oct. 11, 1996

[87] PCT Pub. No.: WO95/28399

PCT Pub. Date: Oct. 26, 1995

[30] Foreign Application Priority Data

| Apr. 15, 1994 | [GB] | United Kingdom | 9407468 |
| Apr. 15, 1994 | [GB] | United Kingdom | 9407499 |
| Oct. 14, 1994 | [GB] | United Kingdom | 9420699 |
| Oct. 14, 1994 | [GB] | United Kingdom | 9420702 |

[51] Int. Cl.⁶ ........................ A01N 43/62; C07D 243/24; C07D 243/12
[52] U.S. Cl. ........................ 514/221; 540/509; 540/517
[58] Field of Search ........................ 540/509, 517; 514/221

[56] References Cited

U.S. PATENT DOCUMENTS

| 5,301,591 | 4/1994 | Fletcher et al. | 540/509 |
| 5,302,591 | 4/1994 | US | 514/221 |
| 5,324,726 | 6/1994 | Bock et al. | 540/509 |
| 5,360,802 | 11/1994 | Chambers et al. | 514/221 |
| 5,646,140 | 7/1997 | US | 517/221 |

FOREIGN PATENT DOCUMENTS

| 0284256 | 9/1988 | European Pat. Off. | A61K 31/55 |
| A0284256 | 9/1988 | European Pat. Off. | |
| 434369 | 6/1991 | European Pat. Off. | |
| 0514133 | 5/1992 | European Pat. Off. | A61K 31/55 |
| A0514133 | 11/1992 | European Pat. Off. | |
| 0538099 | 4/1993 | European Pat. Off. | A61K 31/55 |
| 0538945 | 4/1993 | European Pat. Off. | A61K 31/55 |
| 538099 | 4/1993 | European Pat. Off. | |
| 538945 | 4/1993 | European Pat. Off. | |
| A0538099 | 4/1993 | European Pat. Off. | |
| A0538945 | 4/1993 | European Pat. Off. | |
| A9119733 | 12/1991 | WIPO | |
| A9308176 | 4/1993 | WIPO | |
| WO93/08176 | 4/1993 | WIPO | A61K 31/55 |
| A9317011 | 9/1993 | WIPO | |
| WO93/17011 | 9/1993 | WIPO | A61K 31/55 |
| A9413648 | 6/1994 | WIPO | |

*Primary Examiner*—Mukund J. Shah
*Assistant Examiner*—Tamthom T. Ngo
*Attorney, Agent, or Firm*—Robert H. Brink; Shah R. Makujina

[57] ABSTRACT

A method of inducing a Cholescystokinin-A receptor agonist response in a mammal by administering a compound of formula (I).

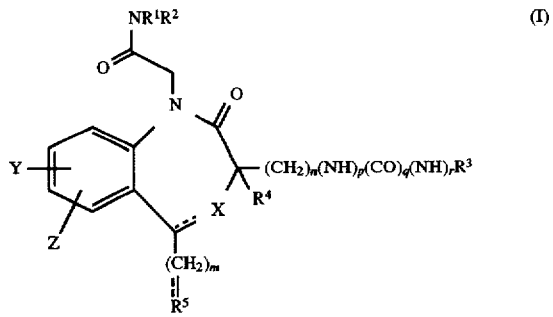

where $R^1$ is $C_1$–$C_6$alkyl, $C_{3-6}$cycloalkyl, phenyl, or substituted phenyl; $R^2$ is $C_{3-6}$alkyl, $C_{3-6}$cycloalkyl, $C_{3-6}$alkenyl, benzyl, phenyl$C_{1-3}$alkyl or substituted phenyl; or $NR^1R^2$ together form 1,2,3,4-tetrahydroquinoline or benzazepine mono-, di-, or trisubstituted independently with $C_{1-6}$alkyl, $C_{1-6}$alkoxy or halogen substituents; n is an integer selected from the grouping consisting of 0,1,2 or 3; p is the integer 0 or 1; q is the integer 0 or 1; r is the integer 0 or 1, provided that when q is 0 then r is 0; $R^3$, $R^4$, $R^5$ and $R^8$ are selected from a variety of substituents; X is nitrogen, nitroso or $R^8$; m is an integer selected from the group consisting of 0, 1, 2 or 3; Y and Z are hydrogen or halogen, novel intermediates, a pharmaceutical composition for treating obesity, gall bladder stasis, disorders of pancreatic secretion, methods for such treatment and processes for preparing compounds of formula (I).

12 Claims, No Drawings

METHOD OF INDUCING CHOLECYSTOKININ AGONIST ACTIVITY USING 1,4- BENZODIAZEPINE COMPOUNDS

This invention relates to 1,4 benzodiazepine having cholecystokinin (CCK) agonist activity. More particularly it relates to the use of 1,4-benzodiazepine which exhibit CCK-A agonist activity in the manufacture of a medicament for the treatment of conditions where a modulation of the effects of gastrin or CCK is of therapeutic benefit and to a method of inducing a CCK-A receptor agonist response in a mammal in need of treatment for a gastrointestinal or central nervous system related disease.

Cholecystokinin (CCK) is a peptide found in the gastrointestinal tract and the central nervous system, see A. J. Prange et al., *Ann. Reports Med. Chem.* 17, 31, 33 (1982), J. A. Williams, *Biomed Res.* 3, 107 (1982) and V. Mutt, *Gastrointestinal Hormones*, G. B. J. Green, Ed., Raven Press, New York, 169. CCK has been implicated inter alia as a physiological satiety hormone involved in appetite regulation, see Della-Ferra et al., *Science*, 206, 471 (1979), Saito et al., *Nature*, 289, 599, (1981), G. P. Smith, *Eating and Its Disorders*, A. J. Stunkard and E. Stellar, Eds, Raven Press, New York, 67 (1984), as a regulator of gallbladder contraction and pancreatic enzyme secretion, an inhibitor of gastric emptying, and as a neurotransmitter, see A. J. Prange, supra, J. A. Williams, *Biomed Res.*, 3,107 (1982), J. E. Morley, *Life Sci.* 30, 479, (1982). Gastrin is a peptide involved in gastric acid and pepsin secretion in the stomach, see L. Sandvik, et al, *American J. Physiology*, 260, G925 (1991), C. W. Lin, et al., *Amercan J Physiology*, 262, G1113, (1992). CCK and gastrin share structural homology in their C-terminal tetrapeptide: Trp-Met-Asp-Phe.

Two subtypes of CCK receptors have been identified, designated as CCK-A and CCK-B, and both have been found in the periphery and central nervous systems. It has recently been reported that CCK-B receptors are similar to the gastrin receptor, see Pisegna, J. R., de Weerth, A, Huppi, K, Wank, S. A., *Biochem. Biophys. Res. Commun.* 189, 296–303 (1992). CCK-A receptors are located predominantly in peripheral tissues including the pancreas, gallbladder, ileum, pyloric sphincter and vagal afferent nerve fibers; CCK-A receptors are found to a lesser extent in the brain, see T. H. Moran, et al., *Brain Res.*, 362, 175–179 (1986), D. R. Hill, et al, *Brain Res*, 4545,101, (1988), D. R. Hill, et al, *Neurosci Lett.*, 89, 133, (1988), R. W. Barret, et al., *Mol. Pharmacol*, 36, 285, (1989), D. R. Hill, et al., *J Neurosci*, 10, 1070 (1990), V. Dauge at al., *Pharmacol Biochem Behac.*, 33, 637, (1989), while CCK-B receptors are found predominantly in the brain, see V. J. Lotti and R. S. L Chang, *Proc. Natl. Acad. Sci. U.S.A.*, 83, 4923 (1986), J. N. Crawley, *Trends Pharm. Sci.*, 88, 232, (1991).

The literature in the CCK area contains extensive discussion surrounding CCK antagonist activity relating to the increase of food intake and treating oncologic disorders, in particular relating to 1,4- and 1,5-benzodiazepines, see B. E. Evans, *Drugs of the Future*, 14, 971 (1989), M. A. Silverman, et al., *Am. J. Gastroenterol*, 82, 703 (1987), EPO 0538 945, published Apr. 28, 1993, EPO 0 523 845. published Jan. 20, 1993, EPO 0284 256, published 28 Sep., 1988, and relating to the regulation of anxiety, arousal, neuroleptic agents, and opioid -induced analgesia, see Lotti, supra, Crawley, supra, Singh, L., et al, *Proc. Natl. Acad. Sci. U.S.A.*, 88, 1130 (1991).

On the other hand, CCK agonist activity has been linked to inhibition of food intake in animals and thus weight loss, see Della-Fera, et al, supra, K. E. Asin, et al, Intl. Conference on Obesity, abstract pp.40 (1990). It has been suggested that CCK acts in the periphery through vagal fibers and not directly on the brain to produce satiety, see Smith, G. P. and Cushin, B. J., *Neuroscience Abstr.*, 4, 180 (1978), Smith, G. P., Jerome, C., Cushin, B. J., Eterno, R., and Simansky, K. J., *Science*, 212, 687–689, (1981). Compounds having CCK agonist activity have been reported to include peptide analogues, see U.S. Pat. No. 4,490,364, PCT WO 91/19733, published 26 Dec. 1991, K. Shiosaki et al., *J. Med. Chem.*, 33, 2950 (1990).

However, to our knowledge 1,4-benzodiazepines have not been disclosed as having CCK-A agonist activity, nor has the —CH$_2$CON(isopropyl)(phenyl) substituent at the N-1 position of the 1,4-benzodiazepine molecule been specifically exemplified. Compounds of the present invention have been found to have CCK-A agonist activity, and therefore may be useful in part for inhibiting appetite, for inducing long-term weight loss in overweight patients and improving the cardiovascular and non-insulin dependent diabetes problems associated with these overweight conditions, and for treating obesity, gall bladder stasis and disorders of pancreatic secretion.

CCK has been shown to inhibit gastric emptying in humans and is thus useful for treatment of diabetes, particularly early noninsulin-dependent diabetes, through maintenance of the following glucose metabolic indicators at or near normal levels: blood glucose, C-peptide, insulin levels at fasting and during oral glucose tolerance tests, hemoglobin A1C, insulin resistance, GIP levels and CCK levels, see U.S. Pat. No. 5,187,154, which is incorporated herein by reference. The CCK-A agonist compounds of the present invention are therefore useful for treatment of diabetic humans through stabilization of these glucose metabolic indicators.

Thus the present invention provides a novel method of inducing a Cholescystokinin-A receptor agonist response in a mammal in need of treatment of a gastrointestinal or central nervous system related disease which comprises administering to such mammal an effective amount of a 1,4-benzodiazepine compound of the following formula (I):

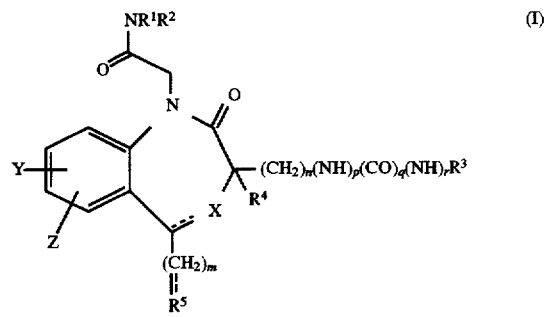

wherein:

R$^1$ is selected from the group consisting of C$_{1-6}$ alkyl, C$_{3-6}$cycloalkyl, phenyl, or phenyl mono-, di-, or trisubstituted independently with hydroxy, C$_{1-6}$alkyl, C$_{1-6}$alkyl substituted with 1–8 fluorine atoms, C$_{1-6}$alkoxy, carboxyC$_{1-6}$alkoxy, halo, amino, mono- or di(C$_{1-6}$alkyl)amino, —COO(C$_{1-6}$alkyl), C$_{1-6}$alkylthio, carboxymethylthio, trifluoromethylsulfonylamino, phenylC$_{1-6}$alkoxy, C$_{1-6}$alkylsulfonyl or C$_{1-6}$alkylsulfinyl substituents;

R$^2$ is selected from the group consisting of C$_{3-6}$ alkyl, C$_{3-6}$cycloalkyl, C$_{3-6}$alkenyl, benzyl, phenylC$_{1-3}$alkyl or phenyl mono-, di-, or trisubstituted independently in the ortho or para positions with hydroxy, $C_{1-6}$alkyl, $C_{1-6}$alkoxy, cyano, benzyloxy, pyrrolidino, morpholino, carboxy$C_{1-6}$alkoxy, halo, amino, mono- or di($C_{1-6}$alkyl)amino, —COO($C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl or $C_{1-6}$alkylsulfinyl substituents; or $NR^1R^2$ together form 1,2,3,4-tetrahydroquinoline or benzazepine mono-, di-, or trisubstituted independently with $C_{1-6}$alkyl, $C_{1-6}$alkoxy or halogen substituents;

n is an integer selected from the group consisting of 0, 1, 2, or 3;

p is the integer 0 or 1;

q is the integer 0 or 1;

r is the integer 0 or 1, provided that when q is 0 then r is 0;

$R^3$ is selected from the group consisting of hydrogen, $C_{1-6}$alkyl, $C_{1-6}$cycloalkyl, phenyl, phenyl mono-, di-, or trisubstituted independently with $C_{1-6}$alkyl, hydroxy, $C_{1-6}$alkoxy, halogen, amino, mono- or di($C_{1-6}$alkyl) amino, nitro, carboxy, —COO($C_{1-6}$alkyl), carboxy$C_{1-6}$alkoxy, carboxy$C_{1-6}$alkyl, carboxymethylthio, heteroaryl, mono- or di($C_{1-6}$alkyl)amino$C_{1-6}$alkyl, trifluoromethyl, trifluoromethoxy, $C_{1-6}$alkylthio, —$SO_v$($C_{1-6}$alkyl), —$SO_v$NH($C_{1-6}$cycloalkyl), —$SO_vCF_3$, —$SO_vC_6H_5$, —$(CH_2)_wNO_2$, —$(CH_2)_w$CN, —$(CH_2)_w$COOH, —$(CH_2)_w$COO($C_{1-6}$alkyl), —$(CH_2)_w$SCH$_3$, —$(CH_2)_w$SOCH$_3$, —$(CH_2)_w$SO$_2$CH$_3$, —$(CH_2)_w$CONH$_2$, —SCH$_2$COOH, —CONH(SO$_2$CH$_3$), —CONH(SO$_2$CF$_3$), —$(CH_2)_w$N($C_{1-6}$alkyl)$_2$, —$(CH_2)_w$NH(SO$_2$CF$_3$), —$(CH_2)_w$N(SO$_2$CF$_3$)($C_{1-6}$-alkyl), —$(CH_2)_w$SO$_2$NHCO($C_{1-6}$alkyl), —$(CH_2)_w$SO$_2$N($C_{1-6}$alkyl)CO($C_{1-6}$alkyl), —$(CH_2)_w$CONHSO$_2$($C_{1-6}$alkyl), —$(CH_2)_w$CON($C_{1-6}$alkyl)SO$_2$($C_{1-6}$alkyl), —$(CH_2)_w$NHR$^6$ or —$(CH_2)_w$OR$^7$ substituents, heteroaryl, substituted heteroaryl, napthyl, bicycloheteroaryl or substituted bicycloheteroaryl, provided when $R^3$ is oxadiazole then $R^4$ is not hydrogen, further provided when n is 1, p is 0, q is 0 and r is 0 then $R^3$ is not 2-indolyl, substituted 3-indolyl or substituted 1-isoindolyl, still further provided that when n is 0, p is 1, q is 1 and r is 0 then $R^3$ is not 2-indolyl and substituted indolyl is bound at the 2 position, even still further provided that when n is 1, p is 1, q is 1 and r is 0 then $R^3$ is not phenyl or 2-indolyl;

$R^6$ is hydrogen, $C_{1-6}$alkyl, —$SO_3H$, —$SO_2CH_3$, —$SO_2CF_3$, —$SO_2C_6H_5$, —$COO(C_4H_9)$ or —$COO(CH_2C_6H_5)$;

$R^7$ is hydrogen, $C_{1-6}$alkyl, $C_{3-6}$cycloalkyl, —$CH_2C_6H_5$, —$CH_2COOH$, —$CH_2CONH_2$, —$CH_2CONH(C_{1-6}$alkyl), —$CH_2CON(C_{1-6}$alkyl)$_2$ or

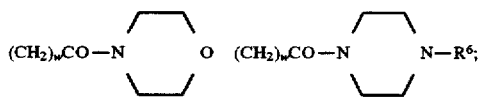

v is an integer selected from the group consisting of 0, 1 or 2;

w is an integer selected from the group consisting of 0, 1 or 2;

$R^4$ is selected from the group consisting of hydrogen, $C_{1-6}$alkyl, halogen, $C_{1-6}$alkoxy, $C_{1-6}$alkoxy$C_{1-3}$alkyl, carboxy$C_{1-3}$alkyl or $C_{1-6}$alkoxycarbonyl$C_{1-3}$alkyl;

X is nitrogen, nitroso, or NR8, provided that when X is nitrogen or nitroso then ———— is a double bond between X and the C-5 position of the diazepine ring, and is a single bond when X is $NR^8$;

$R^8$ is selected from the group consisting of hydrogen, $C_{1-6}$alkyl or $(CH_2)_kR^9$;

k is an integer selected from the group consisting of 0, 1, 2, 3 or 4;

$R^9$ is selected from the group consisting of amino, mono- or di($C_{1-6}$alkyl)amino, pyrrolidinyl, morpholinyl, piperidinyl, piperazinyl, phenyl, nitro, carboxyl, carboxamide, hydroxyl, heteroaryl, —COO($C_{1-6}$alkyl), —CONH($C_{1-6}$alkyl), —SO$_t$($C_{1-6}$alkyl), —SO$_t$NH($C_{1-6}$alkyl), —SO$_t$CF$_3$, —SO$_t$C$_6$H$_5$, —O($C_{1-6}$alkyl) or —CON($C_{1-6}$alkyl)$_2$;

t is an integer selected from the group consisting of 0, 1 or 2;

m is an integer selected from the group consisting of 0, 1, 2, or 3.

$R^5$ is selected from the group consisting of hydrogen, $C_1$-$C_6$ alkyl, $C_3$-$C_7$ cycloalkyl, oxygen, phenyl, phenyl mono or di-substituted with halogen substituents, heteroaryl, substituted heteroaryl or 5, 6 or 7 membered saturated heterocycle, provided that when $R^5$ is oxygen and m is 0 then ———— is a double bond between $R^5$ and the C-5 position of the diazepine ring, and is a single bond when $R^5$ is not oxygen; or $XR^5$ together form a heteraryl or substituted hetaryl where X is nitrogen, provided ———— is a double bond between R5 and the C-5 position of the diazepine ring and m is 0;

Y and Z are independently hydrogen or halogen;

5, 6 or 7 membered saturated heterocycle in more detail is a 5, 6 or 7 membered saturated heterocycle interrupted by 1, 2, 3, or 4 N or O heteroatoms, with the proviso that any two O atoms are not bonded to each other;

heteroaryl in more detail includes a 5 or 6 membered aromatic ring optionally interrupted by 1, 2, 3 or 4 N, S, or O heteroatoms, with the proviso that any two O or S atoms are not bonded to each other;

substituted heteroaryl in more detail includes heteroaryl mono-, di-, or trisubstituted independently with hydroxy, $C_{1-6}$alkyl, $C_{1-6}$alkoxy, carboxy$C_{1-6}$alkoxy, halogen, amino, mono- or di($C_{1-6}$alkyl)amino, nitro, carboxy, —COO($C_{1-6}$alkyl), —CONH($C_{1-6}$alkyl), $C_{1-6}$alkylthio, carbosamide, carboxymethylthio, phenyl, benzyl, benzoxy, cyano, trifluoromethyl, —CONH($C_{1-6}$alkyl), —CONHC$_{1-6}$alkyl)$_2$, —SO$_z$($C_{1-6}$alkyl), —SO$_z$NH($C_{1-6}$alkyl), —SO$_z$CF$_3$ or —SO$_z$C$_6$H$_5$, pyrrolidinyl, morpholinyl, piperidinyl, piperazinyl, trifluoromethylsulfonylamino, phenyl$C_{1-6}$alkoxy, $C_{1-6}$alkylsulfonyl, $C_{1-6}$alkylsulfinyl, phenyl, carboxamide, or heteroaryl substituents;

z is an integer selected from the group consisting of 0, 1 or 2;

bicycloheteroaryl in more detail is a 9 or 10 membered bicyclo aromatic ring interrupted by 1, 2, 3 or 4 N, O or S heteroatoms, with the proviso that any two O or S heteroatoms are not bonded to each other, with the further proviso that bicycloheteroaryl is not quinoline;

substituted bicycloheteroaryl in more detail includes bicyclo heteroaryl mono-, di-, or trisubstituted independently with hydroxy, ($C_{1-6}$alkyl), $C_{1-6}$alkoxy, cyano, carboxy($C_{1-6}$alkyl), phenyl, heteroaryl, phenyl($C_{1-6}$alkyl) or ($C_{1-6}$alkyl)COO($C_{1-6}$alkyl);

or a pharmaceutically acceptable acid-addition or organic base-addition salt thereof.

The present invention also provides for the use of a compound of formula (1) in the manufacture of a medicament for the treatment of conditions where modulation of the effects of gastrin or CCK is therapeutic benefit.

One aspect of the invention includes using compounds of formula (Ia):

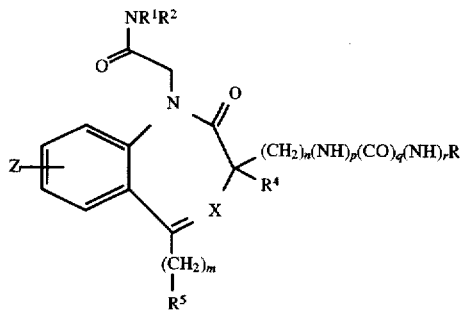

wherein:

- $R^1$ is selected from the group consisting of $C_1$–$C_6$ alkyl, $C_3$–$C_6$cycloalkyl, phenyl, or phenyl mono-, di-, or trisubstituted independently with hydroxy, $C_{1-6}$alkyl, $C_{1-6}$alkyl substituted with 1–8 fluorine atoms, $C_{1-6}$alkoxy, carboxy$C_{1-6}$alkoxy, fluoro, amino, mono- or di($C_{1-6}$alkyl)amino, $-COO(C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl or $C_{1-6}$alklsulfinyl substituents;

- $R^2$ is selected from the group consisting of $C_3$–$C_6$ alkyl, $C_3$–$C_6$cycloalkyl, $C_3$–$C_6$alkenyl, benzyl, phenyl$C_1$–$C_3$alkyl or phenyl mono-, di-, or trisubstituted independently in the ortho or para positions with hydroxy, $C_{1-6}$alkyl, $C_{1-6}$alkoxy, cyano, benzyloxy, pyrrolidino, morpholino, carboxy$C_{1-6}$alkoxy, chloro, amino, mono- or di($C_{1-6}$alkyl)amino, $-COO(C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl or $C_{1-6}$-alkylsulfinyl substituents; or

- $NR^1R^2$ together form 1,2,3,4-tetrahydroquinoline or benzazepine mono-, di-, or trisubstituted independently with $C_{1-6}$alkyl, $C_{1-6}$alkoxy or halogen substituents;

- n is an integer selected from the group consisting of 0, 1, 2, or 3;

- p is the integer 0 or 1;

- q is the integer 0 or 1;

- r is the integer 0 or 1, provided that when q is 0 then r is 0;

- $R^3$ is selected from the group consisting of hydrogen, $C_{1-6}$alkyl, $C_{1-6}$cycloalkyl, phenyl, phenyl mono-, di-, or trisubstituted independently with $C_{1-6}$alkyl, hydroxy, $C_{1-6}$alkoxy, halogen, amino, mono- or di($C_{1-6}$alkyl)amino, nitro, carboxy, $-COO(C_{1-6}$alkyl), carboxy$C_{1-6}$alkoxy, carboxy$C_{1-6}$alkyl, carboxymethylthio, heteroaryl, mono- or di($C_{1-6}$alkyl)aminoalkyl, or trifluoromethyl, trifluoromethoxy, $C_{1-6}$alkylthio, $-SO_v$($C_{1-6}$alkyl), $-SO_vNH(C_{1-6}$alkyl), $-SO_vCF_3$ or $-SO_vC_6H_5$, $-(CH_2)_vNO_2$, $-(CH_2)_vCN$, $-(CH_2)_vCOOH$, $-(CH_2)_vCOO(C_{1-6}$alkyl), $-(CH_2)_vSCH_3$, $-(CH_2)_vSOCH_3$, $-(CH_2)_vSO_2CH_3$, $-(CH_2)_vCONH_2$, $-SCH_2COOH$, $-CONH(SO_2CH_3)$, $-CONH(SO_2CF_3)$, $-(CH_2)_vN(C_{1-6}$alkyl)$_2$, $-(CH_2)_vNH(SO_2CF_3)$, $-(CH_2)_vN(SO_2CF_3)(C_{1-6}$alkyl), $-(CH_2)_vSO_2NHCO(C_{1-6}$alkyl), $-(CH_2)_vSO_2N(C_{1-6}$alkyl)$CO(C_{1-6}$alkyl), $-(CH_2)_vCONHSO_2(C_{1-6}$alkyl), $-(CH_2)_vCON(C_{1-6}$alkyl)$SO_2(C_{1-6}$alkyl), $-(CH_2)_vNHR^6$ or $-(CH_2)_vOR^7$ substituents, heteroaryl, heteroaryl substituted with halogen, $C_{1-6}$alkyl, hydroxy, nitro, cyano, carboxy, $C_{1-6}$alkoxy, benzoxy, $-COO(C_{1-6}$alkyl), amino, mono- or di($C_{1-6}$alkyl)amino, phenyl or benzyl substituents, napthyl, bicycloheteroaryl or bicycloheteroaryl N-substituted independently with hydroxy, carboxyalkyl, phenyl, heteroaryl, $C_{1-6}$alkoxy or cyano substituents;

- $R^6$ is hydrogen, $C_{1-6}$alkyl, $-SO_3H$, $-SO_2CH_3$, $-SO_2CF_3$, $-SO_2C_6H_5$, $-COO(C_4H_9)$ or $-COO(CH_2C_6H_5)$;

- $R^7$ is hydrogen, $C_{1-6}$alkyl, $C_{3-6}$cycloalkyl, $-CH_2C_6H_5$, $-CH_2COOH$, $-CH_2CONH_2$, $-CH_2CONH(C_{1-6}$alkyl), $-CH_2CON(C_{1-6}$alkyl)$_2$ or

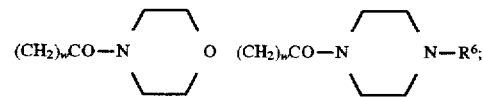

- v is an integer selected from the group consisting of 0, 1 or 2;

- w is an integer selected from the group consisting of 0, 1 or 2;

- $R^4$ is selected from the group consisting of hydrogen, halogen, $C_{1-6}$alkyl, $C_{1-6}$alkoxy, $C_{1-6}$alkoxy$C_{1-3}$alkyl, carboxy$C_{1-3}$alkyl or $C_{1-6}$alkoxycarbonyl$C_{1-3}$alkyl;

- X is nitrogen or nitroso, provided that when $R^2$ is methoxyphenyl, p is 1.

- q is 1 and r is 0 then X is nitroso;

- m is an integer selected from the group consisting of 0, 1, 2, or 3;

- $R^5$ is selected from the group consisting of hydrogen, $C_1$–$C_6$ alkyl, $C_{5-7}$ cycloalkyl, phenyl or phenyl mono- or di-ortho-substituted independently with halogen substituents, or a heteroaryl selected from the group consisting of pyridyl, pyrimidinyl, pyridazinyl, pyrazinyl, furanyl, thiophenyl, pyrrolyl, oxazolyl, thiazolyl, imidazolyl, pyrazolyl, isoxazolyl, isothiazolyl, oxadiazolyl, thiazolyl, thiadiazolyl, pyrrolidinyl, piperidinyl, morpholinyl or thiomorpholinyl, where such heteroaryl may be mono- or di- ortho-substituted independently with halogen, $C_{1-6}$alkyl, nitro, carboxyl, $C_{1-6}$alkoxycarbonyl, $C_{1-6}$alkoxy, $C_{1-6}$alkylthio, amino or mono- or di($C_{1-6}$alkyl)amino substituents;

- Z is hydrogen or halogen;

- heteroaryl in more detail includes a 5 or 6 membered aromatic ring optionally interrupted by 1, 2, 3 or 4 N, S, or O heteroatoms, with the proviso that any two O or S atoms are not bonded to each other;

- substituted heteroaryl in more detail includes heteroaryl mono-, di-, or trisubstituted independently with $C_{1-6}$alkyl or phenyl;

or a pharmaceutically acceptable acid-addition or base-addition salt thereof.

The method in particular includes using the following groups of formula (Ia):

1. $R^1$ is conveniently $C_{3-6}$alkyl e.g. propyl, isopropyl, t-butyl or $C_{3-6}$cycloalkyl e.g. cyclopropyl or cyclohexyl. More particularly $R^1$ is isopropyl.

2. $R^2$ is conveniently a phenyl group optionally substituted by a group selected from methoxy, fluoro, dimethylamino, methyl, trifluoromethyl, trifluoromethoxy, pyrrolidino or morphblino and preferably the substituent is in the para position. More conveniently $R^2$ is phenyl optionally substituted by methoxy or dimethylamino. Preferably $R^2$ is phenyl or 4-methoxyphenyl.
3. The group Z is conveniently hydrogen or fluorine and more particularly hydrogen.
4. $R^4$ is conveniently hydrogen.
5. The integer m is conveniently zero and $R^5$ is phenyl, $C_{1-4}$ alkyl e.g. methyl, $C_{5-7}$ cycloalkyl e.g. cyclohexyl or pyridyl e.g. 3-pyridyl
6. X is conveniently N or nitroso.
7. When n is zero, p and q are conveniently 1 and r is zero or 1. Within this group when r is 1 $R^3$ is conveniently optionally substituted phenyl (e.g. phenyl optionally by tetrazolyl or carboxy) or 7-indazolyl. When r is zero then $R^3$ is conveniently optionally substituted phenyl (e.g. 2-amino-4-chlorophenyl) or indolyl e.g. 2-indolyl optionally substituted on nitrogen by carboxyalkyl e.g. carboxymethyl.
8. When n is 1 q is conveniently zero. Within this group q and r are conveniently both either zero or 1. When q and r are zero $R^3$ is conveniently indolyl e.g. 3-indolyl. When q and r are both 1 $R^3$ is conveniently optionally substituted phenyl e.g. 3-phenyl or 3-carboxyphenyl.
9. $R^1$ is isopropyl, $R^2$ is phenyl or 4-methoxyphenyl, Z is hydrogen, m is zero, $R^5$ is phenyl, methyl, cyclohexyl or 3-pyridyl, $R^4$ is hydrogen, X is N or nitroso. Within this class preferred groups include those where n is zero and p, q and r are 1 and $R^3$ is phenyl optionally substituted by carboxy, or n and r are zero, p and q are 1 and $R^3$ is 2-indolyl or n is 1 p, q and r are zero and $R^3$ is 3-indolyl.

10.
   $R^1$ is phenyl;
   $R^2$ is isopropyl.

11.
   $R^1$ is selected from the group consisting of phenyl, 4-methoxyphenyl or 4-dimethylaminophenyl;
   $R^2$ is selected from the group consisting of propyl, isopropyl, butyl or cyclohexyl.

12.
   n is 0 or 1;
   p is 1;
   q is 1;
   r is 0;
   $R^3$ is selected from the group consisting of hydrogen, hydroxy, carboxy, phenyl, substituted phenyl, heteroaryl, indolyl, N-(carboxymethyl)indolyl, N-($C_{1-6}$alkylcarbonylmethyl)indolyl or phenyl$C_{1-6}$alkoxy.

13.
   n is 0 or 1;
   p is 1;
   q is 1;
   r is 1;
   $R^3$ is selected from the group consisting of phenyl, substituted phenyl or
   7-indazolyl.

14.
   $R^4$ is hydrogen.

15.
   $R^4$ is selected from the group consisting of hydrogen, $C_{1-6}$alkyl, fluoro or chloro.

16.
   X is nitroso.

R is $C_{5-7}$ cycloalkyl.

17.
   $R^1$ is phenyl;
   $R^2$ is $C_{3-6}$ alkyl.
   n is 0 or 1;
   p is 1;
   q is 1;
   r is 0 or 1;
   $R^3$ is selected from the group consisting of hydrogen, hydroxy, carboxy, phenyl, substituted phenyl, indolyl, N-(carboxymethyl)indolyl, N-($C_{1-6}$alkylcarbonylmethyl)indolyl, indazole or phenyl$C_{1-6}$alkoxy;
   $R^4$ is selected from the group consisting of hydrogen, $C_{1-6}$alkyl, chloro or fluoro;
   m is 0 or 1;
   $R^5$ is selected from the group consisting of $C_1$–$C_6$ alkyl, phenyl, or a saturated 5, 6, or 7 membered ring optionally interrupted by 1,2, 3, or 4 N, S, or O heteroatoms, with the proviso that any two O or S atoms are not bonded to each other;
   Z is hydrogen.

18.
   $R^1$ is isopropyl;
   $R^2$ is phenyl;
   n is 0;
   p is 1;
   q is 1;
   r is 1;
   $R^3$ is carboxyphenyl;
   $R^4$ is hydrogen;
   m is 0;
   $R^5$ is phenyl;
   Z is hydrogen.

19.
   $R^1$ is isopropyl;
   $R^2$ is methoxyphenyl;
   n is 0;
   p is 1;
   q is 1;
   r is 1;
   $R^3$ is carboxyphenyl;
   $R^4$ is hydrogen;
   m is 0;
   $R^5$ is phenyl;
   Z is hydrogen.

20.
   $R^1$ is isopropyl;
   $R^2$ is methoxyphenyl;
   n is 0;
   p is 1;
   q is 1;
   r is 1;
   $R^3$ is phenyl;
   $R^4$ is hydrogen;
   m is 0;
   $R^5$ is cyclohexyl;
   Z is hydrogen.

21.
- $R^1$ is isopropyl;
- $R^2$ is p-methoxyphenyl;
- n is 0;
- p is 1;
- q is 1;
- r is 1;
- $R^3$ is phenyl;
- $R^4$ is hydrogen;
- m is 0;
- $R^5$ is methyl;
- Y and Z are hydrogen.

22.
- X is nitroso
- $R^5$ is cyclohexyl.

The method in particular in addition to inducing a Cholescystokinin-A receptor agonist response by administering the mammal an effective amount of a 1,4-benzodiazepine compound of the formula (I) may also include inducing a Cholescystokinin-B receptor antagonist response in a mammal.

The invention further comprises 1,4-benzodiazepine compounds of formula (Ia) wherein:

$R^1$ is selected from the group consisting of hydrogen, $C_1$–$C_6$ alkyl, $C_3$–$C_6$cycloalkyl, phenyl, or phenyl mono-, di-, or trisubstituted independently with hydroxy, $C_{1-6}$alkyl, $C_{1-6}$alkoxy, carboxy$C_{1-6}$alkoxy, halogen, amino, mono- or di($C_{1-6}$alkyl)amino, nitro, carboxy, —COO($C_{1-6}$alkyl), $C_{1-6}$alkylthio, carboxymethylthio, trifluoromethyl, trifluoromethylsulfonylamino, phenyl$C_{1-6}$alkoxy or heteroaryl substituents;

$R^2$ is selected from the group consisting of hydrogen, $C_1$–$C_6$ alkyl, phenyl, phenyl$C_1$–$C_3$alkyl or phenyl mono-, di-, or trisubstituted independently with hydroxy, $C_{1-6}$alkyl, $C_{1-6}$alkoxy, carboxy$C_{1-6}$alkoxy, halogen, amino, mono- or di($C_{1-6}$alkyl)amino, nitro, carboxy, —COO($C_{1-6}$alkyl), $C_{1-6}$alkylthio, carboxymethylthio, trifluoromethyl, trifluoromethylsulfonylamino, phenyl$C_{1-6}$alkoxy or heteroaryl substituents; or $NR^1R^2$ together form 1,2,3,4-tetrahydroquinoline mono-, di-, or trisubstituted with halogen substituents;

n is an integer selected from the group consisting of 0, 1, 2, or 3;

p is the integer 0 or 1;

q is 1;

r is 0;

$R^3$ is selected from the group consisting of hydrogen, phenyl mono-, di-, or trisubstituted independently with trifluoromethylsulfonylamino, phenyl$C_{1-6}$alkoxy or heteroaryl substituents, (substituted phenyl)amino wherein said substituted phenyl is mono-, di-, or trisubstituted independently with trifluoromethylsulfonylamino, phenyl$C_{1-6}$alkoxy or heteroaryl substituents, N-(carboxymethyl)indolyl or N-($C_{1-6}$alkylcarbonylmethyl)indolyl;

$R^4$ is selected from the group consisting of hydrogen, halogen, or $C_{1-6}$alkyl;

X is nitrogen or nitroso;

m is an integer selected from the group consisting of 0, 1, 2, or 3;

$R^5$ is selected from the group consisting of hydrogen, $C_1$–$C_6$ alkyl, phenyl, phenyl mono-, di-, or trisubstituted independently with hydroxy, $C_{1-6}$alkyl, $C_{1-6}$alkoxy, carboxy$C_{1-6}$alkoxy, halogen, amino, mono- or di($C_{1-6}$alkyl)amino, nitro, carboxy, —COO($C_{1-6}$alkyl), $C_{1-6}$alkylthio, carboxymethylthio, trifluoromethyl, trifluoromethylsulfonylamino, phenyl$C_{1-6}$alkoxy or heteroaryl substituents, $C_1$–$C_6$ alkenyl, or a saturated 5, 6, or 7 membered ring optionally interrupted by 1, 2, 3, or 4 N, S, or O heteroatoms, with the proviso that any two O or S atoms are not bonded to each other;

Z is hydrogen or halogen;

heteroaryl in more detail includes a 5 or 6 membered aromatic ring optionally interrupted by 1, 2, 3 or 4 N, S, or O heteroatoms, with the proviso that any two O or S atoms are not bonded to each other, e.g. pyridine, pyrimidine, pyrrole, pyrazole, imidazole, thiazole, triazole, tetrazole, furan, pyran or thiophene;

substituted heteroaryl in more detail includes heteroaryl mono-, di-, or trisubstituted independently with $C_{1-6}$alkyl or phenyl;

or a pharmaceutically acceptable acid-addition or base-addition salt thereof.

Particular compounds of formula (Ia) include:

A.
- $R^1$ is isopropyl;
- $R^2$ is phenyl.

B.
- $R^1$ is selected from the group consisting of phenyl, 4-methoxyphenyl or 4-dimethylaminophenyl;
- $R^2$ is selected from the group consisting of propyl, isopropyl, butyl or cyclohexyl.

C.
- n is 0 or 1;
- p is 1;
- $R^3$ is selected from the group consisting of phenyl mono-, di-, or trisubstituted independently with trifluoromethylsulfonylamino, phenyl$C_{1-6}$alkoxy or heteroaryl substituents, (substituted phenyl)amino wherein said substituted phenyl is mono-, di-, or trisubstituted independently with trifluoromethylsulfonylamino, phenyl$C_{1-6}$alkoxy or heteroaryl substituents, N-(carboxymethyl)indolyl, N-($C_{1-6}$alkylcarbonylmethyl)indolyl;

D.
- $R^4$ is selected from the group consisting of hydrogen or $C_{1-6}$alkyl.

E.
- m is 0 or 1;
- $R^5$ is selected from the group consisting of $C_1$–$C_6$ alkyl, phenyl, or a saturated 5, 6, or 7 membered ring optionally interrupted by 1, 2, 3, or 4 N, S, or O heteroatoms, with the proviso that any two O or S atoms are not bonded to each other.

F.
- $R^1$ is $C_{1-6}$alkyl;
- $R^2$ is phenyl;
- n is 0 or 1;
- p is 1;
- $R^3$ is selected from the group consisting of phenyl mono-, di-, or trisubstituted independently with trifluoromethylsulfonylamino, phenyl$C_{1-6}$alkoxy or heteroaryl substituents, (substituted phenyl)amino wherein said substituted phenyl is mono-, di-, or trisubstituted independently with trifluoromethylsulfonylamino, phenyl$C_{1-6}$alkoxy or heteroaryl substituents, N-(carboxymethyl)indolyl, N-($C_{1-6}$alkylcarbonylmethyl)indolyl;

$R^4$ is hydrogen of $C_{1-6}$alkyl;

m is 0 or 1;

$R^5$ is selected from the group consisting of $C_1$–$C_6$ alkyl, phenyl, or a saturated 5, 6, or 7 membered ring optionally interrupted by 1, 2, 3, or 4 N, S, or O heteroatoms, with the proviso that any two O or S atoms are not bonded to each other.

The invention still further comprises 1,4-benzodiazapine compounds of the formula (Ia) wherein:

$R^1$ is selected from the group consisting of hydrogen, $C_1$–$C_6$ alkyl, $C_3$–$C_6$cycloalkyl, phenyl, or phenyl mono-, di-, or trisubstituted independently with hydroxy, carboxy$C_{1-6}$alkoxy, halogen, amino, mono- or di($C_{1-6}$alkyl)amino, carboxy, —COO($C_{1-6}$alkyl), $C_{1-6}$alkylthio, carboxymethylthio, trifluoromethylsulfonylamino, phenyl$C_{1-6}$alkoxy or heteroaryl substituents;

$R^2$ is selected from the group consisting of phenyl$C_1$–$C_3$alkyl or phenyl mono-, di-, or trisubstituted independently with hydroxy, carboxy$C_{1-6}$alkoxy, amino, mono- or di($C_{1-6}$alkyl)amino, carboxy, —COO ($C_{1-6}$alkyl), $C_{1-6}$alkylthio, carboxymethylthio, trifluoromethylsulfonylamino, phenyl$C_{1-6}$alkoxy or heteroaryl substituents; or $NR^1R^2$ together form 1,2,3,4-tetrahydroquinoline mono-, di-, or trisubstituted with halogen substituents;

n is an integer selected from the group consisting of 0, 1, 2, or 3;

p is the integer 0 or 1;

q is 1;

r is 0;

$R^3$ is selected from the group consisting of indolyl, N-(carboxymethyl)indolyl, N-($C_1$-$_6$alkylcarbonylmethyl)indolyl, indazoleamino, benzoxy, phenylamino, hydrogen, phenyl, substituted phenyl, (substituted phenyl)amino, heteroaryl, phenyl$C_{1-6}$alkoxy;

$R^4$ is selected from the group consisting of hydrogen, halogen, or $C_{1-6}$alkyl;

X is selected from the group consisting of nitrogen or nitroso;

m is an integer selected from the group consisting of 0, 1, 2, or 3;

$R^5$ is selected from the group consisting of hydrogen, $C_1$–$C_6$ alkyl, phenyl, substituted phenyl, $C_1$–$C_6$ alkenyl, or a saturated 5, 6, or 7 membered ring optionally interrupted by 1, 2, 3, or 4 N, S, or O heteroatoms, with the proviso that any two O or S atoms are not bonded to each other;

Z hydrogen or halogen;

substituted phenyl in more detail includes phenyl mono-, di-, or trisubstituted independently with hydroxy, $C_{1-6}$alkyl, $C_{1-6}$alkoxy, carboxy$C_{1-6}$alkoxy, halogen, amino, mono- or di($C_{1-6}$alkyl)amino, nitro, carboxy, —COO($C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl, $C_{1-6}$alkylsulfinyl or heteroaryl substituents;

heteroaryl in more detail includes a 5 or 6 membered aromatic ring optionally interrupted by 1, 2, 3 or 4 N, S, or O heteroatoms, with the proviso that any two O or S atoms are not bonded to each other, e.g. pyridine, pyrimidine, pyrrole, pyrazole, imidazole, thiazole, triazole, tetrazole, furan, pyran or thiophene;

substituted heteroaryl in more detail includes heteroaryl mono-, di-, or trisubstituted independently with $C_{1-6}$alkyl or phenyl;

or a pharmaceutically acceptable acid-addition or base-addition salt thereof. Still further particular compounds of formula (Ia) include:

a.
$R^1$ is isopropyl;
$R^2$ is di($C_{1-6}$alkyl)aminophenyl.

b.
$R^1$ is selected from the group consisting of phenyl, 4-methoxyphenyl or 4-dimethylaminophenyl;
$R^2$ is selected from the group consisting of propyl, isopropyl, butyl or cyclohexyl.

c.
n is 0 or 1;
p is 1;
$R^3$ is selected from the group consisting of indolyl, N-(carboxymethyl)indolyl, N-($C_1$-$_6$alkylcarbonylmethyl)indolyl, indazoleamino, benzoxy, phenylamino, phenyl mono-, di-, or trisubstituted independently with amino, halogen, trifluoromethylsulfonylamino, phenyl$C_{1-6}$alkoxy or heteroaryl substituents, (substituted phenyl)amino wherein said substituted phenyl is mono-, di-, or trisubstituted independently with carboxy, halogen, trifluoromethylsulfonylamino, phenyl$C_{1-6}$alkoxy or heteroaryl substituents.

d.
$R^4$ is selected from the group consisting or hydrogen or $C_{1-6}$alkyl.

e.
m is 0 or 1;
$R^5$ is selected from the group consisting of $C_1$–$C_6$ alkyl, phenyl, or a saturated 5, 6, or 7 membered ring optionally interrupted by 1, 2, 3, or 4 N, S, or O heteroatoms, with the proviso that any two O or S atoms are not bonded to each other.

f.
$R^1$ is isopropyl;
$R^2$ is di($C_{1-6}$alkyl)aminophenyl;
n is 0 or 1;
p is 1;
$R^3$ is selected from the group consisting of indolyl, N-(carboxymethyl)indolyl, N-($C_{1-6}$alkylcarbonylmethyl)indolyl, indazole, benzoxy, phenyl, phenyl mono-, di-, or trisubstituted independently with amino, carboxy, halogen, trifluoromethylsulfonylamino, phenyl$C_{1-6}$alkoxy or heteroaryl substituents;
$R^4$ is hydrogen;
m is 0 or 1;
$R^5$ is selected from the group consisting of $C_1$–$C_6$ alkyl, phenyl, or a saturated 5, 6, or 7 membered ring optionally interrupted by 1, 2, 3, or 4 N, S, or O heteroatoms, with the proviso that any two O or S atoms are not bonded to each other.

g.
$R^1$ is isopropyl;
$R^2$ is dimethylaminophenyl n is 0;

p is 1;

$R^3$ is carboxyphenylamino;

$R^4$ is hydrogen;

m is 0;

$R^5$ is phenyl;

Z is hydrogen.

The invention still even further comprises 1,4-benzodiazepine compounds of the formula (Ia) wherein:

$R^1$ is selected from the group consisting of hydrogen, $C_1$–$C_6$ alkyl, $C_3$–$C_6$cycloalkyl, phenyl, or substituted phenyl;

$R^2$ is selected from the group consisting of hydrogen, $C_1$–$C_6$ alkyl, phenyl, phenyl$C_1$–$C_3$alkyl or substituted phenyl; or $NR^1R^2$ together form 1,2,3,4-tetrahydroquinoline or 1,2,3,4-tetrahydroquinoline mono-, di-, or trisubstituted independently with $C_{1-6}$alkyl, $C_{1-6}$alkoxy or halogen substituents;

n is an integer selected from the group consisting of 0, 1, 2, or 3;

p is the integer 0 or 1;

q is the integer 0 or 1;

r is the integer 0 or 1, provided that when q is 0 then r is 0;

$R^3$ is selected from the group consisting of hydrogen, phenyl, substituted phenyl, heteroaryl, indolyl, N-(carboxymethyl)indolyl, N-($C_{1-6}$alkylcarbonylmethyl)indolyl, phenyl$C_{1-6}$alkoxy or indazole;

$R^4$ is selected from the group consisting of $C_{1-6}$alkoxy, $C_{1-6}$alkoxymethyl, carboxymethyl or $C_{1-6}$alkoxycarbonylmethyl;

X is selected from the group consisting of nitrogen or nitroso;

m is an integer selected from the group consisting of 0, 1, 2, or 3;

$R^5$ is selected from the group consisting of hydrogen, $C_1$–$C_6$ alkyl, phenyl, substituted phenyl, $C_1$–$C_6$ alkenyl, or a saturated 5, 6, or 7 membered ring optionally interrupted by 1, 2, 3, or 4 N, S, or O heteroatoms, with the proviso that any two O or S atoms are not bonded to each other;

Z is selected from the group consisting of hydrogen or halogen;

substituted phenyl in more detail includes phenyl mono-, di-, or trisubstituted independently with hydroxy, $C_{1-6}$alkyl, $C_{1-6}$alkoxy, carboxy$C_{1-6}$alkoxy, halogen, amino, mono- or di($C_{1-6}$alkyl)amino, nitro, carboxy, —COO($C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl, $C_{1-6}$alkylsulfinyl or heteroaryl substituents;

heteroaryl in more detail includes a 5 or 6 membered aromatic ring optionally interrupted by 1, 2, 3 or 4 N, S, or O heteroatoms, with the proviso that any two O or S atoms are not bonded to each other, e.g. pyridine, pyrimidine, pyrrole, pyrazole, imidazole, thiazole, triazole, tetrazole, furan, pyran or thiophene;

substituted heteroaryl in more detail includes heteroaryl mono-, di-, or trisubstituted independently with $C_{1-6}$alkyl or phenyl;

or a pharmaceutically acceptable acid-addition or base-addition salt thereof.

The invention still even further additionally comprises 1,4-benzodiazepine compounds of the formula (Ib):

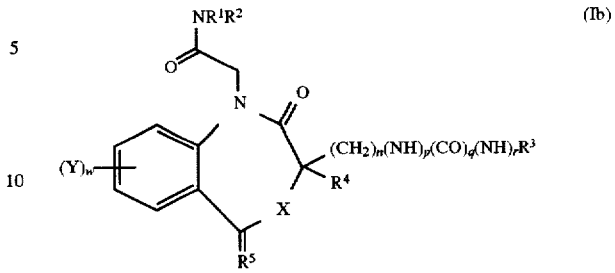

wherein:

$R^1$ is selected from the group consisting of $C_1$–$C_6$ alkyl, $C_3$–$C_6$cycloalkyl, phenyl, or phenyl mono-, di-, or trisubstituted independently with hydroxy, $C_{1-6}$alkyl, $C_{1-6}$alkyl substituted with 1-8 fluorine atoms, $C_{1-6}$alkoxy, carboxy$C_{1-6}$alkoxy, fluoro, amino, mono- or di($C_{1-6}$alkyl)amino, —COO($C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl or $C_{1-6}$alkylsulfinyl substituents;

$R^2$ is selected from the group consisting of $C_3$–$C_6$ alkyl, $C_3$–$C_6$cycloalkyl, $C_3$–$C_6$alkenyl, benzyl, phenyl$C_1$–$C_3$alkyl or phenyl mono-, di-, or trisubstituted independently in the ortho or para positions with hydroxy, $C_{1-6}$alkyl, $C_{1-6}$alkoxy, cyano, benzyloxy, pyrrolidino, morpholino, carboxy$C_{1-6}$alkoxy, chloro, amino, mono- or di($C_{1-6}$alkyl)amino, —COO($C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl or $C_{1-6}$alkylsulfinyl substituents; or $NR^1R^2$ together form 1,2,3,4-tetrahydroquinoline or benzazepine mono-, di-, or trisubstituted independently with $C_{1-6}$alkyl, $C_{1-6}$alkoxy or halogen substituents;

n is an integer selected from the group consisting of 0, 1, 2, or 3;

p is an integer selected from the group consisting of 0 or 1;

q is an integer selected from the group consisting of 0 or 1;

r is an integer selected from the group 0 or 1, provided that when q is 0 then r is 0;

$R^3$ is selected from the group consisting of hydrogen, $C_{1-6}$alkyl, $C_{1-6}$cycloalkyl, phenyl, phenyl mono-, di-, or trisubstituted independently with $C_{1-6}$alkyl, hydroxy, $C_{1-6}$alkoxy, halogen, amino, mono- or di($C_{1-6}$alkyl) amino, nitro, carboxy, —COO($C_{1-6}$alkyl), carboxy$C_{1-6}$alkoxy, carboxy$C_{1-6}$alkyl, carboxymethylthio, heteroaryl, mono- or di($C_{1-6}$alkyl)aminoalkyl, or trifluoromethyl, trifluoromethoxy, $C_{1-6}$alkylthio, —SO$_v$($C_{1-6}$alkyl), —SO$_v$NH($C_{1-6}$alkyl), —SO$_v$CF$_3$ or —SO$_v$C$_6$H$_5$, —(CH$_2$)$_v$NO$_2$, —(CH$_2$)$_v$CN, —(CH$_2$)$_v$COOH, —(CH$_2$)$_v$COO($C_{1-6}$alkyl), —(CH$_2$)$_v$SCH$_3$, —(CH$_2$)$_v$SOCH$_3$, —(CH$_2$)$_v$SO$_2$CH$_3$, —(CH$_2$)$_v$CONH$_2$, —SCH$_2$COOH, —CONH(SO$_2$CH$_3$), —CONH(SO$_2$CF$_3$), —(CH$_2$)$_v$N($C_{1-6}$alkyl)$_2$, —(CH$_2$)$_v$NH(SO$_2$CF$_3$), —(CH$_2$)$_v$N(SO$_2$CF$_3$)($C_{1-6}$alkyl), —(CH$_2$)$_v$SO$_2$NHCO($C_{1-6}$alkyl), —(CH$_2$)$_v$SO$_2$N($C_{1-6}$alkyl)CO($C_{1-6}$alkyl), —(CH$_2$)$_v$CONHSO$_2$($C_{1-6}$alkyl), —(CH$_2$)$_v$CON($C_{1-6}$alkyl)SO$_2$($C_{1-6}$alkyl), —(CH$_2$)$_v$NHR$^6$ or —(CH$_2$)$_v$OR$^7$ substituents, heteroaryl, provided when $R^3$ is oxadiazole then $R^4$ is not hydrogen, heteroaryl substituted with halogen, $C_{1-6}$alkyl, hydroxy, nitro, cyano, carboxy, $C_{1-6}$alkoxy, benzoxy, —COO($C_{1-6}$alkyl), amino, mono- or di($C_{1-6}$alkyl)amino, phenyl or benzyl substituents, napthyl, bicycloheteroaryl or bicycloheteroaryl N-substituted independently with hydroxy, carboxyalkyl, phenyl, heteroaryl, $C_{1-6}$alkoxy or cyano substituents, further provided when n is 1, p is 0, q is 0 and r is 0 then heteroaryl, substituted heteroaryl, bicycloheteroaryl and substituted bicycloheteroaryl are bound at the 3 position, still further provided that when n is 0, p is 1, q is 1 and r is o then heteraryl, substituted heteroaryl, bicycloheteroaryl and substituted bicycloheteroaryl are bound at the 2 position;

$R^6$ is hydrogen, $C_{1-6}$ alkyl, —$SO_3H$, —$SO_2CH_3$, —$SO_2CF_3$, —$SO_2C_6H_5$, —COO($C_4H_9$) or —COO($CH_2C_6H_5$);

$R^7$ is hydrogen, $C_{1-6}$alkyl, $C_{3-6}$cycloalkyl, —$CH_2C_6H_5$, —$CH_2COOH$, — $CH_2CONH_2$, —$CH_2CONH(C_{1-6}$alkyl), —$CH_2CON(C_{1-6}$alkyl)$_2$ or

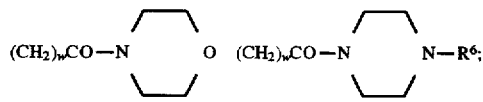

v is an integer selected from the group consisting of 0, 1 or 2;

w is an integer selected from the group consisting of 0, 1 or 2;

$R^4$ is selected from the group consisting of hydrogen, halogen, or $C_{1-6}$alkyl;

X is selected from the group consisting of nitrogen, nitroso or $NR^8$;

$R^8$ is selected from the group consisting of hydrogen, $C_{1-6}$alkyl or $(CH_2)_kR^9$;

k is an integer selected from the group consisting of 1, 2, 3 or 4;

$R^9$ is selected from the group consisting of amino, mono- or di($C_{1-6}$alkyl)amino, pyrrolidinyl, morpholinyl, piperidinyl, piperazinyl, phenyl, nitro, carboxyl, carboxamide, hydroxyl, heteroaryl, —COO($C_{1-6}$alkyl), —CONH($C_{1-6}$alkyl), —$SO_t(C_{1-6}$alkyl), —$SO_tNH(C_{1-6}$alkyl), —$SO_tCF_3$, —$SO_tC_6H_5$, —O($C_{1-6}$alkyl) or —CON($C_{1-6}$alkyl)$_2$;

t is an integer selected from the group consisting of 0, 1 or 2;

$R^5$ is oxygen; or $XR^5$ together form a heteroaryl or substituted heteraryl where X is nitrogen;

Y is H, $C_{1-6}$alkyl or halogen;

heteroaryl in more detail includes a 5 or 6 membered aromatic ring optionally interrupted by 1, 2, 3 or 4 N, S, or O heteroatoms, with the proviso that any two O or S atoms are not bonded to each other;

substituted heteroaryl in more detail includes heteroaryl mono-, di- or trisubstituted independently with hydroxy, $C_{1-6}$alkyl, $C_{1-6}$alkoxy, carboxy$C_{1-6}$alkoxy, halogen, amino, mono- or di($C_{1-6}$alkyl)amino, nitro, carboxy, —COO($C_{1-6}$alkyl), —CONH($C_{1-6}$alkyl), $C_{1-6}$alkylthio, carbosamide, carboxymethylthio, trifluoromethyl, —CONH($C_{1-6}$alkyl), —CONH($C_{1-6}$alkyl)$_2$, —$SO_2(C_{1-6}$alkyl), —$SO_2NH(C_{1-6}$alkyl), —$SO_2CF_3$ or —$SO_2C_6H_5$, pyrrolidinyl, morpholinyl, piperidinyl, piperazinyl, trifluoromethylsulfonylamino, phenyl$C_{1-6}$alkoxy, $C_{1-6}$alkylsulfonyl, $C_{1-6}$alkylsulfinyl, phenyl, carboxamide, or heteroaryl substituents;

z is an integer selected from the group consisting of 0, 1 or 2;

bicycloheteroaryl in more detail is a 9 or 10 membered bicyclo aromatic ring interrupted by 1, 2, 3 or 4 N, O or S heteroatoms, with the proviso that any two O or S heteroatoms are not bonded to each other, with the further proviso that bicycloheteroaryl is not quinoline;

substituted bicycloheteroaryl in more detail includes bicyclo heteroaryl mono-, di-, or trisubstituted independently with ($C_{1-6}$alkyl), carboxy($C_{1-6}$alkyl), phenyl ($C_{1-6}$alkyl) or ($C_{1-6}$alkyl)COO($C_{1-6}$alkyl);

or a pharmaceutically acceptable acid-addition or organic base-addition salt thereof.

Suitable pharmaceutically acceptable salts of the compounds of formula (I) include acid addition salts formed with acids, e.g. hydrochlorides, hydrobromides, sulfates, alkyl- or arylsulfonates (methanesulfonates or p-toluenesulfonates), phosphates, acetates, citrates, succinates, lactates, tartrates, fumarates, and maleates; and base salts such as alkali metal salts e.g; sodium salts. The solvates may, for example, be hydrates.

Other salts which are not pharmaceutically acceptable may be useful in the preparation of compounds of formula (I) and these form a further aspect of the invention.

It is to be understood that the present invention encompasses the individual enantiomers of the compounds represented by formula (I) above as well as wholly or partially racemic mixtures thereof. The present invention also covers the individual enantiomers of the compounds represented by formula (I) above as mixtures with diastereoisomers thereof in which one or more of the two stereocenters is inverted.

GENERAL CHEMISTRY PROCEDURES

Compounds of general formula (I) may be prepared by methods known in the art of organic synthesis, as shown in part by the following processes A–I and schemes 1–5. For any of these processes and schemes, it may be necessary and/or desirable to protect sensitive or reactive groups. Protecting groups are employed according to standard methods of organic synthesis (T. W. Green and P. G. M. Watts (1991) *Protecting Groups in Organic Synthesis*, John Wiley & Sons). These groups are removed at a convenient stage of synthesis using methods known from the art. Thus, for example, amino groups may be protected by a group selected from aralkyl (e.g. benzyl), acyl, or sulfonyl, e.g. allylsulfonyl, phthalimide, or tosyl; subsequent removal of the protecting group being effected when desired by hydrolysis or hydrogenolysis as appropriate using standard conditions. Hydroxyl and carboxyl groups may be protected using any conventional hydroxyl or carboxyl protecting group. Examples of suitable hydroxyl and carboxyl protecting groups include groups selected from alkyl, e.g. methyl, tert-butyl, or methoxymethyl, aralkyl, e.g. benzyl, diphenylmethyl, or triphenylmethyl, heterocyclic groups such as tetrahydropyranyl, acyl, e.g. acetyl or benzoyl, and silyl groups such as trialkylsilyl, e.g. tert-butyldimethylsilyl. The hydroxyl protecting groups may be removed by conventional techniques. Thus, for example, alkyl, silyl, acyl, and heterocyclic groups may be removed by hydrolysis under acidic or basic conditions. Aralkyl groups such as triphenylmethyl may similiarly be removed by hydrolysis under acidic conditions. Aralkyl groups such as benzyl may be cleaved by hydrogenolysis in the presence of a Noble metal catalyst such as palladium-on-charcoal. Silyl groups may also conveniently be removed using a source of fluoride ions such as tetra-n-butylammonium fluoride.

As used herein the symbols and conventions used in these processes, schemes and examples are consistant with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); psi (pounds per square inch); M (molar); mM (millimolar); i. v. (intravenous); Hz (Hertz); mol (moles); RT (room temperature); min (minutes); h (hours); M.p. (melting point); TLC (thin layer chromatography); MeOH (methanol); TFA (trifluoroacetic acid); THF (tetrahydrofuran); dimethylsulfoxide (DMSO); EtOAc (ethyl acetate); dichloromethane (DCM); dimethylformamide (DMF); 1, 1-carbonyldiimidazole (CDI); isobutylchloroformate (iBuCF); N-hydroxysuccinimide (HOSu); N-hydroxybenztriazole (HOBT); ethylcarbodiimide hydrochloride (EDC); bis(2-oxo-3-oxazolidinyl) phosphinic chloride (BOP); tert-butyloxycarbonyl (BOC); dicyclohexylcarbodiimide (DCC); benzyloxycarbonyl (Cbz). All references to ether are to diethyl ether. Unless otherwise indicated, all temperatures are expressed in °C. (degrees Centigrade). All reactions conducted at room temperature unless otherwise noted.

The $^1$HNMR spectra were recorded on either a Varian VXR-300 or a Varian Unity-300 instrument. Chemical shifts are expressed in parts per million (ppm, δ units). Coupling constants are in units of hertz (Hz). Splitting patterns are designated as s, singlet; d, doublet; t, triplet; q, quartet; m, multiplet; b, broad.

Low-resolution mass spectra (MS) were recorded on a JOEL JMS-AX505HA, JOEL SX-102 or a SCIEX-APIiii spectrometers. All mass spectra were taken in the positive ion mode under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Rotations were recorded on a Perkin-Elmer 241 polarimeter. All reactions were monitored by thin-layer chromatography on 0.25 mm E. Merck silica gel plates (60F-254), visualized with UV light, 7% ethanolic phosphomolybdic acid or p-anisidehyde solution. Flash column chromatography was performed on silica gel (230–600 mesh, Merck).

Products were purified by preparative reversed phase high pressure liquid chromatography (RP-HPLC) using a Waters Model 3000 Delta Prep equipped with a Delta-pak radial compression cartridge ($C_{18}$, 300 A, 15 μg, 47 mm×300 mm). Linear gradients were used in all cases and the flow rate was 100 mL/minute ($t_0$=5.0 min.). All solvents contained 0.1% TFA. Analytical purity was assessed by RP-HPLC using a Waters 600E system equipped with a Waters 990 diode array spectrometer (λ range 200–600 nM). The stationary phase was a Vydac $C_{18}$ column (5μ, 4.6 mm×250 mm). The flow rate was 1.0 to 1.5 ml/min. ($t_0$=2.8 or 3.0 min.) and the solvent systems were as described above. Data reported as tr, retention time in minutes (% acetonitrile over time).

For the following Processes A–P and schemes 1–5, $R^1$, $R^2$, $R^4$, $R^5$, $R^6$, $R^7$, $R^8$ and $R^9$, k, m, n, p, q, r, t, v, w and z, X, Y and Z are defined as for formula (I) above.

According to general process A, certain compounds of formula (I) may be prepared by the reaction of an intermediate of formula (II)

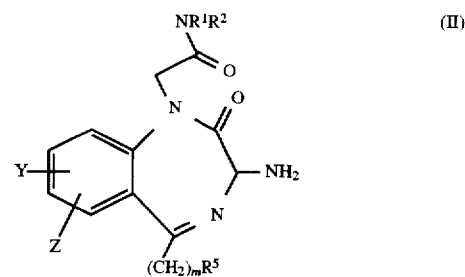

with isocyanates of formula (III), carbamoyl chlorides of formula (IV), imidazolides of formula (V) or nitrophenyl carbamates of formula (VI):

Isocyanates of formula (III) may be purchased or prepared by the reaction of amines of formula (VII):

$$H_2N\text{—}R^3 \qquad (VII)$$

with phosgene or triphosgene in a suitable solvent such as methylene chloride. Carbamoyl chlorides of formula (IV) are prepared in situ by the reaction of amines of formula (VII) with phosgene or triphosgene in a suitable solvent such as methylene chloride at 0° C. Imidazolides of formula (V) are prepared by treatment of amines of formula (VII) with carbonyl diimidazole in a suitable solvent (dichloromethane, ether, tetrahydrofuran) at a suitable temperature (0°–800° C.). Nitrophenyl carbamates of formula (VI) are prepared by the reaction of amines of formula (VII) with nitrophenyl chloroformate in the presence of a tertiary amine base (pyridine, triethylamine) in a suitable solvent (dichloromethane) at a temperature of 0°–50° C.

According to process B, certain compounds of general formula (I) may be prepared by the conversion of a compound of formula (II) to a compound of formula (VIII) and reacted in situ with amines of formula (VII) as defined above in a suitable solvent such as dichlormethane, tetrahydrofuran, N, N-dimethylformamide or acetonitrile, optionally at a temperature ranging from ambient temperature to the reflux temperature of the solvent.

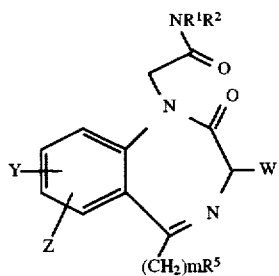
(VIII)

Wherein W is selected from formula VIIIa, b, c or d:

(VIIIa)

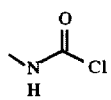
(VIIIb)

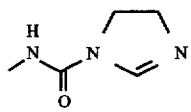
(VIIIc)

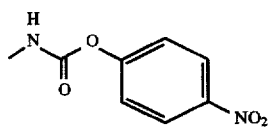
(VIIId)

Under the same conditions described previously, isocyanate of formula (VIIIa) or carbamoyl chloride of formula (VIIIb) are prepared by treatment of a compound of formula (II) with phosgene or triphosgene; the imidazolide of formula (VIIIc) is prepared by treatment of the amine of formula (II) with carbonyl diimidazole; and the nitrophenyl carbamate of formula (VIIId) is prepared by treatment of the amine of formula (II) with nitrophenyl chloroformate.

According to process C, certain compounds of general formula (I) may be prepared by the reaction of a compound of formula (II) with acids of formula (IX) in the presence of a <p align="right">HOOC—R³       (IX)</p> suitable dehydrating agent such as dicyclohexylcarbodiimide (DCC), 3-dimethyl-aminopropyl-3-ethylcarbodiimide hydrochloride (EDC), or 4-benzotriazol-1-yloxytris-(dimethylamino)phosphonium hexafluorophosphate (BOP), particularly in the presence of a suitable alcohol (N-hydroxysuccinimide or N-hydroxybenztriazole) to generate an active ester in situ.

Alternatively, certain compounds of general Formula (I) may be obtained by reaction of a compound of formula (II) with acid chlorides (X) or acid anhydrides (XI).

(X)

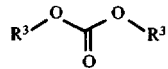
(XI)

Particular solvents for process C include N,N-dimethylformamide, dichloromethane or tetrahydrofuran. Preferred temperatures are between 0°–60° C. Particular bases include triethylamine, N-methylmorpholine or N,N-dimethylaminopyridine.

According to process D, certain compounds of general formula (I) may be prepared by treatment of a compound of formula (XII) with an alkali metal alkoxide.

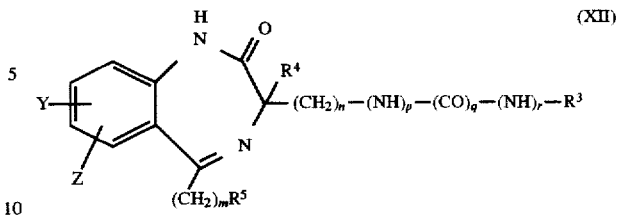
(XII)

alkali metal hydride, alkyl lithium or alkali metal disilylazide in a suitable solvent, such as N,N-dimethylformamide or tetrahydrofuran at 0° C., followed by the addition of a halo acetamide of formula (XIII).

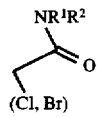
(XIII)

Intermediate halides of general formula (XIII) may be prepared by the reaction of amines of formula (XIV)

<p align="right">HNR¹R²       (XIV)</p> with bromoacetyl bromide, chloroacetyl chloride or bromoacetyl chloride in an aprotic solvent such as dichloromethane, tetrahydrofuran, diethyl ether or acetonitrile at 0° C., in the presence of a tertiary amine base, such as triethylamine.

Amines of formula (XIV) are purchased or prepared by reductive amination of an appropriate aldehyde or ketone of formula (XV) by amines of formula (XVI).

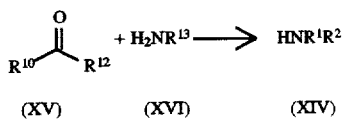

(XV)     (XVI)     (XIV)

wherein $R^{10}$, $R^{12}$, and $R^{13}$ are selected from the group consisting of hydrogen, $C_1$–$C_6$ alkyl, $C_3$–$C_6$cycloalkyl, phenyl, phenyl$C_1$–$C_3$alkyl or phenyl mono-, di-, or trisubstituted independently with hydroxy, $C_{1-6}$alkyl, $C_{1-6}$alkoxy, carboxy$C_{1-6}$alkoxy, fluorine, amino, mono- or di($C_{1-6}$alkyl) amino, —COO($C_{1-6}$alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl, $C_{1-6}$alkylsulfinyl or heteroaryl substituents in the presence of a suitable reducing agent, such as sodium cyanoborohydride or sodium bis-acetoxyborohydride. These reactions may be conducted at ambient temperature in suitable solvents, such as ethanol, methanol, or ethanol and acetic acid (for sodium cyanoborohydride) or dichloromethane or tetrahydrofuran (for sodium bis-acetoxyborohydride).

According to general process E, certain compounds of general formula (I) may also be prepared by the reaction of compounds of formula (XVII) with a suitable

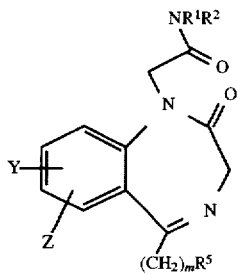

base, such as an alkali metal alkoxide, alkali metal hydride, alkyl lithium, or alkali metal disilylazide, followed by the addition of a halide of formula (XVIII).

 (XVIII)

These reactions are particularly run at −80° to 25° C. in a suitable solvent such as tetrahydrofuran, dichloromethane or N, N-dimethylformamide.

According to general process F, certain compounds of general formula (I) may also be prepared by the reaction a compound of formula (XIX)

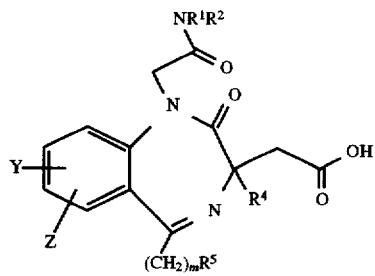 (XIX)

with amines (VII) in the presence of a suitable dehydrating agent (DCC, EDC, BOP) or bromo-tris-pyrrolidino-phosphonium hexfluoro phosphate (PyBrop). Suitable solvents for process F include N, N-dimethylformamide or dichloromethane. The reaction is run at room temperature with a suitable tertiary amine base, such as triethylamine, N-methyl morpholine or N, N-dimethylaminopyridine.

According to process G, certain compounds of general formula (I) may also be prepared by treatment of a compound of formula (XX)

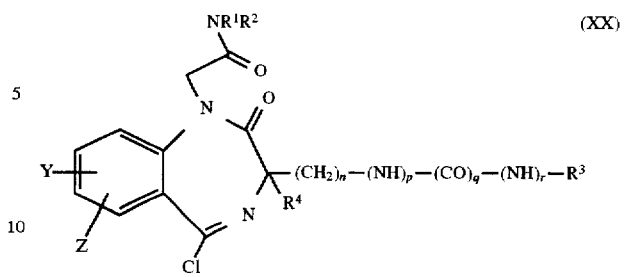 (XX)

with amines of formula (XXI)

 (XXI)

wherein $R^{16}$ and $R^{17}$ are as described for $R^5$ of formula (I) above. This reaction is particularly run in a suitable solvent, such as dichloromethane, initially at 0°–5° C., then allowed to warm to ambient temperature.

According to general process H, certain derivatives of formula (XXII) contained within general formula (I) may be further converted by treatment with an appropriate base, such as an

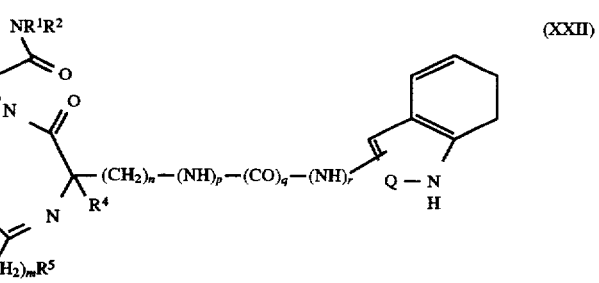 (XXII)

alkali metal hydride, and reaction with halides of general formula (XXIII) in a suitable

 (XXIII)

solvent, such as dichloromethane or N,N-dimethylformamide, to provide compounds also contained within general formula (I).

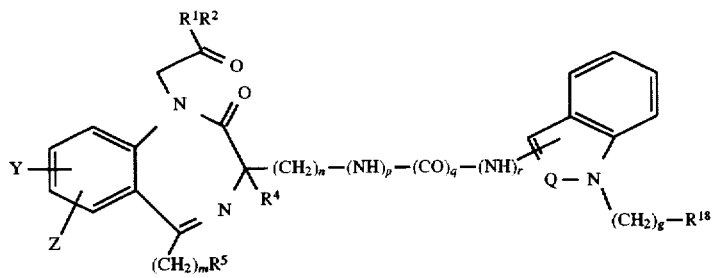

where Q is CH or N, g is 0–6 and $R^{18}$ is selected from the group consisting of H, $C_1$–$C_6$ alkyl, phenyl, substituted phenyl, COO($C_1$–$C_4$ alkyl,) or COO($CH_2C_6H_5$). If necessary, the protecting group may be removed with acidic, basic or hydrogenolytic conditions to provide additional examples of compounds of general formula (I), where $R^{18}$ is COOH.

According to general process I, certain derivatives of formula (XXIV) contained within

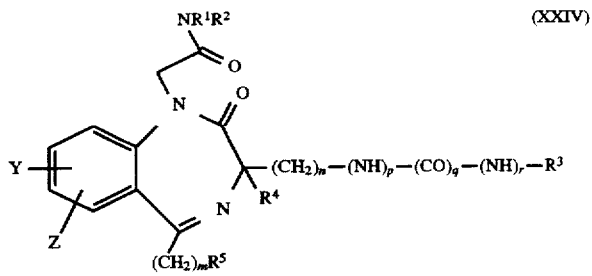

general formula (I) may be further converted by treatment with an appropriate oxidizing agent, such as m-chloroperoxybenzoic acid, in a suitable solvent such as dichloromethane, at temperatures ranging from –20° to 50° C. to further provide compounds contained within general formula (I).

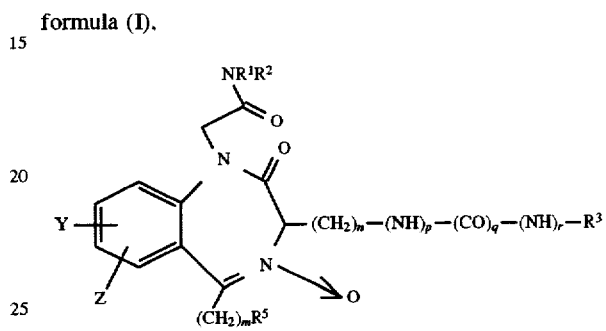

While compounds of formula (II) may be prepared according to methods published in the literature (Bock et al, 1987, *Tetrahedron Letters* 28(9), 939–942; Bock et al, 1987 *J. Org. Chem.* 52, 3232–3239), a particular route for their preparation is illustrated in Scheme 1, below. This route is conveniently employed for m=0–4 and $R^5$=$C_1$–$C_6$ alkyl, phenyl, substituted phenyl, pyridyl, or substituted pyridine. The benztriazole intermediate of formula (XXV) is prepared according to published procedures (Katritzky et al 1989, *J. Chem. Soc. Chem. Commun.* 337–338).

SCHEME 1

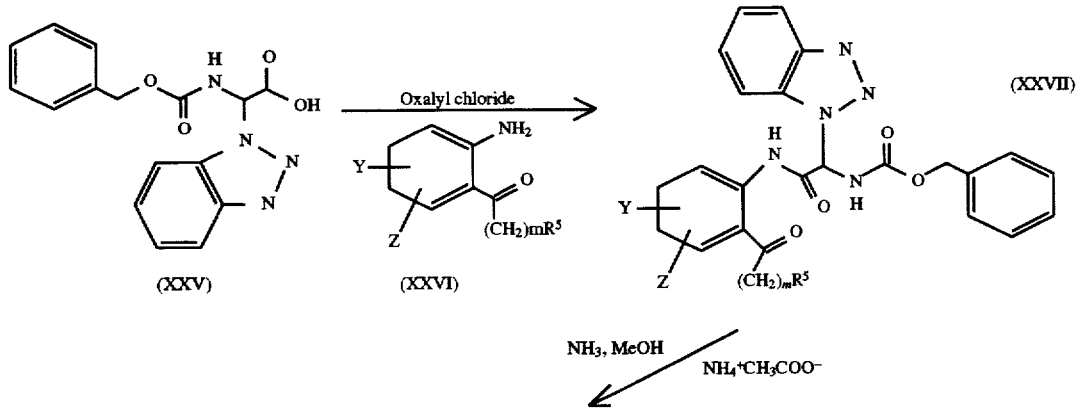

-continued
SCHEME 1

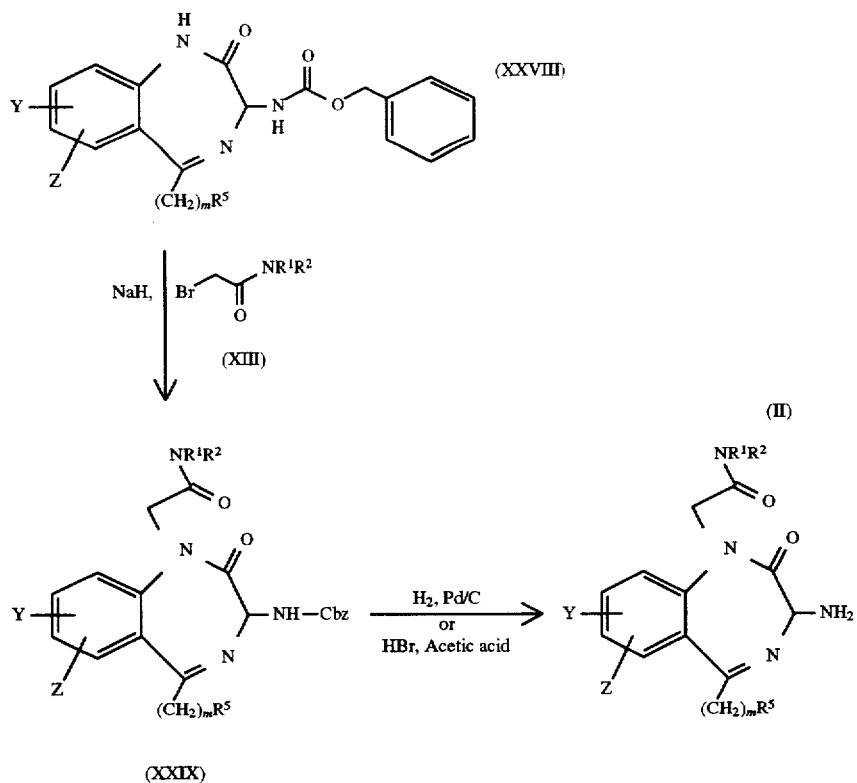

Alternatively, compounds of formula (XXX) may be reacted with dibromobarbituric

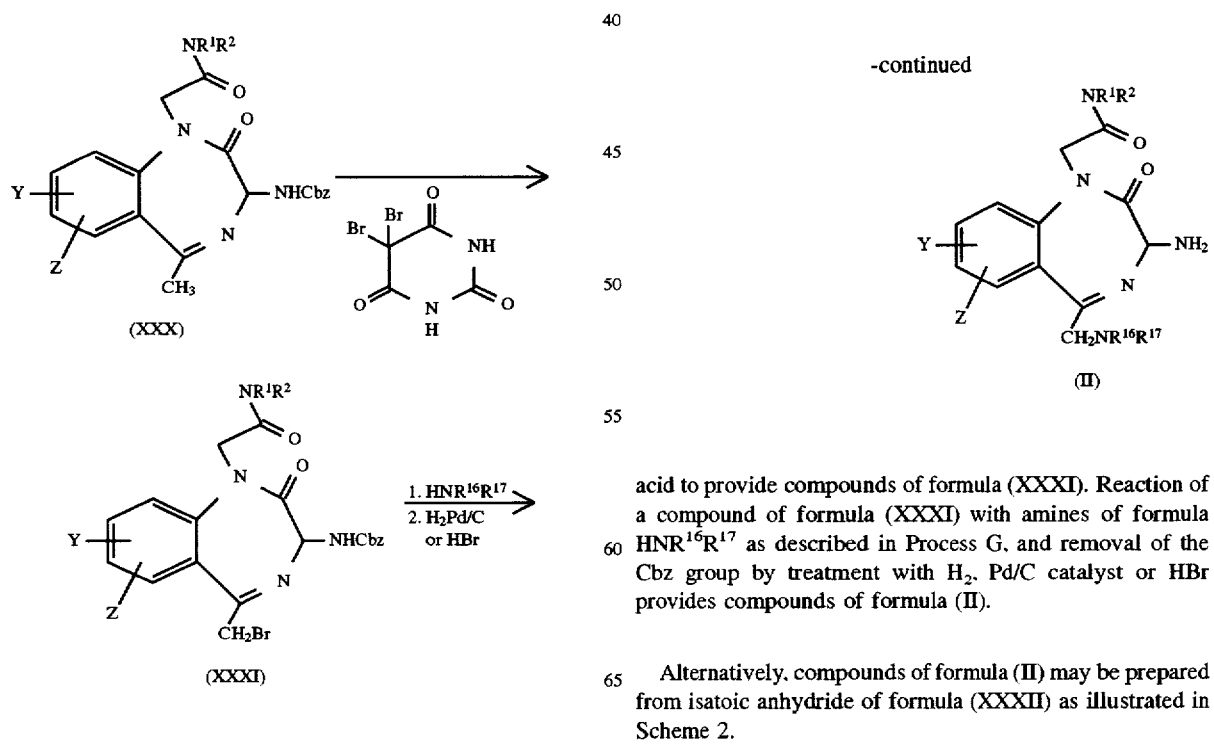

acid to provide compounds of formula (XXXI). Reaction of a compound of formula (XXXI) with amines of formula $HNR^{16}R^{17}$ as described in Process G, and removal of the Cbz group by treatment with $H_2$, Pd/C catalyst or HBr provides compounds of formula (II).

Alternatively, compounds of formula (II) may be prepared from isatoic anhydride of formula (XXXII) as illustrated in Scheme 2.

SCHEME 2
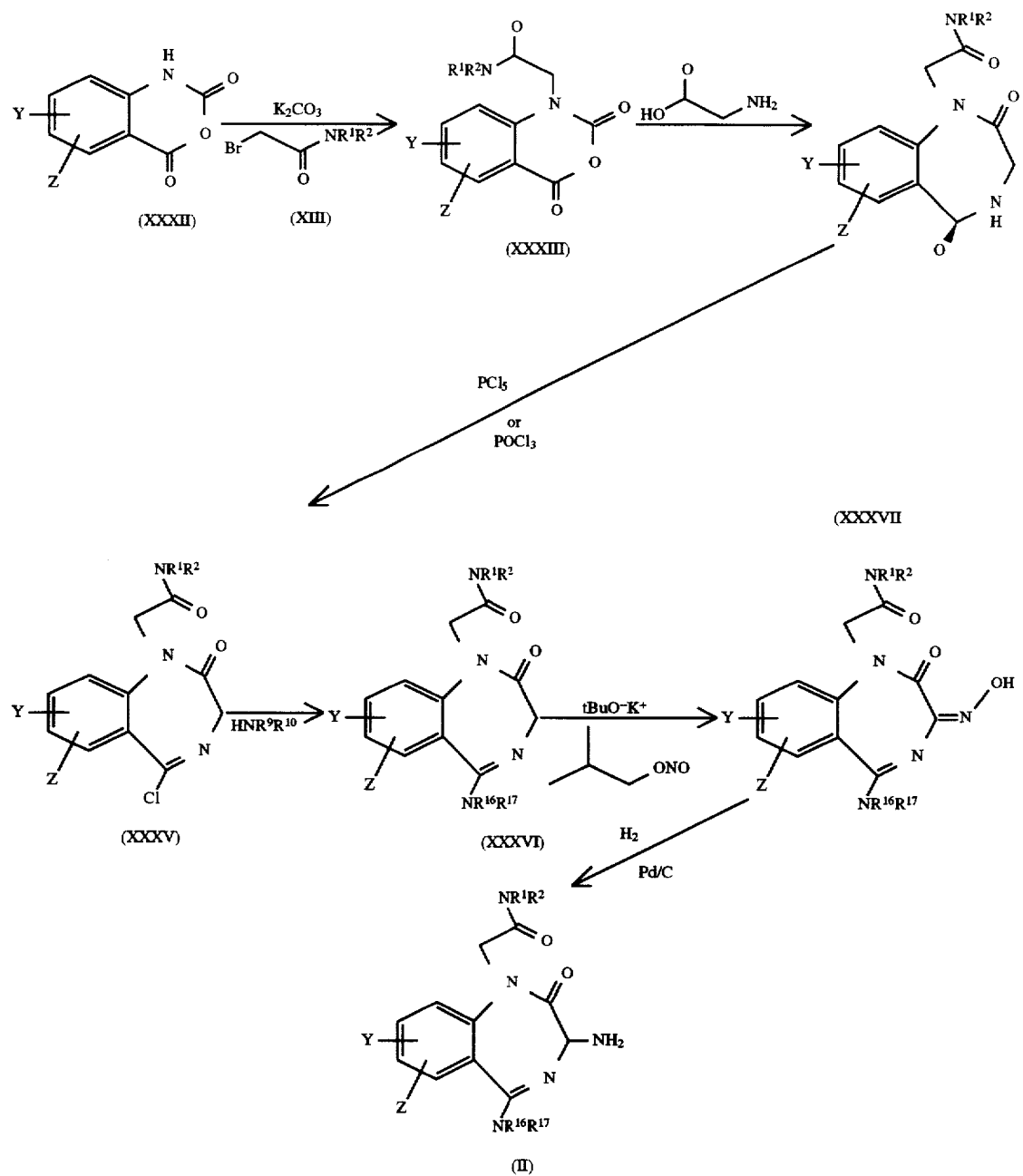
Compounds of formula (XIIa) are prepared from compounds of formula (XXVIII), as described in Scheme 1, according to the procedures outlined in Scheme 3.

Scheme 3

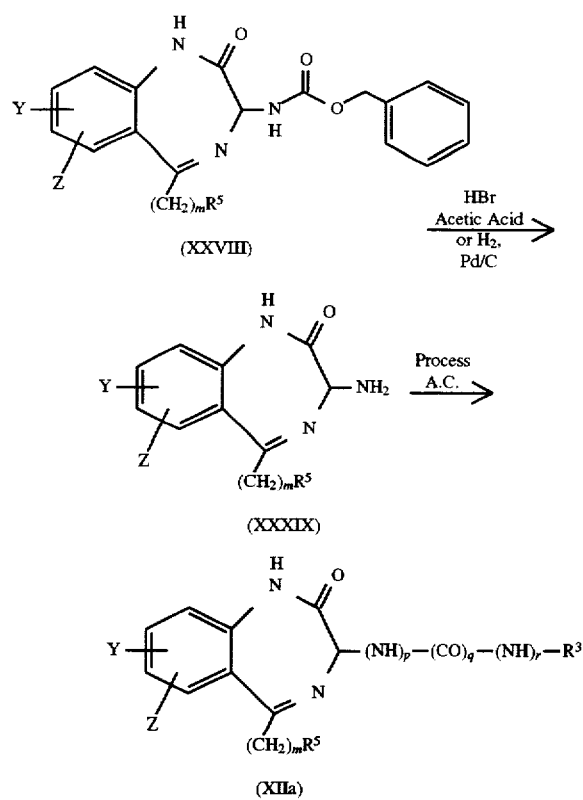

Following removal of the Cbz protecting group from formula (XXVIII) using acidic or hydrogenolytic conditions, the resulting amine of formula (XXXIX) may be treated (as previously described for processes A or C) with isocyanates of formula (III), carbamoyl chlorides of formula (IV), imidazolides of formula (V), nitrophenyl carbamates of formula (VI), acids of formula (IX) in the presence of a suitable dehydrating agent (BOP, DCC, EDC), acid chlorides of formula (X) or acid anhydrides of formula (XI) to provide compounds of formula (XIIa).

Alternatively, compounds of formula (XII) may be prepared according to the procedures published in Evans, et al 1987 *J. Med. Chem.* 30,1229–1239.

Compounds of formula (XVII) may be prepared by alkylation of a compound of formula (XL), prepared according to published procedures (Bock et al, 1987 *J. Org. Chem.* 52, 3232–3239.).

Scheme 4

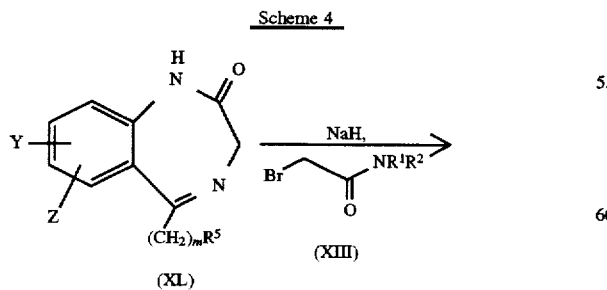

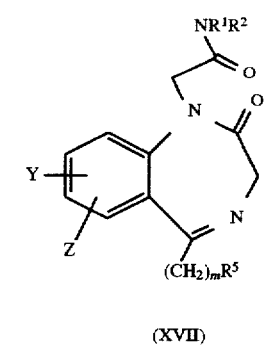

Compounds of formula (XIX) are prepared by treatment of compounds of formula (XVII) with a suitable base (alkali metal alkoxide, alkali metal hydride, alkyl lithium, or alkali metal disilylazide) in a suitable solvent (THF, DMF), followed by reaction with a compound of formula (XLI).

(Cl, Br)—CH$_2$-COOC1-C$_4$ alkyl  (XLI)

Certain compounds of formula (XX) may be prepared from compounds of formula XXXIII (Scheme 2) by the series of reactions illustrated in Scheme 5.

Scheme 5

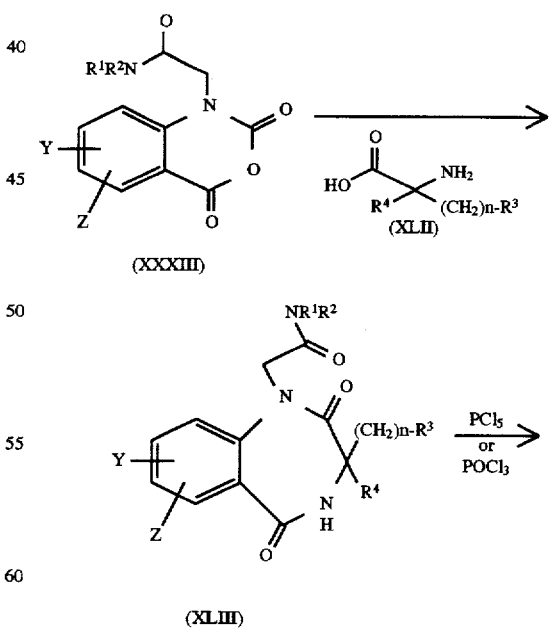

-continued
Scheme 5

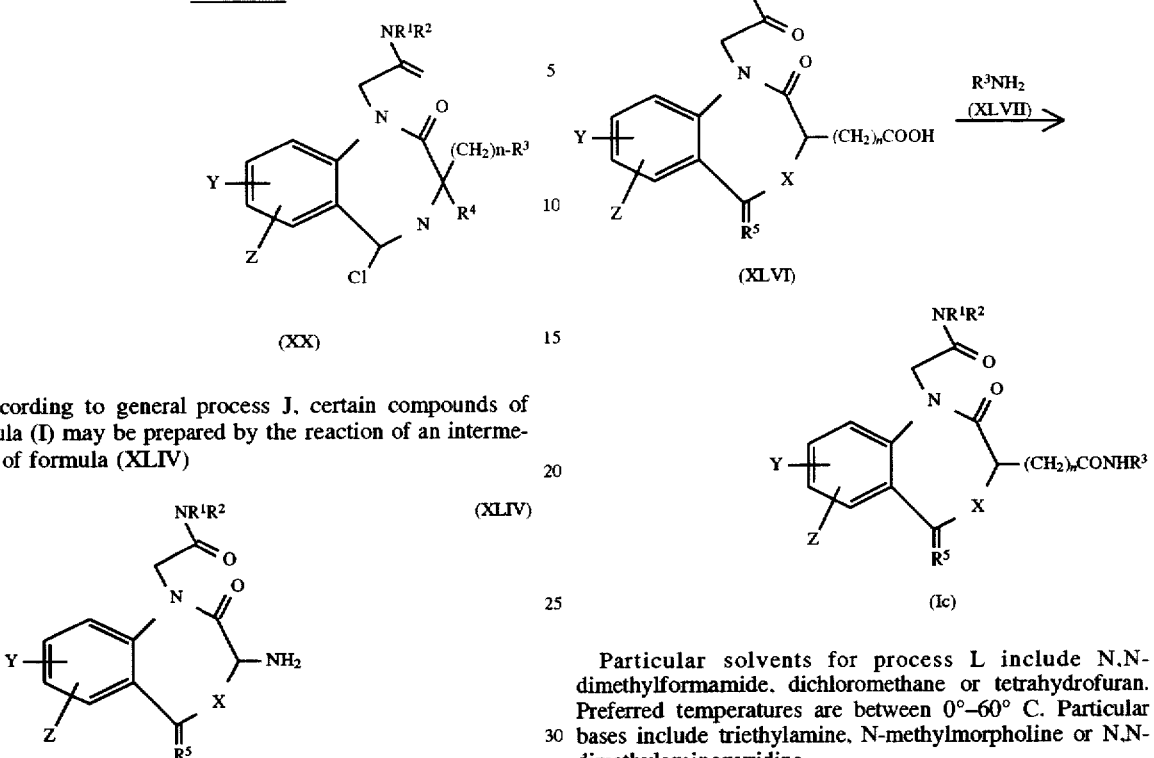

According to general process J, certain compounds of formula (I) may be prepared by the reaction of an intermediate of formula (XLIV)

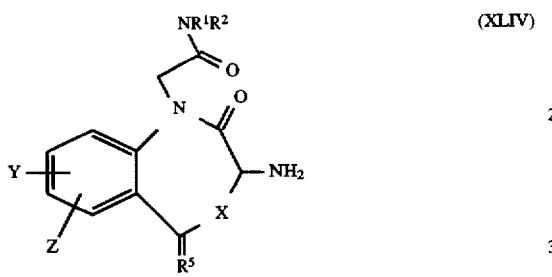

with isocyanates of formula (III), imidazolides of formula (IV), carbamoyl chlorides of formula (V), or nitrophenyl carbamates of formula (VI), as seen above.

According to process K, certain compounds of general formula (I) may be prepared by the reaction of a compound of formula (XLIV) with acids of formula (XLV) in the presence of a suitable dehydrating agent such as

HOOC—R⁴ (XLV)

dicyclohexylcarbodiimide (DCC), 3-dimethylaminopropyl-3-ethylcarbodiimide hydrochloride (EDC), or 4-benzotriazol-1-yloxytris-(dimethylamino)phosphonium hexafluorophosphate (BOP), particularly in the presence of a suitable alcohol (N-hydroxysuccinimide or N-hydroxybenztriazole) to generate an activated ester in situ.

Alternatively, certain compounds of general Formula (I) may be obtained by reaction of a compound of formula (XLIV) with acid chlorides or acid anhydrides Preferred solvents for process K include N,N-dimethylformamide, dichloromethane or tetrahydrofuran. Preferred temperatures are between 0°–60° C. Preferred bases include triethylamine, N-methylmorpholine or N,N-dimethylaminopyridine.

According to process L, compounds of general formula (Ic) may also be prepared by the reaction of acids of formula (XLVI) with amines of formula (XLVII) in the presence of a suitable dehydrating agent such as dicyclohexylcarbodiimide (DCC), 3-dimethylaminopropyl-3-ethylcarbodiimide hydrochloride (EDC), or 4-benzotriazol-1-yloxytris-(dimethylamino)phosphonium hexafluorophosphate (BOP), particularly in the presence of a suitable alcohol (N-hydroxysuccinimide or N-hydroxybenztriazole) to generate an active ester in situ.

Particular solvents for process L include N,N-dimethylformamide, dichloromethane or tetrahydrofuran. Preferred temperatures are between 0°–60° C. Particular bases include triethylamine, N-methylmorpholine or N,N-dimethylaminopyridine.

Alternatively, according to process M, compounds of formula (Id), where R⁸ is not hydrogen, may also be prepared by treatment of compounds of formula (XLVIII) with a suitable base, such as an alkali metal alkoxide, alkali metal hydride, alkyl lithium or alkali metal disilylazide in a suitable solvent, such as N,N-dimethylformamide or tetrahydrofuran at 0° C., followed by the addition of a halide of formula (XLIX).

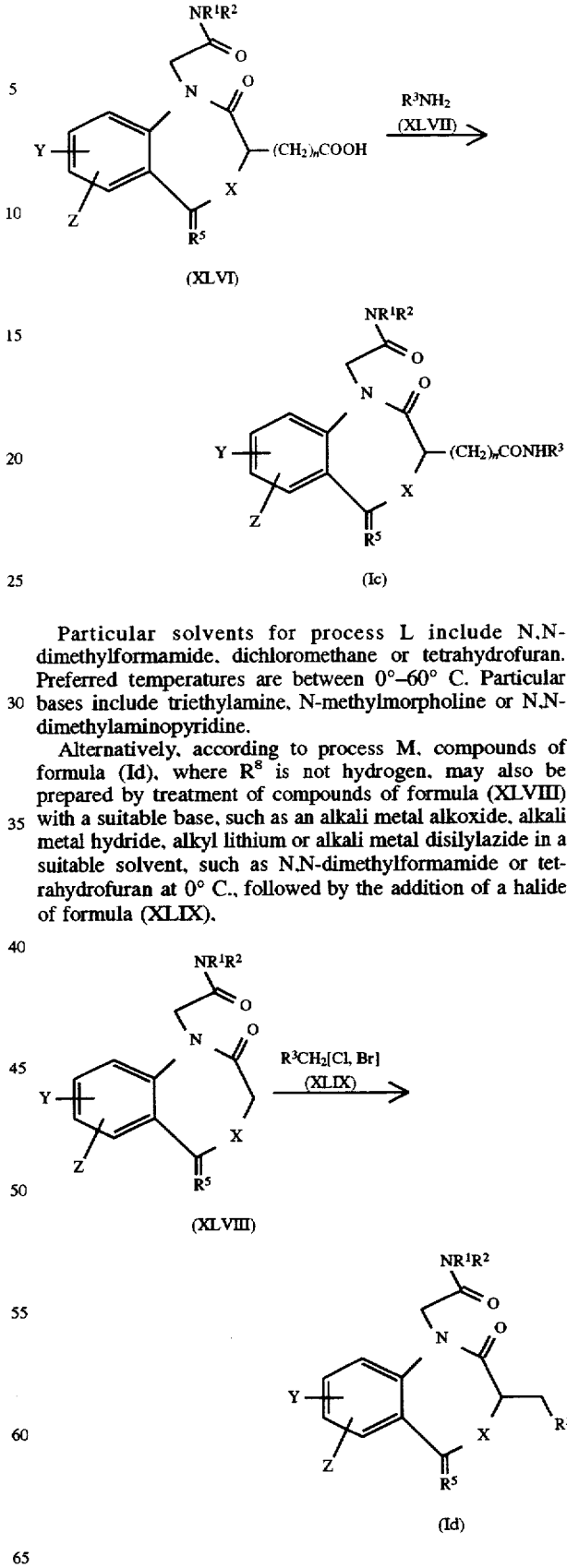

According to process N, compounds contained within formula (Ie) may be prepared by the reaction of isatoic anhydride derivatives (L) with substituted amino acids of formula (LI).

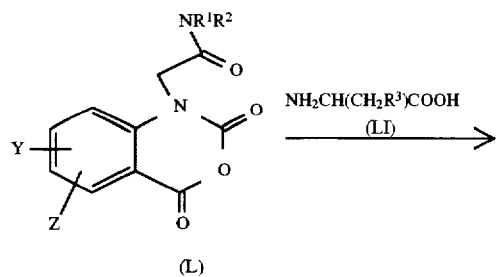

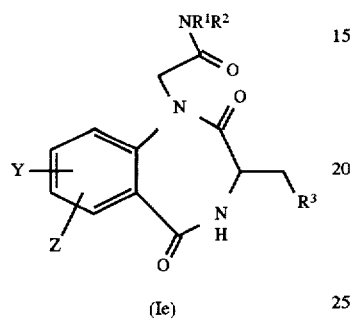

The reaction is conveniently run in water or aqueous alcohol, with a suitable base such as triethylamine or sodium carbonate at temperatures ranging from 25°–50° C.

According to process O, certain compounds of formula (LII) (contained within formula (I)) may be further converted to compounds within the definition of formula (If) by treatment with a suitable base such as an alkali metal alkoxide, alkali metal hydride, alkyl lithium or alkali metal disilylazide in a suitable solvent, such as N,N-dimethylformamide or tetrahydrofuran at 0° C., followed by the addition of a halide of formula (LIII).

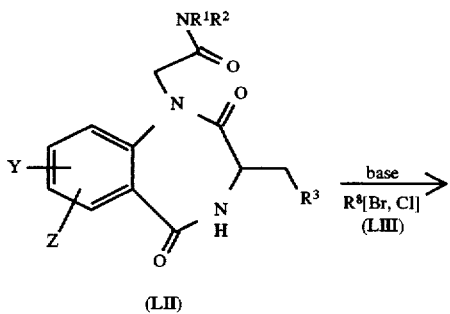

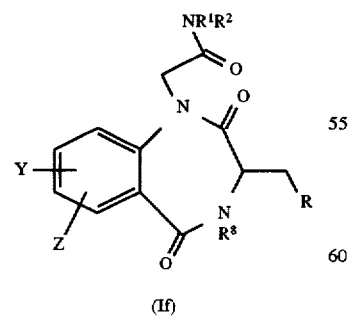

According to process P, certain compounds of formula (LII) (contained within formula (I)) may be further coverted to compounds within the definition of formula (Ig) wherein $R^{11}$ is a heteroaryl substituent by treatment with phosphorus oxychloride, followed by reaction with a hydrazone of formula (LIV). Preferred solvents include dichloromethane or chloroform. Preferred temperatures are from 0° C. to the reflux temperature of the solvent.

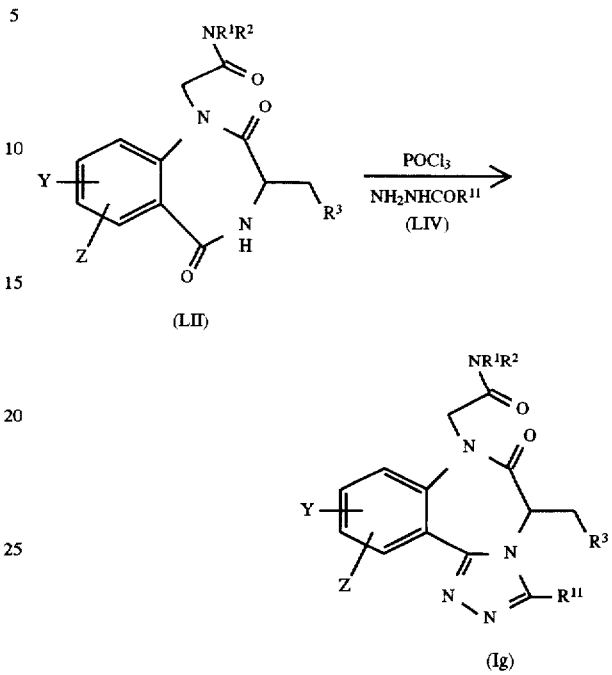

Intermediates for formula (XLIV) are prepared by treatment of a compound of formula (XLVIII), with an appropriate base, such as an alkali metal alkoxide, alkali metal hydride, alkyl lithium or alkali metal disilylazide in a suitable solvent, such as N,N-dimethylformamide or tetrahydrofuran at 0° C., followed by the addition of bis (triisopropyl) phenylsulfonyl azide. The 3-azido compound

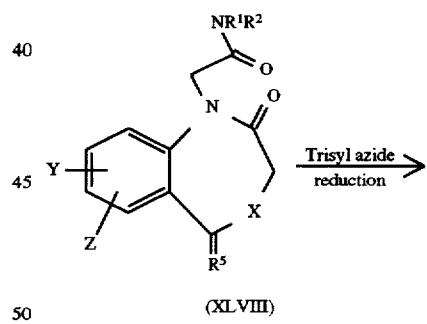

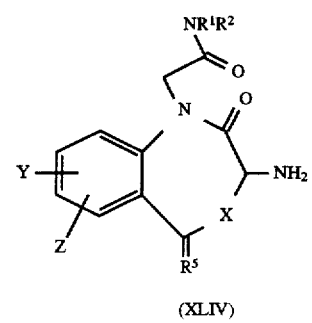

may be reduced to the amine by treatment with stannous chloride or triphenylphosphine, or by catalytic reduction using Pd/C. Appropriate solvents for the reduction include methanol, ethanol, ethyl acetate, or tetrahydrofuran.

Intermediates of formula (XLVIa) are prepared by treatment of a compound of formula (XLVIII), where $R^8$ is not hydrogen, with an appropriate base, such as an alkali metal alkoxide,

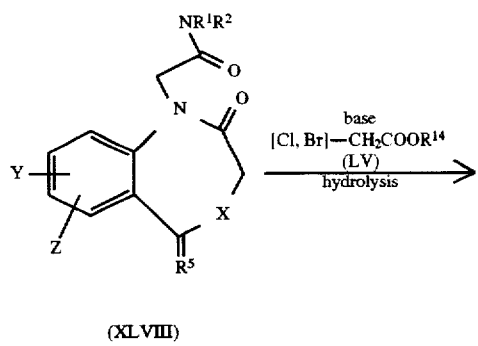

(XLVIII)

[Cl, Br]—$CH_2COOR^{14}$
(LV)
base
hydrolysis
→

(XLVIa)

alkali metal hydride, alkyl lithium or alkali metal disilylazide in a suitable solvent, such as N,N-dimethylformamide or tetrahydrofuran at 0° C., followed by the addition of a haloacetate of formula (LV), where $R^{14}$ is benzyl or $C_{1-4}$alkyl. The ester protecting group is removed under appropriate conditions.

Intermediates of formula (XLVIa) may also be prepared directly from the reaction of isatoic anyhydride derivative (L) with suitably protected L- or D-aspartic or glutamic acid of formula (LVI), followed by removal of the ester protecting group.

(L)

$COOR^{14}$
|
$(CH_2)n$
|
$H_2N$ — COOH
(LVI)
hydrolysis
→

(XLVIa)

The condensation reaction is conveniently run in water or aqueous alcohol, with a suitable base such as triethylamine or sodium carbonate at temperatures ranging from 25°–50° C.

Intermediates of formula (LVIII) may be prepared by the reaction of compounds of formula (LVII) with an appropriate base, such as an alkali metal (LVII)

base
$R^8[Br, Cl]$
→

(LVIII)

alkoxide, alkali metal hydride, alkyl lithium or alkali metal disilylazide in a suitable solvent, such as N,N-dimethylformamide or tetrahydrofuran at 0° C., followed by the addition of a halide of formula (LIII).

Alternatively, intermediates of formula (LIX) wherein $R^{11}$ is a heteroaryl substituent may prepared from compounds of formula (LVII) by treatment with phosphorus oxychloride, followed by reaction with hydrazones of formula (LIV).

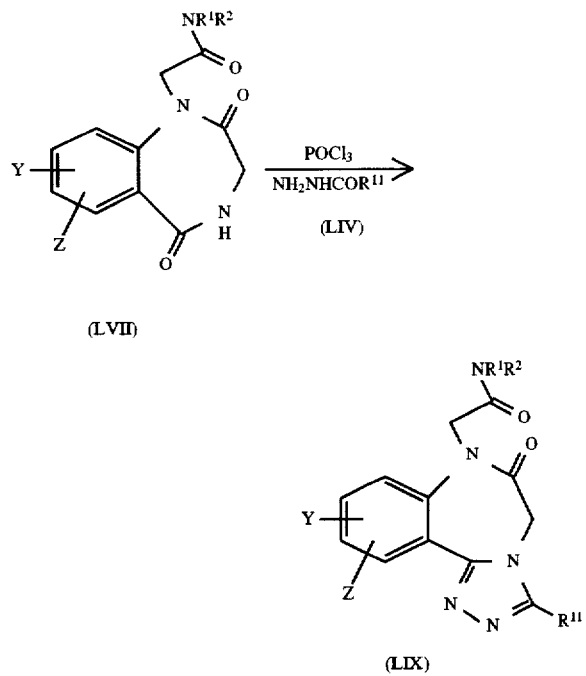

(LVII)

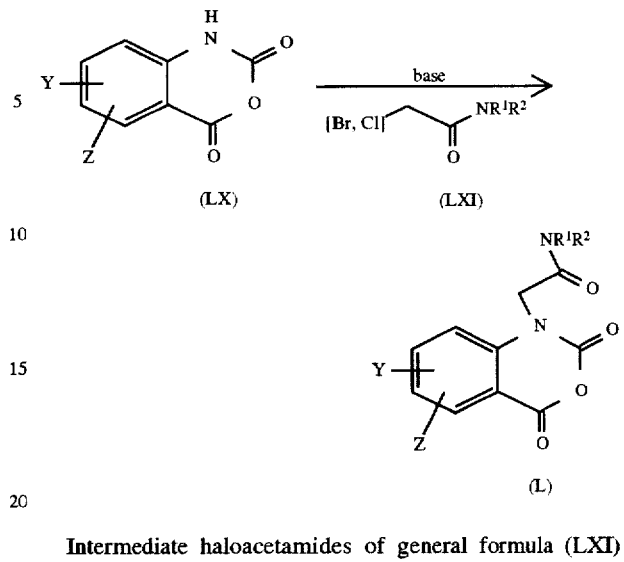

Intermediate haloacetamides of general formula (LXI) may be prepared by the reaction of amines of formula $$HNR^1R^2 \qquad (XIV)$$

with bromoacetyl bromide, chloroacetyl chloride or bromoacetyl chloride in an aprotic solvent such as dichloromethane, tetrahydrofuran, diethyl ether or acetonitrile at 0° C., in the presence of a tertiary amine base, such as triethylamine.

Amines of formula (XIV) are obtained as described above.

(LIX)

Intermediates of formula (LVII) are prepared from the condensation of isatoic anhydride derivatives of formula (L) with glycine. The condensation reaction is

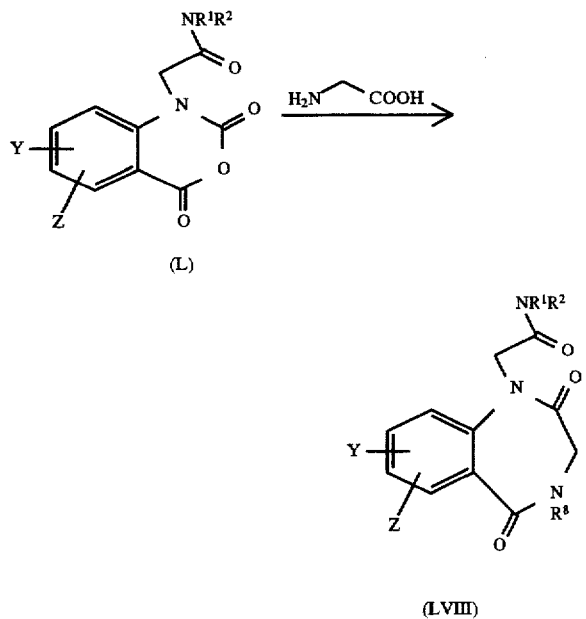

(LVIII)

conveniently run in water or aqueous alcohol, with a suitable base such as triethylamine or sodium carbonate at temperatures ranging from 25°–50° C.

Intermediates of formula (L) are prepared by treatment of isatoic anhydride of formula (LX) with an appropriate base, such as an alkali metal carbonate, alkali metal hydroxide, alkali metal alkoxide, alkali metal hydride, alkyl lithium or alkali metal disilylazide in a suitable solvent, such as N,N-dimethylformamide or tetrahydrofuran at 0° C., followed by the addition of a haloacetamide of formula (LXI).

Pharmacology

The efficacy of compounds of the present invention in binding CCK-A and CCK-B and as agonists of CCK-A can be evaluated and measured using pharmacological methods known in the art or as described in detail below based on similarly established methodologies.

1. CCK-A RECEPTOR BINDING ASSAY

Tissue Preparation

Solutions of 0.3M sucrose and 2.0M sucrose are prepared and chilled overnight at 4° C. On the following day and prior to use, inhibitors are added such that the final concentrations are 0.01% Soybean Trypsin Inhibitor (50 mg/500 ml sucrose) and 100 µM phenylmethysulfonyl fluoride (8.5 mg/500 mL sucrose).

Rats are sacrificed by decapitation using a guillotine. The rat's external abdominal wall is wetted with methanol and fur and skin are removed. The abdomen is opened, the pancreas is carefully dissected out and placed in a 50 mL beaker containing 0.3M sucrose. After all the pancreata are harvested, excess fat and lymph nodes are trimmed off. Pancreatic tissue is divided into approximately 4.0 g aliquots into 30 mL beakers, each containing 1.0 mL of 0.3M sucrose.

In 4° C. cold room, the pancreata are minced with scissors and diluted 1:10 weight:volume with 0.3M sucrose. Aliquots are homogenized in a chilled 40 mL Wheaton dounce with 4 up and down strokes of the "B" pestle followed by 4 up and down strokes of the "A" pestle. Homogenates are filtered through 2 layers of cheesecloth into a chilled 500 mL beaker, then diluted with 2.0M sucrose with stirring to yield a final concentration of 1.3M sucrose homogenate. The resulting 1.3M homogenate is dispensed into 18 thin-walled 36 mL polyallomer tubes on ice (approximately 30 mL homogenate per tube) and each tube is subsequently overlaid with 0.3M sucrose until liquid is approximately 0.5 cm from the top of the tube. The samples are spun in a Sorvall RC70 ultracentrifuge at 27,500 RPM (100,000×g) for 3 hours at 4° C. The interface band is collected into a chilled graduated cylinder, diluted and mixed with cold distilled water to a total volume of 312 mL and spun at 100,000×g for 50 min. at 4° C. The pellets are resuspended in KRH buffer (25 mM HEPES, 104 mM NaCl, 5 mM KCl, 1 mM KPO$_4$, 1.2 mM MgSO$_4$, 2 mM CaCl$_2$, 2.5 mM Glucose, 0.2% BSA, 0.1 mM PMSF, 0.01% STI, pH 7.4 at 4° C.), transferred to a 15 mL Wheaton dounce and homogenized with 4 up and down strokes of the matched "A" (tight) pestle. This homogenate is transferred into 2–27 mL polycarbonate bottles and spun at 100,000×g for 30 min. at 4° C. The pellet is resuspended (1 mL KRH buffer/gm wt of original tissue), transferred to an appropriate size dounce and homogenized with 4 up and down strokes of the matched "A" pestle. 1 mL aliquots are stored at −70° C. in microcentrifuge tubes.

Assay

Test compounds are diluted in 10×Assay Binding Buffer (200 mM HEPES, 10 mM EGTA, 1.8M NaCl, 50 mM KCL, 50 mM MgCl$_2$, 0.5% BSA, pH 7.4).

50 μL compound+400 μL Assay Binding Buffer+25 μL [$^{125}$I] sulphated CCK-8 labeled with Bolton and Hunter reagent (Amersham, 2000 Ci/mmol)+25 μL prepared rat pancreas membranes are incubated for 30 minutes at 25° C. while shaking gently throughout the incubation.

1 μM L-364718 (final concentration) is used for determination of non-specific binding.

Reaction is stopped using Brandell Cell Harvester, washing 3× with 3 mL ice-cold (4° C.) assay binding buffer per ish.

Tissues are collected on Whatman GF/B filter papers pre-wet with assay buffer and filter papers counted using a gamma counter.

2. CCK-B RECEPTOR BINDING ASSAY

Tissue Preparation

Hartley Male Guinea Pigs (250–300 g. Charles River) are sacrificed by decapitation. The brain is removed and placed in 4° C. Buffer (50 mM Tris/HCL, pH 7.4). The cortex is dissected and placed in 4° C. Buffer. The total wet weight of all cortices is determined and the tissues are diluted 1:10 (wt:vol) with Buffer.

The cortex is minced using a Tekmar Tissuemizer then homogenized in Buffer with 5 up and down strokes using a motor driven glass/teflon homogenizer. The preparation is maintained at 4° C. (on ice).

Membranes are pelleted by centrifugation in Sorvall RC5C at 4° C. using a SA 600 rotor spun at 16,000 RPM (47,800×g Maximum). The pellet is saved and the supernatent is discarded. The pellets are combined and resuspended in Buffer at 4° C. using same volume as above and blended as above with 5 up and down strokes of a glass/teflon motor driven homogenizer using the same volume as before. The resulting homogenates are spun at 16,000 RPM (47,800×g Maximum, 36,592×g Average) for 15 minutes at 4° C. Pellets are saved and the supernatents discarded. Pellets are subsequently combined with Buffer to get a final volume of 300 mL and blended using a Tekmar Tissuemizer. Initial protein content is determined by the Biorad protein assay. The volume of suspension is adjusted with buffer, such that the volume adjustment yielded approximately 4.0 mg/mL as a final concentration, confirmed via the Biorad protein assay. The final suspension is transferred as 4.0 mL aliquots into plastic tubes and frozen at −70° C.

Assay

Skatron filters are soaked in Buffer with 0.1% Bovine Serum Albumin (BSA) for an hour prior to harvesting.

Test compounds are diluted in 10×Assay Binding Buffer (200 mM HEPES, 10 mM EGTA, 1.8M NaCl, 50 mM KCL, 50 mM MgCl$_2$, 0.5% BSA, pH 7.4). [$^{125}$I]-sulfated CCK-8 labeled with Bolton-Hunter reagent (Amersham, 200 Ci/mmol) is diluted.

25 μL 100 μM Bestatin+25 μL 3 μM Phosphoramidon+25 μL test compound+50 μL radioligand+25 μL 10×Assay Binding Buffer+100 μL guinea pig cortex membranes are incubated 150 minutes at room temperature.

For B$_0$ determination, Assay Binding Buffer is substituted for test compound.

For filter binding determination, Assay Binding Buffer is substituted for test compound and guinea pig cortex membranes.

For non-specific binding determination, 1 μM sulphated CCK-8 (Sigma) is substituted for test compound.

Reaction is stopped by filtering using the automated Skatron Cell Harvester. The filters are rinsed using 4° C. Assay Binding Buffer. The filters are subsequently punched, placed in tubes and counted using a gamma counter.

3. GUINEA PIG GALL BLADDER ASSAY

Tissue Preparation

Gallbladders are removed from guinea pigs sacrificed by cervical dislocation. The isolated gallbladders are cleaned of adherent connective tissue and cut into two rings from each animal (2–6 mm in length). The rings are subsequently suspended in organ chambers containing a physiological salt solution (118.4 mM NaCl, 4.7 mM KCl, 1.2 mM MgSO$_4$, 2.5 mM CaCl$_2$, 1.2 mM KH$_2$PO$_3$, 25 mM NaHCO$_3$, 11.1 mM dextrose). The bathing solution is maintained at 37° C. and aerated with 95% O$_2$/5% CO$_2$. Tissues are connected via gold chains and stainless steel mounting wires to isometric force displacement transducers (Grass, Model FT03 D). Responses are then recorded on a polygraph (Grass, Model 7E). One tissue from each animal served as a time/solvent control and did not receive test compound.

Assay

Rings are gradually stretched (over a 120 min. period) to a basal resting tension of 1 gm which is maintained throughout the experiment. During the basal tension adjustment period, the rings are exposed to acetylcholine (10$^{-6}$M) four times to verify tissue contractility. The tissues are then exposed to a submaximal dose of sulfated CCK-8 (Sigma, 3×10$^{-9}$M). After obtaining a stable response, the tissues are washed out 3 times rapidly and every 5 to 10 minutes for 1 hour to reestablish a stable baseline.

Compounds are dissolved in dimethylsulfoxide (DMSO) then diluted with water and assayed via a cumulative concentration-response curve to test compound (10$^{-11}$ to 3×10$^{-6}$M) followed by a concentration-response curve to sulfated CCK-8 (10$^{-10}$ to 10$^{-6}$M) in the presence of the highest dose of the test compound. As a final test, ACH (10 μM) is added to induce maximal contraction. A minimum of three determinations of activity are made for each test compound.

4. 18-HOUR DEPRIVATION-INDUCED FEEDING PARADIGM

Male, Long-Evans rats (Charles River Co., Raleigh, N.C.), weighing 300–375 grams, are acclimated individually for at least a week in hanging, stainless steel mesh cages (17.8×25.4×17.8 cm high) with ad libitum access to water (delivered through automatic drinking spouts at the rear of the cage) and food (Lab Blox, Purina Rodent Laboratory Chow #5001) on a 12-hour light/dark cycle (lights on from 0600–1800 hours, or h) at approximately 22.8° C. Prior to testing, all chow, but not water, is removed at 1600 h. At 0900 h the next morning, rats are weighed. At 0945 h, rats are injected intraperitoneally (i.p.), orally (per os, or p.o.) or through an indwelling, intraduodenal cannulea with a test compound or vehicle (2 mL/kg) and returned to their home cages. Food is presented at 1000 h. At 1030 h, remaining food and spillage is weighed.

5. MEASUREMENT OF ACID SECRETION IN GASTRIC FISTULA RAT

Gastric fistula rats are prepared according to the methods described by Dimaline, Carter and Barnes (Am. J. Physiol., 251, G615-G618 (1986). Female AH/A rats (200 g) are anaesthetized using a mixture of nitrous oxide, isoflurane and oxygen gas to allow the implantation of a gastric fistula. The abdomen is opened with a midline incision and the stomach exteriorised. A small incision is made in the fundic region of the stomach, along the greater curvature, and the stomach washed clean with 0.9% saline. A titanium cannula is inserted part way into the incision and tied in place with 2/O gauge suture thread. The cannula is then exteriorised through a stab wound lateral to them midline incision and secured by stitching to the abdominal wall. The midline incision is sutured and the cannula closed with a screw cap to prevent food loss. The rats are then allowed 1 week recovery period before use in secretion experiments. Animals are housed individually in solid bottomed cages containing wood chippings and allowed free access to food and water, in a room with 12 hour light/dark cycle.

18 hours prior to the experiment, rats are placed in grid bottomed cages to prevent coprophagy. Food is removed but the animals are allowed free access to water. At the start of the experiment, each rat is anaesthetized with a mixture of isoflurane, nitrous oxide and oxygen gas and the stomachs washed with 0.9% saline via cannula to remove any remaining food. At the same time, a tail vein cannula is inserted pericutaneously to provide a route for intravenous administration. The rats are then left to recover from the anesthetic in Boliman type restraint cages for the duration of the experiment.

After a 60 minute acclimatization period, gastric secretion is collected every 15 minutes by drainage into pre-weighed pots. During the acclimatization period, a saline infusion (3.5 ml/hour) is given via the tail vein to keep the tubing free from blood clotting and to maintain hydration of the rat.

Collected samples are weighed and the volume of secretions determined. The gastric acid concentration of each 15 minute collection is determined by titration to pH 7.0 with 0.1M NaOH using radiometer auitotitrator equipment, and the total acid secreted per 15 minute period calculated.

Acid secretion is stimulated using a submaximal infusion of pentagastrin (0.6 µgkg$^{-1}$h$^{-1}$). Once a stable plateau to acid secretion is achieved, test compounds are administered intravenously and acid secretion recorded for a further 180 minutes. Inhibition of acid secretion is expressed as percentage inhibition of pre-test compound secretion levels.

6. MEASUREMENT OF ACID SECRETION IN HEIDENHAIN POUND DOG

Male beagle dogs (10–15 kg) are prepared with a Heidenhain pound by a veterinary surgeon according to the methods described by Emas, Swan and Jacobsen (Methods of Studying Gastric Secretion, Chapter 42, pp. 749–751, Handbook of Physiology, Section 6, Alimentary Canal. Ed: Code CF. Pub: American Physiology Society). Animals are allowed 4 weeks to recover from surgery prior to experimental use. For measurement of acid secretion, dogs are starved overnight, with water ad libitum. Gastric juice is collected from the Heidenhain pouch at 15 min. intervals and total acid output determined by automatic titration to pH 7.0 with 0.1M NaOH. Acid secretion is stimulated using a submaximal intravenous infusion of pentagastrin (1 µg/kg$^{-1}$min$^{1}$). Once a stable plateau increase in acid secretion is achieved, test compounds are administered by bolus intravenously. Acid secretion is recorded every 15 min. for a further 180 min. Inhibition of acid secretion is expressed as percentage inhibition of plateau acid secretion values.

7. RAT GASTRIC EMPTYING PROTOCOL

Methyl Cellulose (MC) Test Meal
1. Disperse MC in water at 80° C. at a final concentration of 1.5% under continuous stirring. Cool to room temperature.
2. Add Phenol Red (50 mg/100) to solution.
3. Keep solution stirring during entire experiment.

Drug Administration
1. Food deprive animals for 18 hours.
2. Inject test drug/prop. glycol or prop. glycol alone intraperitoneally.
3. After 5 minutes, gavage 1.5 mL of Pheno Red/MC solution Processing Stomachs
1. After 20 minutes, decapitate animal
2. Clamp stomach at the pylorus and cardia ends, and rinse in 0.9% NaCl.
3. Place stomach in 100 mL of 0.1N NaOH, cut into small pieces, and homogenize for 30 seconds.
4. Let settle at room temperature for 60 minutes.
5. In centrifuge tube, add 5 mL of supernatant and 0.5 mL of trichloroacetic acid (29% w/v), and centrifuge at 2.800 rpm for 20 minutes.
6. Decant supernatant, and add 4 mL of 0.5N NaOH and read absorbance at a wavelength of 560 nm.

Calculations

Percent gastric emptying =

$$1 - \frac{(\text{amount of phenol red recovered from test stomach} \times 100)}{\text{average amount of phenol red recovered from standard stomachs}}$$

The standard stomach is determined from the phenol red recovered in stomachs of rats decapitated immediately after intragastric infusion of MC/phenol red.

TABLE 1

Functional activity in isolated guinea pig gallbladder preparation, expressed as % CCK-induced maximal response.

| Example | % Contraction (30 µM) | % Contraction (1 µM) |
|---|---|---|
| 1 | 63 | |
| 2 | 88 | |
| 3 | 38 | |
| 4 | 59 | 23 |
| 5 | 82 | |
| 6 | | 41 |
| 7 | 61 | 16 |
| 8 | 86 | 59 |
| 9 | 62 | 73 |
| 10 | | 54 |
| 11 | 43 | 56 |

TABLE 1-continued

Functional activity in isolated guinea pig gallbladder preparation, expressed as % CCK-induced maximal response.

| Example | % Contraction (30 μM) | % Contraction (1 μM) |
|---------|------------------------|----------------------|
| 12 | 80 | |
| 13 | 77 | |
| 14 | 13 | |
| 15 | 52 | |
| 16 | 67 | |
| 17 | | 24 |
| 18 | | 75 |
| 19 | 58 | 83 |
| 20 | | 31 |
| 21 | | 54 |
| 22 | | 36 |
| 23 | | 36 |
| 24 | 79 | 93 |

TABLE 2

Functional activity of compounds in CCK-A agonist isolated guinea pig gallbladder preparation assay and in gastric emptying assay.

| | Isolated guinea pig gallbladder: % contraction | rat gastric emptying: % emptying |
|---|---|---|
| Vehicle$^A$ | — | 66 |
| CCK-8$^B$ | 100 | 0 |
| CCK-8 and CCK-A antagonist$^C$ | — | 52 |
| CCK-8 and CCK-B antagonist$^D$ | — | 0 |
| CCK-A agonist 1$^E$ | 87 | 6 |
| CCK-A agonist 2$^F$ | 100 | 2.5 |

$^A$0.5% methyl cellulose was used as a test vehicle in the gastric emptying assay.
$^B$CCK-8 is the C-terminal octapeptide of CCK, delivered at 1 μM in the gallbladder assay, administered intraperitoneally at 30 nmoles/kg in the gastric emptying assay.
$^C$CCK-A antagonist is MK-329, see Evans, B. E., et al, Proc. Nat. Acad. Sci. (83), 4918–1922 (1986), administered intraperitoneally at .5 μmoles/kg in the gastric emptying assay.
$^D$CCK-B antagonist is L-365,260, see Bock, M. G. et al, J. Med. Chem., (32), 16–23 (1989), administered intraperitoneally at .5 μmoles/kg in the gastric emptying assay.
$^E$CCK-A agonist 1 is 2-[3-(1H-Indazol-3-ylmethyl)-2,4-dioxo-5-phenyl-2,3,4,5-tetrahydro-benzo[b][1,4]diazepin-1-yl]-N-isopropyl-N-(4-methoxyphenyl) acetamide, delivered at 30 μM in the gallbladder assay, administered intraperitoneally at 0.1 μmoles/kg in the gastric emptying assay.
$^F$CCK-A Agonist 2 is 2-[3-(1H-Indazol-3-ylmethyl)-2,4-dioxo-5-(2-pyridinyl)-2,3,4,5-tetrahydro-benzo[b][1,4]diazepin-1-yl]-N-isopropyl-N-(4-methoxyphenyl) acetamide, delivered at 30 μM in the gallbladder assay, administered intraperitoneally at 0.1 μmoles/kg in the gastric emptying assay.

While it is possible that, for use in therapy, a compound of the invention may be administered as the raw chemical it is possible to present the active ingredient as a pharmaceutical formulation. The invention thus further provides a pharmaceutical formulation comprising a compound of formula (I) or a physiologically acceptable salt or solvate thereof together with one or more pharmaceutically acceptable carriers or excipients. The carrier(s) or excipient(s) must be acceptable in the sense of being compatable with the other ingredients of the formulation and not deleterious to the recipient thereof. According to another aspect of the invention, there is provided a process for the preparation of a pharmaceutical formulation comprising admixing a compound of formula (I) or a pharmaceutically acceptable salt or solvate thereof with one or more pharmaceutically acceptable carriers or excipients.

Compounds of formula (I) and physiologically acceptable salts and solvates thereof may be formulated for administration by any route, and the appropriate route will depend on the disease being treated. Suitable pharmaceutical formulations include those for oral, rectal, nasal, topical, (including buccal and sublingual), vaginal or parental (including intramuscular, sub-cutaneous, intravenous, and directly into the affected joint) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets, or tablets each containing a predetermined amount of the active ingredient; as a powder or granules; as a solution, a suspension or as an emulsion. The active ingredient may also be presented as a bolus, electuary, or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups, or elixirs, or may be presented as a dry product for constitution with water of other suitable vehicle before use. Such liquid preparations may contain conventional additives such as suspending agents, non-aqueous vehicles (which may include edible oils), or preservatives.

Oral formulations in solid dosage forms such as tablets and capsules for treatment of obesity and its related conditions, for treatment of diabetes and related conditions, for improving gastrointestinal motility, modifying pancreatic enzyme secretions, inducing gallbladder contraction, modifying food intake, inducing satiety and reducing anxiety should be suitable for non-disintegration in the stomach with rapid disintegration in the intestine, i.e. an enteric coating. Examples of enteric coatings utilizing pH dependence for solubility include cellulose acetate phthalate, polyvinyl acetate phthalate, hydroxypropyl methylcellulose phthalate and methacrylic acid copolymer. Some of these coating agents may require a plasticizer such as triethyl citrate, polyethylene glycol or triacetin.

Oral formulations for treatment of diabetes and related conditions may be suitable for disintegration prior to leaving the stomach, having no coating or an immediate release coating, such as hydroxypropyl methylcellulose or sucrose possibly including plasticizers.

Enteric and immediate release coatings may also contain materials to make them opaque such as titanium dioxide, dyes to color, or talc to make less tacky. The coatings are typically applied as a solution or dispersion in either organic or aqueous media. On a production scale, both types coating are typically applied by spraying it onto the dosage form using a coating pan or a fluid bed coater.

The compounds according to the invention may also be formulated for parental administration (e.g. by injection, for example bolus injection or continuous infusion) and may be presented in unit dose form in ampules, pre-filled syringes, small volume in fusion or in multi-dose containers with an added preservative. The compositions may take such forms as suspensions, solutions, or emulsions in oily or aqueous vehicles, and may contain formulatory agents such as suspending, stabilizing, and/or dispersing a gents. Alternatively, the active ingredient may be in powder form, obtained by asceptic isolation of sterile solid or by lyophilization from solution, for constitution with a suitable vehicle, e.g. sterile, pyrogen free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthishes comprising the active ingredient in a suitable liquid carrier. For topical administration to the eye, the compounds according to the invention may be made up in a solution or suspension in a suitable sterile aqueous or non-aqueous vehicle. Additives such as buffers (e.g. sodium metabisulphite or disodium edeate) and thickening agents such as hypromellose may also be included.

Pharmaceutical formulations suitable for rectal administration wherein the carrier is a solid are possibly presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams, or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one or more dispersing agents, solubilizing agents, or suspending agents. Liquid sprays are conveniently delivered from pressurized packs.

For administration by inhalation the compounds according to the invention are conveniently delivered from an insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin of blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example antiinfective agents such as bactericidal or fugicidal agents, antiinflammatory agents or anticancer agents.

The invention thus provides, in a further aspect, a combination comprising a compound of formula (I) or a physiologically acceptable derivative thereof together with another therapeutically active agent, in particular a bactericidal or fugicidal agent, an antiinflammatory agent or an anticancer agent.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. Suitable therapeutic agents for use in such combinations include tetracyclin and appropriate nonsteroid and steroid antiinflammatory drugs and anticancer agents. The individual components of such combinations may be administered either sequentially or simultaneously in separate or combined pharmaceutical formulations. Appropriate doses of known therapeutic agents will be readily appreciated by those skilled in the art.

The amount of a compound of the invention required for use in treatment will of course vary not only with the particular compound selected but also with the route of administration, the nature of the condition being treated and the age and condition of the patient and will be ultimately at the discretion of the attendant physician or veterinarian. In general, however, a suitable dose will be in the range of from about 0.1 to 300 mg/kg of bodyweight per day, particularly from about 1 to 100 mg/kg of bodyweight per day. An appropriate dosage unit involved in oral administration may generally contain from about 1 to 250 mg, particularly from about 25 to 250 mg, of a compound of formula (I). The dosage employed for the topical administration will, of course, depend on the size of the area being treated. For the eyes each dose will be typically in the range of from 10 to 100 mg of the compound of formula (I).

For use in the treatment of CCK related disorders the compounds of the invention can be administered by any of the aforementioned routes, particularly by the oral route or by injection. The daily non-toxic dosage for a 70 kg mammal will be in the range of about 10 mg to 5 g of a compound of formula (I).

EXAMPLES

The following examples illustrate aspects of this invention but should not be construed as limitations thereto.

|  | Pharmacy Example A |
|---|---|
| Active Ingredient: | 50 mg |
| Lactose anhydrous USP: | 163 mg |
| Microcrystalline Cellulose NF: | 69 mg |
| Pregelatinized starch Ph. Eur. | 15 mg |
| Magnesium stearate USP | 3 mg |
| Compression weight: | 300 mg |

The active ingredient, microcrystaline cellulose, lactose and preglelatinized starch are sieved through a 500 micron sieve and blended in a suitable mixer. The magnesium stearate is sieved through a 250 micron sieve and blended with the active blend. The blend is compressed into tablets using suitable punches, then coated with cellulose acetate phthalate.

Intermediate 1

N-Isopropyl-N',N'-dimethyl-benzene-1,4-diamine

Acetone (30 mL, 408 mmol) is added to a mixture of N',N'-dimethyl-benzene-1,4-diamine (27.2 g, 200 mmol), acetic acid (glacial, 13.8 mL, 241 mmol), methanol (500 mL), and sodium cyanoborohydride in THF (1M, 440 mL, 440 mmol) and allowed to stir overnight under nitrogen. After concentrating in vacuo to a residue, the reaction mixture is partitioned between ethyl acetate and aqueous sodium carbonate. The layers are separated and the aqueous layer is extracted twice with ethyl acetate. The organic layers are combined, extracted with saturated brine, dried over anhydrous potassium carbonate, and concentrated in vacuo to afford the title compound as an oil (38.0 g, 213 mmol) of sufficient purity for the next step. $^1$H NMR (300 MHz, CDCl$_3$) δ=1.18 (d, J=6.28 Hz, 6H); 2.82 (s, 6H); 3.04 (b, 1H), 3.47–3.59 (m, 1H); 6.59 (d, J=9.0 Hz, 2H); 6.73 (d, J=9.0 Hz, 2H). TLC R$_f$=0.3 (20:80 ethyl acetate: n-hexane).

Intermediate 2

Isopropyl-(4-methoxy-phenyl)-amine

By employing conditions similar to those described in Intermediate 1, 4-anisidine (1.27 g, 20.6 mmol) is converted to the title compound, which is obtained as an oil (1.72 g, 10.42 mmol) and used without further purification. $^1$H NMR (300 MHz, CDCl$_3$) δ=1.18 (d, J=6.4 Hz, 6H); 3.49–3.58 (m, 1H); 3.74 (s, 3H); 6.59 (d, J=9.1 Hz, 2H); 6.78 (d, J=6.6 Hz, 2H). TLC R$_f$=0.7 (2:3 ethyl acetate: n-hexane).

Intermediate 3

2-Bromo-N-isopropyl-N-phenyl-acetamide

Isopropyl aniline (8.00 g, 59.2 mmol) and triethylamine (8.26 mL, 59.2 mmol) are combined in anhydrousDCM (75 mL) under nitrogen and cooled to 0°–5° C. with an ice-water bath. Bromoacetyl bromide (5.16 mL, 59.2 mmol) is added dropwise over approximately 10 min. and the reaction is allowed to stir to ambient temperature overnight. The mixture is combined with aqueous HCl (50 mL 1N) and transferred to a separatory funnel. The organic layer is separated, dried over anhydrous magnesium sulfate, filtered and concentrated in vacuo to provide the title compound as a brown solid (15.13 g, 59.1 mmol). $^1$H NMR (300 MHz, CDCl$_3$) δ=1.08 (d, J=6.8 Hz, 6H); 3.53 (s, 2H); 4.92–5.01 (m, 1H); 7.18–7.54 (m, 5H). TLC Rf=0.22 (3:17 ethyl acetate: hexane).

Intermediate 4

2-Bromo-N-(4-dimethylamino-phenyl)-N-isopropyl-acetamide

By employing conditions similar to those described in Intermediate 3, N-isopropyl-N',N'-dimethyl-benzene-1,4-diamine (6.57 g, 36.8 mmol), prepared as in Intermediate 1, is converted to the title compound, which is obtained as a green solid (9.02 g, 30.2 mmol). $^1$H NMR (300 MHz, CDCl$_3$) δ=1.03 (d, J=6.6 Hz, 6H); 3.00 (s, 6H); 3.56 (s, 2H); 4.88–6.94 (m, 1H); 6.71 (d, J=6.4 Hz, 2H); 7.00 (d, J=8.8 Hz, 2H). TLC Rf=0.7 (1:2 ethyl acetate: n-hexane).

Intermediate 5

2-Bromo-N-isopropyl-N-(4-methoxy-phenyl)-acetamide

By employing conditions similar to those described in Intermediate 3, isopropyl-(4-methoxy-phenyl)-amine (1.72 g, 10.42 mmol), prepared as in Intermediate2, is converted to the title compound, which is obtained as a brown solid (0.777 g, 2.73 mmol). $^1$H NMR (300 MHz, CDCl$_3$) δ=1.04 (d, J=6.8 Hz, 6H); 3.53 (s, 2H); 3.84 (s, 3H); 4.85–5.01 (m, 1H); 6.92 (d, J=8.5 Hz, 2H); 7.10 (d, J=8.9 Hz, 2H). TLC R$_f$=0.4 (3:17 ethyl acetate: hexane).

Intermediate 6

3-[(benzyloxycarbonyl)amino]-5-phenyl-1,3-dihydro-benzo[e][1,4]diazepin-2-one A solution of 2-(benzotriazol-1-yl)-N-benzyloxycarbonyl-glycine (Katritzky et al. 1989 *J. Chem. Soc., Chem Comm.* 337; 10.00 g; 30.7 mmol) in anhydrous THF (100 mL) under nitrogen is cooled to 0°–5° C. with an ice-water bath. Oxalyl choride (2M in DCM, 15.3 mL, 30.7 mmol) is added via syringe followed by anyhydrous DMF (0.25 mL). After maintaining the reaction mixture at 0°–5° C. for 2 hrs., a solution of 2-amino-benzophenone (5.445 g, 27.61 mmol) and anhydrous N-methyl-morpholine (5.90 mL, 61.4 mmol) in anhydrous THF (30 mL) is added dropwise over approximately 20 min. The reaction is allowed to warm to ambient temperature and the slurry is filtered. The residual solids are washed with a minimum quantity of anhydrous THF (approximately 25 mL) and the washings are combined with the mother liquor. The mother liquor is saturated with ammonia gas, diluted with methanol (150 mL), and saturated again with ammonia gas over approximately 0.5 hrs. The reaction mixture is evaporated in vacuo, dissolved in ethyl acetate and then concentrated again in vacuo. The residue is dissolved in ethyl acetate and washed twice with aqueous sodium hydroxide (1N). The combined aqueous layers are extracted with ethyl acetate and the organic layers are combined, extracted with saturated aqueous brine, dried over anhydrous sodium sulfate and concentrated in vacuo.

The crude intermediate (12.6 g) is dissolved in glacial acetic acid (200 mL), combined under nitrogen with ammonium acetate (10.00 g, 129.7 mmol) and allowed to stir at ambient temperature overnight. The reaction mixture is concentrated in vacuo and suspended in ethyl acetate (50 mL) and diethyl ether (150 mL). Aqueous sodium hydroxide (1N) is added until the pH of the aqueous layer is greater than 8. The resulting slurry is cooled to 0°–5° C. with an ice-water bath, filtered, washed with water and diethyl ether, and dried under high vacuum to provide the title compound as a crystalline solid (7.77 g, 20.2 mmol). $^1$H NMR (300 MHz, CDCl$_3$) δ=5.17 (s, 2H); 5.35 (d, J=8.4 Hz, 1H); 6.60 (d, J=8.1 Hz, 1H); 7.12–7.71 (m, 14H); 8.38 (s, 1H). TLC: R$_f$=0.31 (95:5 chloroform: methanol).

Intermediate 7

3-Amino-5-phenyl-1,3-dihydro-benzo[e][1,4]diazepin-2-one

A solution of 3-[(benzyloxycarbonyl)amino]-5-phenyl-1,3-dihydro-benzo[e][1,4]diazepin-2-one (7.00 g, 18.2 mmol) in glacial acetic acid (200 mL), prepared as in Intermediate 6, is saturated with HBr gas. The reaction is warmed to 70° C. and held for 20 min. The temperature is raised to 80° C. and maintained for an additional 20 min. The resulting slurry is cooled to ambient temperature, diluted with anhydrous diethyl ether (200 ml), agitated for 0.5 hrs., filtered and washed with diethyl ether. The hydrobromide salt is dried at 60° C. under vacuum to provide the dihydrobromide salt (6.836 g, 16.5 mmol) of the title compound. The free base is obtained by partitioning the dihydrobromide (6.100 g, 14.3 mmol) between aqueous potassium carbonate (5% w/v, 50 mL) and a mixture of ethyl acetate, isopropanol and DCM. After separating the phases, the organic layer is dried over anhydrous sodium sulfate, filtered, and concentrated in vacuo to a solid. The product is dried under high vacuum to provide the title compound as a crystalline solid (3.69 g, 14.3 mmol). $^1$H NMR (300 MHz, d6-DMSO) $\delta$=4.21 (s, 1H); 7.15–7.60 (m, 9H); 10.66 (s, 1H). TLC: $R_f$=0.33 (95:5 chloroform: methanol).

Intermediate 8

Carbonic acid (4-nitro-phenyl) ester [(R)-1-phenyl-ethyl)]ester 1-(R)-Phenyl ethanol (2.939 g, 24.1 mmol) and anhydrous pyridine (2.05 mL, 25.3 mmol) are combined under nitrogen in anhydrous DCM (10 mL) and cooled to 0°–5° C. with an ice-water bath. A solution of 4-nitrophenyl chloroformate (4.85 g, 24.1 mmol) in anhydrous DCM (15 mL) is added dropwise over 15 min. The reaction is allowed to warm to ambient temperature and stirred overnight under nitrogen. After cooling to 0°–5° C., the reaction is quenched with aqueous hydrochloric acid (1N). The phases are separated and the organic phase is dried over anhydrous magnesium sulfate, filtered, and concentrated in vacuo to an oil. The oil is purified by chromatography on flash grade silica gel using 15% ethyl acetate in n-hexane. Fractions containing the product are combined and concentrated in vacuo to provide the title compound as an oil (5.872 g, 20.5 mmol). $^1$H NMR (300 MHz, CDCl$_3$) $\delta$=1.70 (d, J=6.4 Hz, 3H); 5.84 (q, J=6.6 Hz, 1H); 7.81–7.47 (m, 7H); 8.25 (d, J=8.9 Hz, 2H). TLC: $R_f$=0.5 (1:4 ethyl acetate: n-hexane).

Intermediates 9 & 10

3(S)-{[(R)-1-phenyl-ethoxycarbonyl]amino}-5-phenyl-1,3-dihydro-benzo[e][1,4]diazepin-2-one and 3(R)-{[(R)-1-phenyl-ethoxycarbonyl]amino}-5-phenyl-1,3-dihydro-benzo[e][1,4]diazepin-2-one A mixture of 3-amino-5-phenyl-1,3-dihydro-benzo[e][1,4]diazepin-2-one (2.100 g, 8.124 mmol), prepared as in Intermediate 7, carbonic acid (4-nitro-phenyl) ester [(R)-1-phenyl-ethyl) ester (2.332 g, 8.124 mmol), prepared as in Intermediate 8, and anhydrous triethylamine (1.133 mL, 8.124 mmol) is combined in acetonitrile (25 mL) under nitrogen, heated to reflux and held overnight. After removing the reaction solvent in vacuo, the residue is dissolved in ethyl acetate and washed twice with aqueous sodium hydroxide (1N). After extracting the combined aqueous layers with ethyl acetate, the organic layers are combined, washed with saturated aqueous brine, dried over anhydrous sodium sulfate, and then concentrated in vacuo. The diastereomers are separated by chromatography on TLC mesh silica gel using a gradient of 30–35% ethyl acetate in n-hexane, followed by chromatography on TLC mesh silica gel using 35% ethyl acetate in n-hexane and finally chromatography on flash grade silica gel using 30% ethyl acetate in n-hexane. The pure fractions of each diastereomer from each column are combined to provide the less polar Intermediate 9 (1.345 g, 3.367 mmol) and the more polar Intermediate 10 (1.210 g, 3.029 mmol).

The absolute stereochemistry of Intermediates 9 and 10 are assigned by analogy to the elution profile of the enantiomers of Intermediates 9 and 10 previously reported (Bock, M. G.; Freidinger, R. M. Euro. Pat. 0 508 796 A1, 1992).

Intermediate 9: $^1$H NMR (300 MHz, d6-DMSO) $\delta$=1.47 (d, J=6.4 Hz, 3H); 4.96–5.02 (m, 1H); 5.68 (q, J=6.6 Hz, 1H); 7.18–7.65 (m, 14H); 8.32 (d, J=9.0 Hz, 1H); 10.81 (s, 1H). CHN: Calc. C$_{24}$H$_{21}$N$_3$O$_3$.0.3H$_2$O C: 71.20 H: 5.38 N:10.38 Found: C: 71.23 H: 5.38 N: 10.30.

Intermediate 10: $^1$H NMR (300 MHz, d6-DMSO) $\delta$=1.46 (d, J=6.6 Hz, 3H); 4.95–5.01 (m, 1H); 5.68 (q, J=6.5 Hz, 1H); 7.18–7.66 (m, 14H); 8.34 (d, J=8.2 Hz, 1H); 10.84 (s, 1H). CHN: Calc. C$_{24}$H$_{21}$N$_3$O$_3$.0.3H$_2$O C:71.20H: 5.38 N:10.38 Found: C: 71.33 H: 5.37 N: 10.33.

Intermediate 11

N-Isopropyl-2-(2-oxo-5-phenyl-3-(S)-{[(R)-1-phenyl-ethoxycarbonyl|amino}-2,3-dihydro-benzo[e][1,4]diazepin-1-yl-N-phenyl acetamide Sodium hydride (60% dispersion in mineral oil, 76.5 mg, 1.91 mmol) is added to a solution of 3(S){[(R)-1-phenyl-ethoxycarbonyl|amino}-5-phenyl-1,3-dihydro-benzo[e][1,4]diazepin-2-one (0.727 g, 1.822 mmol), prepared as in Intermediate 9, in anhydrous DMF (10 mL) under nitrogen at 0°–5° C. After stirring for 1 hr., a solution of 2-bromo-N-isopropyl-N-phenyl-acetamide (0.490 g, 1.822 mmol), prepared as in Intermediate 3, in anhydrous DMF (3 mL) is added and the temperature is maintained at 0°–5° C. for 30 min. The reaction mixture is added via pipette to a vigorously stirred solution (75 mL) of ice/water containing aqueous sodium hydrogen sulfate (approximately 0.5 mL 1N). The resulting slurry is diluted with 100 mL water, cooled to 0°–5° C., filtered, washed with water, and dried overnight under high vacuum to provide the title compound (1.045 g, 1.82 mmol) as a white solid. $^1$H NMR (300 MHz, CDCl$_3$) $\delta$=1.08 (d, J=6.5 Hz, 6H); 1.58 (d, J=7.2 Hz, 3H); 3.92 (d, J=16.4 Hz, 1H); 4.26 (d, J=16.1 Hz, 1H); 4.-95–5.09 (m, 1H); 5.33 (d, J=7.9 Hz, 1H); 5.76 (q, J=6.1 Hz, 1H); 6.70 (d, J=7.7 Hz, 1H); 7.12–7.62 (m, 19H). MS (FAB): [M+H]$^+$=575.

Intermediate 12

N-Isopropyl-2-(2-oxo-5-phenyl-3-(R)-{[(R)-1-phenyl-ethoxycarbonyl]amino}-2,3-dihydro-benzo[e][1,4]diazepin-1-yl-N-phenyl acetamide By employing conditions similar to those described in Intermediate 11, 3(R)-{[(R)-1-phenyl-ethoxycarbonyl]amino}-5-phenyl-1,3-dihydro-benzo[e][1,4]diazepin-2-one (0.725 g, 1.817 mmol), prepared as in Intermediate 10, is converted to the title compound, which is obtained as a white solid (1.027 g, 1.788 mmol) $^1$H NMR (300 MHz, CDCl$_3$) $\delta$=1.04–1.15 (m, 6H); 1.50–1.57 (m, 3H); 3.92 (d, J=16.7 Hz, 1H); 4.29 (d, J=16.7 Hz, 1H); 4.98–5.11 (m, 1H); 5.38 (d, J=8.5 Hz, 1H); 5.74–5.84 (m, 1H); 6.64 (d, J=8.0 Hz, 1H); 7.10–7.63 (m, 19H). MS (FAB): [M+H]$^+$=575.

Intermediate 13

2-[3-(S)-Amino-2-oxo-5-phenyl-2,3-dihydro-benzo[e][1,4]diazepin-1-yl]-N-isoproryl-N-phenyl-acetamide hydrobromide A solution N-Isopropyl-2-(2-oxo-5-phenyl-3-(S)-{[(R)-1-phenylethoxycarbonyl]-amino}-2,3-dihydro-benzo[e][1,4]diazepin-1-yl-N-phenyl acetamide (0.950 g, 1.655 mmol), prepared as in Intermediate 11, in anhydrous DCM (25 mL) at 0°–5° C. is saturated with hydrogen bromide gas and then stirred for 30 min. After removing excess hydrogen bromide by sparging the solution with nitrogen, the reaction mixture is concentrated in vacuo and triturated with anhydrous diethyl ether. The resulting slurry is filtered, washed with diethyl ether, and dried under vacuum overnight. The crude product is recrystallized from DCM/diethyl ether, filtered and dried under high vacuum to provide the title compound as a yellow solid (812 mg, 1.60 mmol). $^1$H NMR (300 MHz, CDCl$_3$) δ=0.94–1.10 (m, 6H); 4.26 (s, 2H); 4.83–6.97 (m, 1H); 5.69 (s, 1H); 7.19–7.86 (m, 14H). MS (FAB): [M+H]$^+$=427.

Intermediate 14

2-[3-(R)-Amino-2-oxo-5-phenyl-2,3-dihydro-benzo [e][1,4]diazepin-1-yl]-N-isopropyl-N-phenyl-acetamide hydrobromide By employing conditions similar to those described in Intermediate 13, N-Isopropyl-2-(2-oxo-5-phenyl-3-(R)-{[(R)-1-phenyl-ethoxycarbonyl]amino}-2,3-dihydro-benzo[e] [1,4]diazepin-1-yl-N-phenyl acetamide (0.950 g, 1.655 mmol), prepared as in Intermediate 12, is converted to the title compound, which is obtained as a yellow solid (0.840 g, 1.657 mmol). $^1$H NMR (300 MHz, CDCl$_3$) δ=0.98–1.08 (m, 6H); 4.26 (s, 2H); 4.82–6.96 (m, 1H); 5.71 (s, 1H); 7.18–7.86 (m, 14H). MS (FAB): [M+H]$^+$=427.

Intermediate 15

3-Nitrobenzoic acid t-butyl ester

Potassium t-butoxide (3.82 g, 32.30 mmol) is added to a solution of 3-nitrobenzoyl chloride (5.00 g, 26.94 mmol) in anhydrous THF (70 mL) and stirred under nitrogen for 2 hrs. The reaction mixture is concentrated in vacuo and partitioned between DCM and water. After separating the phases, the aqueous layer is back-extracted with ethyl acetate. The organic layers are combined, dried over anhydrous magnesium sulfate, filtered and then concentrated in vacuo. The crude product is purified on flash grade silica gel using 0–5% gradient of ethyl acetate in n-hexane. Fractions containing the product are combined, concentrated in vacuo, and then dried under high vacuum to provide the title compound as an oil (3.82 g, 17.1 mmol). $^1$H NMR (300 MHz, CDCl$_3$) δ=1.63 (s, 9H); 7.62 (t, J=7.9 Hz, 1H); 8.29–8.41 (m, 2H); 8.78–8.80 (m, 1H). MS (CI): [M+H]$^+$=224.

Intermediate 16

3-Amino-benzoic acid t-butyl ester

A solution of 3-nitro-benzoic acid t-butyl ester (3.77 g, 16.9 mmol), prepared as in Intermediate 15, in absolute ethanol (50 mL) is combined with palladium on carbon (10 wt %, 0.30 g) and stirred under atmospheric hydrogen for approximately 3 hrs. The reaction mixture is filtered through a pad of diatomaceous earth and then concentrated in vacuo to an oil which crystallized when dried under high vacuum providing the title compound as a tan solid (3.28 g, 16.9 mmol). $^1$H NMR (300 MHz, CDCl$_3$) δ=1.58 (s, 9H); 6.79–6.87 (m, 1H), 7.19 (t, J=8.5 Hz, 1H); 7.24–7.34 (m, 1H); 7.38 (d, J=8.0 Hz, 1H). MS (CI): [M+H]$^+$=194.

Intermediate 17

3-(2H)-Tetrazol-5-yl-phenylamine hydrochloride

3-Aminobenzonitrile (10.0 g, 84.7 mmol) and tributyltinazide (42 g, 127.1 mmol) are heated together at 160° C. under nitrogen for 2 hrs. The cooled mixture is diluted with diethyl ether (300 mL), extracted with 2N aqueous HCl (2200 mL) and the combined aqueous extracts cooled in an ice-methanol bath for 0.5 hrs. The resulting precipitate is separated by filtration, washed with ether (100 mL) and dried to give a pale pink solid. This is recrystallized from methanol (600 mL) to give 3-(2H-Tetrazol-5-yl)-phenylamine hydrochloride as an off-white solid (12.1 g, 61.2 mmol). $^1$H NMR (300 MHz, d6-DMSO): 7.32 (d, J=7.8 Hz, 1H), 7.57 t, 1H), 7.82 (m, 2H) m.p.: 256°–262° C. (dec).

Intermediate 18

N-Isopropyl-2-{2-oxo-5-phenyl-3-[(benzyloxycarbonyl)amino]-2,3-dihydro-benzo[e][1,4]diazepin-1-yl}-N-phenyl acetamide Sodium hydride (60% dispersion in mineral oil, 428 mg, 10.7 mmol) is added to a suspension of 3-[(benzyloxycarbonyl)amino]-5-phenyl-1,3-dihydro-benzo[e] [1,4]diazepin-2-one (3.924 g, 10.19 mmol), prepared as in Intermediate 6, in anhydrous DMF under nitrogen at 0°–5° C. After stirring for 1 hr., 2-Bromo-N-isopropyl-N-phenyl-acetamide (2.739 g, 10.70 mmol), prepared as in Intermediate 3, in anhydrous DMF (5 mL) is added and the mixture is allowed to stir at ambient temperature overnight. The reaction is added via pipette to water (200 mL) with vigorous agitation. The resulting slurry is diluted with water (50 mL) and then cooled to 0°–5° C. with a ice-water bath. After stirring for 30 min., the cold slurry is filtered, washed with water and then dried overnight under high vacuum to provide the title compound as a white solid (5.765 g, 10.29 mmol) of sufficient purity for the next step. $^1$H NMR (300 MHz, CDCl$_3$) δ=1.09 (d, J=6.8 Hz, 6H); 3.92 (d, J=16.5 Hz, 1H); 4.28 (d, J=16.5 Hz, 1H); 4.97–5.08 (m, 1H); 5.08–5.19 (m, 2H); 5.39 (d, J=8.2 Hz, 1H); 6.70 (d, J=8.1 Hz, 1H); 7.11–7.62 (m, 19H). MS (FAB): [M+H]$^+$=561

Intermediate 19

2-[3-Amino-2-oxo-5-phenyl-2,3-dihydro-benzo[e][1,4]-diazepin-1-yl]-N-isoproryl-N-phenyl-acetamide hydrochloride A suspension of N-isopropyl-2-{2-oxo-5-phenyl-3-[(benzyloxycarbonyl)amino]-2,3-dihydro-benzo[e][1,4] diazepin-1-yl}-N-phenyl acetamide (2.500 g, 4.46 mmol), prepared as in Intermediate 18, palladium on carbon (10 wt %, 125 mg) and concentrated hydrochloric acid (0.446 mL, 5.352 mmol) in absolute ethanol (75 mL) is stirred under atmospheric hydrogen overnight. The reaction mixture is filtered through a pad of diatomaceous earth, concentrated in vacuo and triturated with anhydrous diethyl ether. After filtering the slurry, the residual solid is dried overnight under high vacuum to provide the title compound as a white solid (1.866 g, 4.04 mmol). $^1$H NMR (300 MHz, d6-DMSO) δ=0.96 (d, J=6.5 Hz, 6H); 4.10–6.28 (m, 2H); 4.68–6.82 (m, 1H); 5.14 (s, 1H); 7.22–7.76 (m, 14H); 9.04 (b, 2H). MS (FAB): [M+H]$^+$=427.

Intermedate 20

3-[(4-nitrophenyl)oxycarbonyl]-amino-benzoic acid tert-butyl ester

A solution of 4-nitro-phenylchloroformate (3.28 g, 16.24 mmol) in anhydrous DCM (25 mL) is added dropwise over 20 min. to a solution of 3-amino-benzoic acid t-butyl ester (3.15 g, 16.24 mmol) and anhydrous pyridine (1.379 mL, 17.05 mmol) in anhydrous DCM (25 mL) under nitrogen at 0°–5° C. The reaction mixture is allowed to warm to ambient temperature and stirred overnight. After washing with aqueous HCl (1N), the reaction solution is dried over anhydrous magnesium sulfate and concentrated in vacuo to a solid. The crude product is slurried in n-hexane for 30 min., filtered and dried under high vacuum to provide the title compound as a white crystalline solid (4.460 g, 12.45 mmol). $^1$H NMR (300 MHz, CDCl$_3$) δ=1.69 (s, 9H); 7.11 (b, 1H); 7.38–7.49 (m, 3H); 7.78 (d, J=7.5 Hz, 2H); 7.91–7.94 (m, 1H); 8.27–8.33 (m, 2H). MS (FAB): [M+H]$^+$=358.

Intermediate 21

3-[3-(2-oxo-5-phenyl-2,3-dihydro-1H-benzo[e][1,4]diazepin-3-yl-ureido]-benzoic acid tert butyl ester A mixture 3-amino-5-phenyl-1,3-dihydro-benzo[e][1,4]diazepin-2-one (1.500 g, 5.80 mmol), prepared as in Intermediate 7, 3-[(4-nitrophenyl)oxycarbonyl]-amino-benzoic acid tert-butyl ester (2.078 g, 5.80 mmol), prepared as in Intermediate 20, and triethylamine (0.85 mL, 6.09 mmol) in acetonitrile (60 mL) is heated to reflux under nitrogen. After heating for 1.5 hrs., the reaction slurry is cooled to 0°–5° C., filtered, and washed with acetonitrile. The product is dried overnight under high vacuum to provide the title compound as a white crystalline solid (2.480 g, 5.27 mmol). $^1$H NMR (300 MHz, CD$_3$OD) δ=1.58 (s, 9H); 5.34 (s, 1H); 7.24–7.67 (m, 12H); 8.01–8.02 (m, 1H). TLC: R$_f$=0.4 (9:1 chloroform: methanol).

Intermediate 22

3-[(benzyloxycarbonyl)amino]-5-methyl-1,3-dihydro-benzo[e][1,4]diazepin-2-one

By employing conditions similar to those described in Intermediate 6, except that the final treatment with ammonium acetate/acetic acid is not performed, 2-amino-acetophenone (1.86 g, 13.8 mmol) is converted to the crude product, which is obtained in a solution of ethyl acetate. The product in solution is concentrated in vacuo, triturated with anhydrous diethyl ether and filtered. After drying overnight under vacuum, the title compound is isolated as a white solid (2.770 g, 8.56 mmol). $^1$H NMR (300 MHz, d6-DMSO) δ=2.38 (s, 3H); 5.81 (d, J=7.7 Hz, 1H); 5.02 (s, 2H); 7.10–7.42 (m, 7H); 7.53 (t, J=7.1H, 1H); 7.75 (d, J=7.2 Hz, 1H); 8.20 (d, J=8.5 Hz, 1H); 10.69 (s, 1H). MS (FAB): [M+H]$^+$=324.

Intermediate 23

N-Isproryl-2-(5-methyl-2-oxo-3-[(benzyloxycarbonyl)amino]-2,3-dihydro-benzo[e][1,4]diazepin-1-yl)-N-phenyl acetamide By employing conditions similar to those described in Intermediate 18, 3-[(benzyloxycarbonyl)amino]-5-methyl-1,3-dihydro-benzo[e][1,4]diazepin-2-one (0.500 g, 1.55 mmol), prepared as in Intermediate 22, is converted to the title compound, which is obtained as a crystalline solid (0.775 g, 1.55 mmol). $^1$H NMR (300 MHz, CDCl$_3$) δ=1.04–1.12 (m, 6H); 2.45 (s, 3H); 3.90 (d, J=16.6 Hz, 1H); 4.22 (d, J=16.6 Hz, 1H); 4.92–5.25 (m, 4H); 6.59 (d, J=8.0 Hz, 1H); 7.11–7.58 (m, 14H). MS (ESI): [M+H]$^+$=499.

Intermediate 24

2-(3-Amino-5-methyl-2-oxo-2,3-dihydro-benzo[e][1,4]diazepin-1-yl)-N-isororpyl-N-phenyl acetamide By employing conditions similar to those described in Intermediate 19, except that the reaction is performed in the absence of hydrochloric acid, N-isopropyl-2-(5-methyl-2-oxo-3-[(benzyloxycarbonyl)amino]-2,3-dihydro-benzo[e][1,4]diazepin-1-yl)-N-phenyl acetamide (0.700 g, 1.40 mmol), prepared as in Intermediate 23, is converted to a ethanolic solution of the crude title compound. The residue obtained after filtration through celite and concentration in vacuo is partitioned between ethyl acetate and saturated aqueous brine. The ethyl acetate layer is separated, dried over anhydrous sodium sulfate, filtered, concentrated in vacuo and dried under high vacuum to provide the title compound as a foam (0.513 g, 1.40 mmol). $^1$H NMR (300 MHz, CDCl$_3$) δ=1.09 (d, J=6.8 Hz, 6H); 2.43 (s, 3H); 3.82 (d, J=16.7 Hz, 1H); 4.29 (d, J=16.4 Hz, 1H); 4.37 (b, 1H); 4.93–5.07 (m, 1H); 7.07–7.52 (m, 9H). MS (ESI): [M+H]$^+$=365.

Intermediate 25

7-Nitro-1-tert-butoxycarbonyl-indazole

A solution of 7-nitro-1H-indazole (2.81 g, 17.23 mmol), di-tertbutyl carbonate (7.52 g, 34.5 mmol), triethylamine (4.81 mL, 34.5 mmol) and 4-dimethylamino-pyridine (2.11 g, 17.2 mmol) in anhydrous acetonitrile (100 mL) is stirred under nitrogen at ambient temperature for approximately 3 hrs. After removing the solvent in vacuo, the residue is partitioned between ethyl acetate and aqueous sodium hydrogen sulfate (1N). The organic layer is separated, washed with saturated aqueous brine, dried over anhydrous magnesium sulfate, filtered and concentrated in vacuo. The crude product is purified by chromatography on flash grade silica gel using DCM. Fractions containing the product are combined, concentrated in vacuo to a solid and dried under high vacuum to provide the title compound as a yellow solid (2.674 g, 10.16 mmol). $^1$H NMR (300 MHz, d6-DMSO) δ=1.55 (s, 9H); 7.58 (t, J=8.0 Hz, 1H); 8.20 (d, J=7.4 Hz, 1H); 8.30 (d, J=7.7 Hz, 1H); 8.67 (s, 1H). TLC: R$_f$=0.5 (DCM).

Intermediate 26

7-Amino-1-tert-butoxycarbonyl-indazole

A mixture of 7-Nitro-1-tert-butoxycarbonyl-indazole (1.000 g, 3.798 mmol), prepared as in Intermediate 25, and palladium on carbon (10 wt %, 0.10 g) in ethyl acetate (25 mL) at ambient temperature is stirred under atmospheric hydrogen overnight. The mixture is filtered through celite and concentrated in vacuo to an oil which solidified under high vacuum to provide the title compound as a purple solid (0.860 g, 3.686 mmol). $^1$H NMR (300 MHz, d6-DMSO) δ=1.59 (b, 9H); 6.13 (b, 2H); 6.76 (d, J=7.6 Hz, 1H); 6.97 (d, J=7.6 Hz, 1H); 7.04–7.07 (m, 1H); 8.24 (s, 1H). TLC: R$_f$=0.47 (25:75 ethyl acetate: n-hexane).

Intermediate 27

N-Isopropyl-N-(4-methoxy-phenyl)-2-(2-oxo-5-phenyl-2,3-dihydro-benzo[e][1,4]diazepin-1-yl)-acetamide By employing conditions similar to those described in Intermediate 11, 5-phenyl-1,3-dihydro-benzo[e][1,4]diazepin-2-one (Bock et. al., *J. Org. Chem.* 1987, 52, 3232–3239, 3.00 g, 12.71 mmol) and 2-bromo-N-isopropyl-N-(4-methoxy-phenyl)-acetamide (3.820 g, 13.35 mmol) are converted to the title compound, which is obtained as a wet white solid. The product is dissolved in anhydrous DCM, dried over anhydrous sodium sulfate and then concentrated in vacuo. The residue is triturated with n-hexane, filtered and dried overnight under vacuum to provide the title compound as a white solid (5.380 g, 12.18 mmol). $^1$H NMR (300 MHz, d6-DMSO) δ=0.91–0.97 (m, 6H); 3.70 (d, J=10.4 Hz, 1H); 3.76 (s, 3H); 4.08 (s, 2H); 4.51 (d, J=10.6 Hz, 1H); 4.67–6.78 (m, 1H); 6.97–7.63 (m, 13H). MS (FAB): [M+H]$^+$=442.

Intermediate 28

{1-[Isopropyl-(4-methoxy-phenyl)-carbamoylmethyl]-2-oxo-5-phenyl-2,3-dihydro-1H-benzo[e][1,4]diazepin-3-yl}-acetic acid tert-butyl ester A solution of 0.5M potssium bis(trimethylsilyl)amide (0.5M in toluene, 4.75 mL, 2.38 mmol) is added via syringe to a solution of N-isopropyl-N-(4-methoxy-phenyl)-2-(2-oxo-5-phenyl-2,3-dihydro-benzo[e][1,4]diazepin-1-yl)-acetamide (1.000 g, 2.27 mmol) in anhydrous THF (15 mL) at −78° C. under nitrogen. After stirring for 15 min., tert-butyl bromoacetate (0.384 mL, 2.38 mmol) is added via micropipette and the reaction is maintained at −78° C. for 45 min. Acetic acid is added (0.026 mL, 0.454 mmol) and the reaction is allowed to stir to ambient temperature overnight. After removing the solvent in vacuo, the residue is purified by chromatography on flash grade silica gel using 50% ethyl acetate in n-hexane. Fractions containing the product are combined, concentrated in vacuo to a white foam, and dried under high vacuum to provide the title compound (1.035 g, 1.863 mmol). $^1$H NMR (300 MHz, d6-DMSO) δ=0.88–0.94 (m, 6H); 1.34 (s, 9H); 2.86–3.06 (m, 2H); 3.77 (s, 3H); 3.90 (t, J=7.2, 1H); 4.06 (d, J=16.8 Hz, 1H); 4.20 (d, J=16.5 Hz, 1H); 4.63–6.74 (m, 1H); 6.97–7.08 (m, 2H); 7.15–7.31 (m, 4H); 7.36–7.53 (m, 6H); 7.57–7.66 (m, 1H). MS (FAB): [M+H]$^+$=556.

Intermediate 29

{1-[Isopropyl-(4-methoxy-phenyl)-carbamoylmethyl]-2-oxo-5-phenyl-2,3-dihydro-1H-benzo[e][1,4]diazepin-3-yl}-acetic acid By employing conditions similar to those described in Example 10, {1-[Isopropyl-(4-methoxy-phenyl)-carbamoylmethyl]-2-oxo-5-phenyl-2,3-dihydro-1H-benzo[e][1,4]diazepin-3-yl}-acetic acid tert-butyl ester (0.910 g, 1.638 mmol), prepared as in Intermediate 28, is converted to the title compound, which is obtained as an off-white solid (0.943 g, 1.888 mmol) which is used without further purification. $^1$H NMR (300 MHz, CDCl$_3$) δ=1.07 (d, J=6.7 Hz, 6H); 3.14–3.26 (m, 1H); 3.54–3.65 (m, 1H); 3.81 (s, 3H); 4.02 (d, J=16.8 Hz, 1H); 4.28–6.29 (m, 2H); 4.88–6.99 (m, 1H); 6.76–7.88 (m, 13H). MS (FAB): [M+H]$^+$=500.

Intermediate 30

2-[3-(N-Benzyloxycarbonyl-amino)-2-oxo-5-pyridin-3-yl-2,3-dihydro-benzo[e][1,4]diazepin-1-yl]-N-isopropyl-N-(4-methoxy-phenyl)-acetamide.

A solution of 1.000 g of 3-(benzyloxycarbonyl-amino)-5-pyridin-3-yl-1,3-dihydro-benzo[e][1,4]diazepin-2-one (2.591 mmol, Pat. App. WO 93/16999) in 7 mL dimethylformamide at 0° C. under nitrogen was treated with 5.44 mL (2.72 mmol) of potassium bis(trimethylsilyl)amide (0.5M in toluene). After stirring for 10 min., a solution of 0.779 g of 2-bromo-N-isopropyl-N-(4-methoxy-phenyl)-acetamide (2.72 mmol), prepared as in Intermediate 5, in 2 mL of dimethylformamide was added to the mixture. The reaction was stirred to ambient temperature over 2 hrs. and then quenched into a mixture of ethyl acetate, water and saturated aqueous brine. The phases were separated and the aqueous phase was back-extracted with ethyl acetate. The organic layers were combined, washed with saturated aqueous brine, dried over anhydrous sodium sulfate, filtered and evaporated in vacuo to a residue. The residue was purified on flash grade silica gel using 9:1 ethyl acetate/hexane. The appropriate fractions were combined, evaporated in vacuo to a foam and triturated with hexane. After evaporation of the hexane in vacuo, the residual solid was dried under high vacuum to provide 1.295 g of the title compound as a tan solid. $^1$H NMR (300 MHz, d6-DMSO) _=8.70 (m, 2H), 8.56 (d, 1H, J=8.6), 7.92 (m, 1H), 7.71 (m, 1H), 7.52 (m, 2H), 7.32 (m, 9H), 7.07 (d, 2H, J=8.8), 5.19 (d, 1H, J=8.8), 5.08 (s, 2H), 4.71 (m, 1H), 4.27 (d, 1H, J=16.5), 4.12 (d, 1H, J=16.5), 3.81 (s, 3H), 0.95 (m, 6H); MS (ESI): [M+H]$^+$=592.

Intermediate 31

2-(3-Amino-2-oxo-5-pyridin-3-yl-2,3-dihydro-benzo[e][1,4]diazepin-1-yl)-N-isopropyl-N-(4-methoxy-phenyl)-acetamide hydrobromide A solution of 1.00 g of 2-[3-(N-benzyloxycarbonyl-amino)-2-oxo-5-pyridin-3-yl-2,3-dihydro-benzo[e][1,4]diazepin-1-yl]-N-isopropyl-N-(4-methoxy-phenyl)-acetamide (1.690 mmol), prepared as in Intermediate 30, in 6 mL glacial acetic acid was saturated with hydrogen bromide gas and stirred at ambient temperature for 16 hrs. The reaction mixture was evaporated in vacuo to a residue and triturated with diethyl ether. The resulting slurry was filtered, washed with diethyl ether, and dried under high vacuum to provide 1.062 g of the title compound as a dihydrobromide salt. $^1$H NMR (300 MHz, CD$_3$OD) _=9.06 (m, 2H), 8.85 (m, 1H), 8.21 (dd, 1H, J=5.8, 8.1), 7.84 (m, 1H), 7.61 (d, 1H, J=8.3), 7.50 (m, 2H), 7.27 (m, 2H), 7.10 (d, 2H, J=8.8), 5.25 (s, 1H), 4.52 (d, 1H, J=16.7), 4.31 (d, 1H, J=16.7), 3.88 (s, 3H), 1.07 (m, 6H); MS (ESI): [M+H]$^+$=458.

Intermediate 32

2-(2,4-dioxo-6H-benzo[d][1,3]oxazin-1-yl)-N-isopropyl-N-phenyl-acetamide

A suspension of isatoic anhydride (9.54 g, 58.5 mmol) and 2-bromo-N-isopropyl-N-phenyl-acetamide (15.0 g, 58.5 mmol) and potassium carbonate (8.1 g, 58.5 mmol) in DMF (300 mL) is stirred at room temperature for 3.5 h. The mixture is filtered through celite and concentrated in vacuo to a light brown solid. Trituration with water gave a light brown solid (25 g). Recrystallization from EtOH/petroleum ether (3:2, 500 mL) gave 14.7 g (72%) of 2-(2,4-dioxo-6H-benzo[d][1,3]oxazin-1-yl)-N-isopropyl-N-phenyl-acetamide as a tan powder. $^1$H NMR (300 MHz, CDCl$_3$): 1.11 (d, J=6.8 Hz, 6H); 4.38 (s, 2H); 4.96 (m, J=6.8 Hz, 1H); 6.87 (d, J=8.5 Hz, 1H); 7.2–7.6 (m, 6H); 7.71 (t, J=7.0 Hz, 1H); 8.14 (d, J=7.8 Hz, 1H). MS(ESI): [M+H]$^+$=488.

Intermediate 33

2-(2,4-Dioxo-6H-benzo[d][1,3]oxazin-1-yl)-N-isopropyl-N-(4-methyoxy-phenyl)-acetamide By employing conditions similar to Intermediate 30 except 2-Bromo-N-isopropyl-N-(4-methoxy-phenyl)-acetamide (16.74 g, 58.5 mmol) is substituted for 2-Bromo- N-isopropyl-N-phenyl-acetamide, the title compound is obtained as a tan solid (18.53 g, 50.3 mmol). $^1$H NMR (300 MHz, d$_6$-DMSO): d 1.00 (d, 6H, J=6.6 Hz); 3.81 (s, 3H); 4.29(s, 2H); 4.73 (m, 1H); 7.02–7.41 (m, 6H); 7.84 (m, 1H); 8.01 (m, 1H). TLC (Ethyl Acetate/Hexane(1:1)): R$_f$=0.44.

Intermediate 34

2-(2,5-dioxo-2,3,4,5-tetrahydro-benzo[e][1,4]diazepin-1-yl)-N-isopropyl-N-phenylacetamide A suspension of 2-(2,4-dioxo-6H-benzo[d][1,3]oxazin-1-yl)-N-isopropyl-N-phenylacetamide (10 g, 31 mmol), glycine (2.32 g, 31 mmol) and triethylamine (4.32 mL, 31 mmol) in water (50 mL) is stirred at 50° C. for 5 h. The reaction mixture is concentrated to a brown viscous oil, acetic acid (100 mL) is added and the mixture heated at reflux for 6 h. The reaction mixture is concentrated to a brown viscous oil, dissolved in ethyl acetate (300 mL) and washed with water, saturated aqueous sodium bicarbonate and brine. The resulting solution is dried over magnesium sulfate and concentrated to a yellow foam. Recrystallization from ethyl acetate/petroleum ether (4:1, 100 mL) gave the title compound (7.55 g, 21.5 mmol) as an off-white powder. 1H NMR (300M Hz, CDCl$_3$): 1.12 (d, J=6.7 Hz, 6H); 3.6–6.4 (m, 4H); 5.05 (m, J=6.7 Hz, 1H); 6.62 (m, 1H); 7.1–7.6 (m, 7H); 7.84 (d, J=7.5 Hz, 1H). MS (FAB): [M+H]$^+$=352.

Intermediate 35

2-(4-Azido-5-oxo4,5-dihydro-1,2,3a,6-tetra-benzo[e]azulen-6-yl)-N-isoproryl-N-phenyl acetamide A solution of bis(trimethylsilyl)amide (0.5M in toluene, 3.52 mL, 1.76 mmol) is added via syringe to a solution of N-isopropyl-2-(5-oxo-6,5-dihydro-1,2,3a,6-tetraaza-benzo[e]azulene-6-yl)-N-phenyl-acetamide (600 mg, 1.600 mmol) in anhydrous THF (10 mL) at –78° C. After stirring for 15 min., trisyl azide (J. Org. Chem. 1973, 38, 11–16, 0.618 g, 2.00 mmol) is added as a solid in one portion. The reaction is stirred at –78° C. for 4 min. and then quenched by addition of glacial acetic acid (457 uL, 8.0 mmol). The quenched reaction mixture is allowed to warm to ambient temperature, concentrated in vacuo to a residue, and chromatographed on flash grade silica gel using 80% ethyl acetate in n-hexane. Fractions containing the product are concentrated in vacuo to a solid and dried under high vacuum to afford the title compound as a white foam (416 mg, 1.127 mmol). $^1$H NMR (300 MHz, d6-DMSO, 80° C.): 0.98 (d, J=6.6 Hz, 6H); 4.08 (d, J=16.0 Hz, 1H); 4.19 (d, J=16.0 Hz, 1H); 4.62–6.74 (m, 1H); 6.70 (bs, 1H); 7.25 (d, J=7.2 Hz, 2H); 7.39–7.50 (m, 5H); 7.63 (t, J=7.2 Hz, 1H); 7.88 (d, J=7.6 Hz, 1H); 8.77 (s, 1H). MS (FAB): [M+H]$^+$=417.

Intermediate 36

2-(4-Amino-5-oxo-4,5-dihydro-1,2,3a,6-tetraaza-benzo[e]azulen-6-yl)-N-isopropyl-N-phenyl-acetamide A solution of 2-(4-azido-5-oxo-4,5-dihydro-1,2,3a,6-tetra-benzo[e]azulen-6-yl)-N-isopropyl-N-phenyl acetamide (150 mg, 0.361 mmol) under nitrogen in methanol (4 mL) is treated with stannous chloride (103 mg, 0.541 mmol) at ambient temperature. After 15 min., the methanol is removed in vacuo and the residue partitioned between DCM and 5% aqueous potassium carbonate containing sodium chloride. The organic layer is separated and the aqueous layer extracted with DCM. The organic layers are combined, dried over anhydrous sodium sulfate, filtered and then concentrated in vacuo to yield 2-(4-Amino-5-oxo-6,5-dihydro-1,2,3a,6-tetraaza-benzo[e]azulen-6-yl)-N-isopropyl-N-phenyl-acetamide (140 mg, 0.361 mmol) as a white foam which is used in the preparation of Example 1 without further characterization.

Intermediate 37

N-isopropyl-2-(5-oxo-6,5-dihydro-1,2,3a,6-tetraaza-benzo[e]azulene-6-yl)-N-phenyl-acetamide Pyridine (3.0 mL, 36.9 mmol) is added to a stirred suspension of 2-(2,5-dioxo-2,3,4,5-tetrahydro-benzo[e][1,4]diazepin-1-yl)-N-isopropyl-N-phenyl-acetamide (6.45 g, 18.4 mmol) in toluene (180 mL). The mixture is warmed to 80° C. to give a cloudy solution. Phosporus oxychloride (1.14 mL, 12.2 mmol) is added and the mixture is heated at reflux for 1.75 hrs. during which a red oil separated out from the reaction mixture. After cooling to room temperature, toluene is removed and the residual oil is diluted with water and extracted with ethyl acetate (×2). The organic extract is washed with aqueous hydrochloric acid (1N) and brine, dried over magnesium sulfate and concentrated to give a tan foam (6.3 g). The crude product is dissolved in toluene (180 mL) and formyl hydrazine (2.8 g, 46.2 mmol) is added. The mixture is heated at reflux for 22 hrs. After cooling to room temperature the reaction mixture is diluted with ethyl acetate (200 mL) and washed with water (×2) and brine, dried over magnesium sulfate and concentrated to a light brown foam. Purification by silica-gel flash chromatography with 5–10% methanol in dichloromethane as eluent followed by recrystallization from ethyl acetate/petroleum ether (1:2, 150 mL) provided the title compound as a white powder (2.85 g 7.60 mmol). MP 141°–3° C. Found C, 66.4; H, 5.65; N, 18.4; $C_{21}H_{21}N_5O_2 \cdot 0.25$ H$_2$O requires C, 66.4, H, 5.7; N, 18.4. $^1$H NMR (300 MHz, CDCl$_3$): 1.13 (d, J=6.6 Hz, 6H); 3.5–5.9 (m, 4H); 5.05 (m, J=6.6 Hz, 1H); 7.1–7.7 (m, 8H); 8.01 (d, J=7.6 Hz, 1H); 8.26 (s, 1H). MS (FAB): [M+H]$^+$=376.

Intermediate 38

(S)-2-[5-chloro-3-(1H-indol-3-ylmethyl)-2-oxo-2,3-dihydro-benzo[e][1,4]diazepin-1-yl]-N-isopropyl-N-(4-methoxy-phenyl)-acetamide S-2-[3-(1H-Indol-3-ylmethyl)-2,5-dioxo-2,3,4,5-tetrahydro-benzo[e][1,4]diazepin-1-yl]-N-isopropyl-N-(4-methyoxy-phenyl)-acetamide(289 mg, 0.567 mmol) is dissolved in toluene (6 mL) at 80° C. under nitrogen. Phosphorous oxychloride (116 mg, 0.752 mmol) is added dropwise and the reaction mixture is refluxed 2.5 hrs. The solvent is removed in vacuo and the crude product purified by flash chromatography on silica gel (30 g) eluted with ethyl acetate/hexane (2:3, 500 mL). Fractions containing they desired product are combined and concentrated in vacuo and dried briefly under high vacuum to give the title compound (167 mg, 0.315 mmol) as a yellow foam. $^1$H NMR (300 MHz, CDCl$_3$): d 1.10 (d, 6H, J=6.9 Hz); 3.51 (m, 1H); 3.68 (m, 1H); 3.71 (d, 1H, J=16.8 Hz); 3.82 (s, 3H); 3.84 (m, 1H); 4.45 (d, 1H, J=16.8 Hz); 5.03 (m, 1H); 6.88–7.34 (m, 10H); 7.49 (t, 1H); 7.59 (d, 1H, J=7.8 Hz); 7.68 (d, 1H, J=8.0 Hz); 7.99 (s, 1H). TLC (ethyl acetate/hexane, 2:3): R$_f$=0.38.

Intermediate 39

(R)-2-[5-chloro-3-(1H-indol-3-ylmethyl)-2-oxo-2,3-dihydrobenzo[e][1,4]diazepin-1-yl]-N-isopropyl-N-(4-methoxy-phenyl)-acetamide By employing conditions similar to Intermediate 38 except R-2-[3-(1H-Indol-3-ylmethyl)-2,5-dioxo-2,3,4,5- tetrahydro-benzo[e][1,4]diazepin-1-yl]-N-isopropyl-N-(4-methoxy-phenyl)-acetamide(430 mg, 0.842 mmol) is substituted for S-2-[3-(1H-Indol-3-ylmethyl)-2,5-dioxo-2,3,4,5-tetrahydrobenzo[e][1,4]diazepin-1-yl]-N-isopropyl-N-(4-methyoxy-phenyl)-acetamide and other reagents scaled accordingly, the title compound is obtained as a yellow foam (118 mg, 0.223 mmol). $^1$H NMR (300 MHz,CDCl$_3$): d 1.10 (d, 6H, J=6.9 Hz); 3.51 (m, 1H); 3.68 (m, 1H); 3.71 (d, 1H, J=16.8 Hz); 3.82 (s, 3H); 3.84 (m, 1H); 4.45 (d, 1H, J=16.8 Hz); 5.03 (m, 1H); 6.88–7.34 (m, 10H); 7.49 (t,1H); 7.59 (d,1H, J=7.8 Hz); 7.68 (d,1H, J=8.0 Hz); 7.99 (s,1H). TLC (ethyl acetate/hexane, 2:3): R$_f$=0.38.

Intermediate 40

(R)-{3-(1H-Indol-3-ylmethyl)-1-[isopropyl-(4-methoxy-phenyl)-carbamoylmethyl]-2,5-dioxo-1,2,3,5-tetrahydro-benzo[e][1,4]diazepin-6-yl}-acetic acid tert-butyl ester To a solution of (R)-2-[3-(1H-Indol-3-ylmethyl)-2,5-dioxo-2,3,4,5-tetrahydrobenzo[e][1,4]diazepin-1-yl]-N-isopropyl-N-(4-methyoxy-phenyl)-acetamide (160 mg, 0.313 mmol), prepared as in Example 20, in dry DMF (4 mL) cooled in an ice bath is added NaH (15 mg, 0.376 mmol, 60% in mineral oil) and stirred 30 min. t-Butyl bromoacetate (61 mg, 0.313 mmol) is added and the reaction mixture stirred with cooling for 1 h followed by stirring overnight at ambient temperature. The solvent is removed in vacuo and the resultant oil taken into ethyl acetate (50 mL), washed with saturated NaHCO$_3$ (25 mL) and brine (25 mL), dried with MgSO$_4$, filtered and concentrated to a yellow oil. The crude product and a major by-product, the dialkylated material, (R)-{3-(1-tert-butoxycarbonyl methyl-1H-Indol-3-ylmethyl)-1-[isopropyl-(4-methoxy-phenyl)-carbamoylmethyl]-2,5-dioxo-1,2,3,5-tetrahydro-benzo[e][1,4]diazepin-6-yl}-acetic acid tert-butyl ester, are separated by preparative HPLC on a Delta-Pak C-18 column eluted with a linear gradient from 40–65% CH$_3$CN in H$_2$O with 0.1% TFA buffer over a 30 minute period at a rate of 150 mL/min. The appropriate fraction is frozen and lyophilized to give the TFA salt of the title compound (84.6 mg, 0.115 mmol) as a white powder: MS(FAB) m/z=625.3 (MH$^+$); RP-HPLC (Vydac-C18, 40–65% CH$_3$CN in H$_2$O with 0.1% TFA buffer linear gradient, 30 min, 1.5 mL/min) t$_r$=20.5 min (t$_o$=2.5 min).

Intermediate 41

2-[3-(N-Benzyloxycarbonyl-amino)-2-oxo-5-cyclohexyl-2,3-dihydro-benzo[e][1,4]diazepin-1-yl]-N-isopropyl-N-(4-methoxy-phenyl)-acetamide By employing conditions similar to those described in Intermediate 11, 5-cyclohexyl-1,3-dihydro-benzo[e][1,4]diazepin-2-one (Patent Application WO 93/19063, 3.00 g, 7.66 mmol) and 2-bromo-N-isopropyl-N-(4-methoxy-phenyl)-acetamide (2.193 g, 7.66 mmol) are converted to the title compound, which is obtained as a white solid (4.597 g, 7.70 mmol). $^1$H NMR (300 MHz, CDCl$_3$) δ=7.60 (m, 2H), 7.28 (m, 6H), 7.19 (m, 1H), 7.08 (m, 1H), 6.95 (m, 4H), 5.34 (m, 1H), 5.16 (d, 1H, J=12.3), 5.05 (d, 1H, J=12.3), 4.95 (m, 1H), 4.22 (d, 1H, J=16.6), 3.93 (d, 1H, J=16.6), 3.84 (s, 3H), 2.93 (m, 1H, 1.69 (m, 10H), 1.05 (m, 6H). MS (FAB): [M+H]$^+$=597.1.

Intermediate 42

2-[3-(N-Benzyloxycarbonyl-amino)-4-N-oxide-2-oxo-5-cyclohexyl-2,3-dihydro-benzo[e][1,4]diazepin-1-yl]-N-isopropyl-N-(4-methoxy-phenyl)-acetamide By employing conditions similar to those described in Example 16, 2-[3-(N-benzyloxycarbonyl-amino)-2-oxo-5-cyclohexyl-2,3-dihydro-benzo[e][1,4]diazepin-1-yl]-N-isopropyl-N-(4-methoxy-phenyl)-acetamide (2.00 g, 3.36 mmol) is converted to the title compound. The crude product was purified on flash grade silica gel eluting with 1:1 ethyl acetate/hexane. Fractions containing the product were combined, evaporated in vacuo and triturated with n-hexane. Hexane was removed in vacuo and the remaining solid was dried under high vacuum to provide the title compound as a white cyrstalline solid (1.176 g, 1.92 mmol). $^1$H NMR (300 MHz, CDCl$_3$) δ=7.56 (d, 1H, J=7.8), 7.44 (m, 2H), 7.28 (m, 7H), 7.05 (m,1H), 6.93 (m, 2H), 6.58 (d, 1H, J=9.5), 5.69 (d, 1H, J=9.4), 5.21 (d, 1H, J=12.3), 5.02 (d, 1H, J=12.3), 4.97 (m, 1H), 4.25 (d, 1H, J=16.5), 3.88 (d, 1H, J=16.5), 3.83 (s, 3H), 3.26 (m,1H), 2.08 (m, 2H), 1.69 (m, 4H), 1.33 (m, 4H), 1.05 (m, 6H). MS (FAB): [M+H]$^+$=613.1.

Intermediate 43

2-(3-Amino-4-N-oxide-2-oxo-5-cyclohexyl-2,3-dihydro-benzo[e][1,4]diazepin-1-yl)-N-isopropyl-N-(4-methoxy-phenyl)-acetamide A solution of 2-[3-(N-benzyloxycarbonyl-amino)4-N-oxide-2-oxo-5-cyclohexyl-2,3-dihydro-benzo[e][1,4]diazepin-1-yl]-N-isopropyl-N-(4-methoxy-phenyl)-acetamide (1.00 g, 1.63 mmol) in 100 mL of 1:1 ethyl acetate: ethanol was combined with Palladium on carbon (10 wt %, 333 mg) and hydrogenolyzed under an atmosphere of hydrogen for 5 hrs. The reaction mixture was filtered, evaporated in vacuo, and triturated with diethyl ether. The diethyl ether was removed in vacuo and the residual solid was dried under high vacuum to provide the title compound as a white crystalline solid (733 mg, 1.53 mmol). $^1$H NMR (300 MHz, CDCl$_3$) δ=7.45 (m, 3H), 7.25 (m, 2H), 7.06 (m, 1H), 6.93 (m, 2H), 4.96 (m, 1H), 4.90 (s, 1H), 4.25 (d, 1H, J=16.4), 3.88 (d, 1H, J=16.4), 3.82 (s, 3H), 3.23 (m, 1H), 2.12 (m, 2H), 1.70 (m, 4H), 1.28 (m, 4H), 1.05 (m, 6H). MS (FAB): [M+H]$^+$=479.3.

Example 1

1N-Isopropyl-2-(2-oxo-5-phenyl-3-{3-[3-(1H-tetrazol-5-yl)-phenyl]-ureido}-2,3-dihydro-benzo[e][1,4]diazepin-1-yl)-N-phenyl-acetamide According to Process B, a mixture of of 1,1'-carbonyldiimidazole (28.6 mg, 0.176 mmol) and 2-(3-Amino-2-oxo-5-phenyl-2,3-dihydro-benzo[e][1,4]diazepin-1-yl)-N-isopropyl-N-phenyl-acetamide (75.0 mg, 0.176 mmol), prepared as in Intermediate 13, in anhydrous THF (5 mL) is stirred at ambient temperature under a nitrogen atmosphere for approximately 30 min. and then heated to reflux. After refluxing for 2 hrs, 3-(2H-tetrazol-5-yl)-phenylamine hydrochloride (36.5 mg, 0.185 mmol), prepared as in Intermediate 17, is added in one portion and the reaction is held at reflux for an additional 5 hrs and then concentrated in vacuo to a residue. The residue is purified by reversed-phase HPLC on a C-18 column with a gradient elution of 30–68% acetonitrile in aqueous trifluoroacetic acid (0.1% v/v) over 30 min. at 100 mL/min. Fractions containing the product are combined, frozen, and lyophilized to provide the title compound as a white lyophile (37 mg, 0.060 mmol). $^1$H NMR (300 MHz, d6-DMSO) δ=1.04 (d, 6H); 4.21 (d, J=16.4 Hz, 1H); 4.31 (d, J=17.1 Hz, 1H); 4.79–6.86 (m, 1H); 5.35–5.36 (m, 1H); 7.32–7.78 (m, 19H); 8.26 (b, 1H); 9.38 (b, 1H); MS (ESI): [M+H]$^+$=614.

Example 2

N-Isopropyl-2-[5-methyl-2-oxo-3-(3-phenyl-ureido)-2,3-dihydro-benzo[e][1,4]diazepin-1-yl]-N-phenyl-acetamide According to Process A, phenyl isocyanate (0.065 mL, 0.602 mmol) is added to a solution of 2-(3-Amino-5-methyl- 2-oxo-2,3-dihydro-benzo[e][1,4]diazepin-1-yl)-N-isopropyl-N-phenyl-acetamide (219 mg, 0.602 mmol), prepared as in Intermediate 24, under nitrogen in DCM (3 mL). The reaction mixture is stirred at ambient temperature overnight and then concentrated in vacuo. The residue is dissolved in ethyl acetate, washed twice with 1N HCl, dried over anhydrous magnesium sulfate, and then concentrated again to a residue. The crude product is purified by reversed-phase HPLC on a C-18 column with 60% acetonitrile in aqueous trifluoroacetic acid (0.1% v/v) over 30 min. at 100 mL/min. Fractions containing the product are combined, frozen and lyophilized to provide the title compound as a white lyophile (92 mg, 0.190 mmol). $^1$H NMR (300 MHz, CDCl$_3$) δ=1.02–1.25 (m, 6H); 2.59 (s, 3H); 4.08 (d, J=16.9 Hz, 1H); 4.17 (d, J=16.9 Hz, 1H); 4.93–5.00 (m, 1H); 5.56 (d, J=6.3 Hz, 1H); 7.02–7.61 (m, 14H); MS(FAB): [M+H]$^+$=484.

Example 3

N-Isopropyl-2-[2-oxo-5-phenyl-3-(3-phenyl-ureido)-2,3-dihydro-benzo[e][1,4diazepin-1-yl]-N-phenyl-acetamide According to Process A, phenyl isocyanate (0.027 mL, 0.246 mmol) is added to a solution of 2-(3-Amino-2-oxo-5-phenyl-2,3-dihydro-benzo[e][1,4]diazepin-1-yl)-N-isopropyl-N-phenyl-acetamide (100 mg, 0.235), prepared as in Intermediate 13, in anhydrous DCM (3 mL) under nitrogen and allowed to stir at ambient temperature overnight. The reaction mixture is washed with aqueous potassium carbonate (5% w/v), dried over anhydrous magnesium sulfate, and concentrated in vacuo to a residue. The crude product is purified by reversed-phase HPLC on a C-18 column with a gradient elution of 42–60% acetonitrile in aqueous trifluoroacetic acid over 30 min. at 100 mL/min. Fractions containing the product are combined, frozen and lyophilized to provide the title compound as a white lyophile (78 mg, 0.143 mmol) $^1$H NMR (300 MHz, CDCl$_3$) δ=1.06–1.08 (m, 6H); 4.06–6.29 (m, 2H); 4.92–5.01 (m, 1H); 5.67 (b, 1H); 7.07–7.68 (m, 21H); MS(ESI): [M+H]$^+$=546.

Example 4

2-{3-[3-(1-H-indazole-7-yl)-ureido]-5-methyl-2-oxo-2,3-dihydro-benzo[e][1,4]diazepin-1-yl}-N-isopropyl-N-phenyl-acetamide A. 2-(3-{3-[1-(tert-Butoxycarbonyl)-indazol-7-yl]-ureido}-5-methyl-2-oxo-2,3-dihydro-benzo[e][1,4]diazepin-1yl)-N-isoproryl-N-phenyl-acetamide According to process A, employing conditions similar to those described in Example 12, 2-(3-amino-5-methyl-2-oxo-2,3-dihydro-benzo[e][1,4]diazepin-1-yl)-N-isopropyl-N-phenyl acetamide (113 mg, 0.311 mmol), prepared as in Intermediate 24, and 7-amino-1-tert-butoxycarbonyl-indazole (113 mg, 0.311 mmol), prepared as in Intermediate 26, are converted to the crude title compound. The product is purified by chromatography on flash grade silica gel using 70% ethyl acetate in n-hexane. Fractions containing the product are concentrated in vacuo to a solid and dried under high vacuum to provide the title compound as an off-white solid (77 mg, 0.121 mmol). $^1$H NMR (300 MHz, CDCl$_3$) δ=1.08 (t, J=7.1 Hz, 6H); 1.74 (s, 9H); 2.48 (s, 3H); 3.97 (d, J=16.9 Hz, 1H); 4.25 (d, J=16.9 Hz, 1H); 4.97–5.08 (m, 1H); 5.50 (d, J=7.6 Hz, 1H); 6.50 (d, J=6.5 Hz, 1H); 7.17–7.59 (m, 11H); 8.12 (s, 1H); 8.41 (d, J=8.0 Hz, 1H); 10.74 (s, 1H). Hz, MS (FAB): [M+H]$^+$=624.

B. 2-{3-[3-(1-H-indazole-7-yl)-ureido]-5-methyl-2-oxo-2,3-dihydro-benzo[e][1,4]diazepin-1-yl}-N-isopropyl-N-phenyl-acetamide Trifluoroacetic acid (2.0 mL) and 2-(3-{3-[1-(tert-Butoxycarbonyl)-indazol-7-yl]-ureido}-5-methyl-2-oxo-2,3-dihydro-benzo[e][1,4]diazepin-1yl)-N-isopropyl-N-phenyl-acetamide (75 mg, 0.120 mmol), prepared as in Example 4A, are combined, cooled to 0–5_C. with an ice water bath, and stirred under nitrogen for 15 min. The reaction mixture is concentrated in vacuo to an oil, triturated with a mixture of diethyl ether and n-hexane and then concentrated again. This process is repeated several times until a solid is obtained on concentration. The product is dried under high vacuum overnight at room temperature and then at 65_C. overnight to give the title compound as a crystalline solid (61 mg, 0.117 mmol). The pure material is then lyophilized from acetonitrile/water. $^1$H NMR (300 MHz, CDCl$_3$) δ=1.08–1.12 (m, 6H); 2.73 (s, 3H); 4.11 (d, J=16.8 Hz,,H); 4.24 (d, J=16.6 Hz, 1H); 4.93–5.08 (m, 1H); 5.76 (b, 1H); 6.99–7.75 (m, 14H); 8.00 (b, 1H); 8.83 (b, 1H). MS(FAB): [M+H]$^+$=524.

Example 5

3-{3-[1-(Isopropyl-phenyl-carbamoylmethyl)-2-oxo-5-phenyl-2,3-dihydro-1H-benzo[e][1,4]diazepin-3-yl]-ureido}-benzoic acid A. 3-{3-1-(Isopropyl-phenyl-carbamoylmethyl)-2-oxo-5-phenyl-2,3-dihydro-1H-benzo[e][1,4]diazepin-3-yl]-ureido}-benzoic acid tert butyl ester According to Process A, employing conditions similar to those described in Intermediate 21, 2-[3-amino-2-oxo-5-phenyl-2,3-dihydro-benzo[e][1,4]diazepin-1-yl]-N-isopropyl-N-phenyl-acetamide hydrobromide (0.250 g, 0.466 mmol), prepared as in Intermediate 14, 3-[4-(nitrophenyl)oxycarbonyl]-aminobenzoic acid tert-burtyl ester (0.167 g, 0.466 mmol), prepared as in Intermediate 20,and triethylamine (0.069 mL, 0.489 mmol) are converted to the title compound, which is obtained as a white solid (0.149 g, 0.231 mmol). $^1$H NMR (300 MHz, CDCl$_3$) δ=1.07 (d, J=7.0 Hz, 6H); 1.58 (s, 9H); 4.00 (d, 16.0 Hz, 1H); 4.28 (d, 16.0 Hz, 1H); 4.95–5.06 (m, 1H); 5.60 (d, J=7.8 Hz, 1H); 6.66–6.72 (m, 1H); 7.13–7.80 (m, 19H). MS (FAB): [M+H]$^+$=646.

B. 3-{3-1-(Isopropyl-phenyl-carbamoylmethyl)-2-oxo-5-phenyl-2,3-dihydro-1H-benzo[e][1,4]diazepin-3-yl]-ureido}-benzoic acid A solution of 3-{3-[1-(Isopropyl-phenyl-carbamoylmethyl)-2-oxo-5-phenyl-2,3-dihydro-1H-benzo[e][1,4]diazepin-3-yl]-ureido}-benzoic acid tert-butyl ester (145 mg, 0.225 mmol), prepared as in Example 5A, in anhydrous DCM (2 mL) at 0–5_C. under nitrogen is treated with triflouroacetic acid (2 mL). After stirring for 2 hrs., the reaction mixture is concentrated in vacuo and triturated with anhydrous ether. The resulting slurry is filtered and the product dried overnight under high vacuum at ambient temperature to provide the title compound as a crystalline solid (80 mg, 0.136 mmol). $^1$H NMR (300 MHz, d6-DMSO) δ=0.96 (d, J=6.8 Hz, 6H); 4.12 (d, J=16.6 Hz, 1H); 4.23 (d, J=16.6 Hz, 1H); 4.71–6.76 (m, 1H); 5.18–5.27 (m, 1H); 7.24–7.70 (m, 19H); 8.02 (b, 1H); 9.22 (b, 1H). MS (FAB): [M+H]$^+$=590.

Example 6

2-Amino-4-chloro-N-[1-(isopropyl-phenyl-carbamoylmethyl)-5-phenyl-2-oxo-5-phenyl-2,3-dihydro-1H-benzo[e][1,4]diazepin-3-yl]-benzamide According to Process C, a mixture of 2-(3-Amino-2-oxo-5-phenyl-2,3-dihydro-benzo[e][1,4]diazepin-1-yl)-N- isopropyl-N-phenyl-acetamide (150 mg, 0.280 mmol), prepared as in Intermediate 14, 4-chloro-2-amino-benzoic acid (48 mg, 0.280 mmol), N,N-diisopropylethylamine (48.7 µL, 0.280 mmol), 1-(3-dimethylaminopropyl)-3-ethylcarbodiimide hydrochloride (54 mg, 0.280 mmol), and 1-hydroxybenzotriazole (43 mg, 0.318 mmol) are combined in DCM (5 mL) under nitrogen. After stirring overnight at ambient temperature, the reaction mixture is concentrated in vacuo and dissolved in ethyl acetate. This solution is washed consecutively with aqueous sodium hydrogen sulfate (1N), aqueous sodium hydroxide (1N), and saturated aqueous brine. After drying over anhydrous sodium sulfate, the solution is concentrated in vacuo to a residue. The crude product is purified by chromatography on flash grade silica gel using 50% ethyl acetate in n-hexane. Fractions containing the product are combined and concentrated in vacuo to an oily residue. The purified material is dissolved in DCM and concentrated again to an oily residue. This procedure is repeated several times until a solid is obtained on concentration. The pure material obtained is dried under high vacuum overnight to provide the title compound as a crystalline solid (130 mg, 0.224 mmol). The product is lyophilized from acetonitrile/water. $^1$H NMR (300 MHz, CDCl$_3$) δ=1.08–1.10 (m, 6H); 4.00 (d, J=16.6 Hz, 1H); 4.34 (d, J=16.6 Hz, 1H); 4.99–5.03 (m, 1H); 5.83 (d, J=7.6 Hz, 1H); 6.68 (b, 2H); 7.16–7.70 (m, 17H); 8.21 (d, J=6.9 Hz, 1H). MS (FAB): [M+H]$^+$=580.

Example 7

3-{3-[1-(Isopropyl-phenyl-carbamoylmethyl)-5-methyl-2-oxo-2,3-dihydro-1H-benzo[e][1,4]diazepin-3-yl]-ureido}-benzoic acid A. 3-{3-[1-(Isopropyl-phenyl-carbamoylmethyl)-5-methyl-2-oxo-2,3-dihydro-1H-benzo[e][1,4]diazepin-3-yl]-ureido}-benzoic acid tert butyl ester According to process A, employing conditions similar to those described in Intermediate 21, 2-[3-amino-5-methyl-2-oxo-2,3-dihydro-benzo[e][1,4]diazepin-1-yl]-N-isopropyl-N-phenyl-acetamide hydrobromide (0.100 9, 0.466 mmol), prepared as in Intermediate 24, 3-[4-(nitrophenyl)oxycarbonyl]-aminobenzoic acid tert-burtyl ester (0.167 g, 0.466 mmol), prepared as in Intermediate 20, and triethylamine (0.069 mL, 0.489 mmol) are converted to the title compound, which is obtained as a white solid (60 mg, 0.102 mmol). $^1$H NMR (300 MHz, CDCl$_3$) δ=1.07 (t, J=6.7 Hz, 6H); 1.58 (s, 9H); 2.46 (s, 3H); 3.94 (d, J=16.7 Hz, 1H); 4.24 (d, J=16.7 Hz, 1H); 4.95–5.06 (m, 1H); 5.41 (d, J=7.7 Hz, 1H); 6.58 (d, J=8.0 Hz, 1H); 6.74 (s, 1H); 7.15–7.77 (m, 13H). MS (FAB): [M+H]$^+$=584.

B. 3-{3-[1-(Isopropyl-phenyl-carbamoylmethyl)-5-methyl-2-oxo-2,3-dihydro-1H-benzo[e][1,4]diazepin-3-yl]-ureido}-benzoic acid Employing the same procedure described for example 5B, 3-{3-[1-(Isopropyl-phenyl-carbamoylmethyl)-5-methyl-2-oxo-2,3-dihydro-1H-benzo[e][1,4]diazepin-3-yl]-ureido) benzoic acid tert-butyl ester (102 mg, 0.175 mmol), prepared as in Example 6A, is converted to title compound, which is obtained as a crystalline solid (55 mg, 0.104 mmol). $^1$H NMR (300 MHz, CDCl$_3$) δ=1.09 (d, J=6.5 Hz, 6H); 2.63 (s, 3H); 4.06 (d, J=16.1 Hz, 1H); 4.19 (d, J=16.7 Hz, 1H); 4.92–5.02 (m, 1H); 5.58 (d, J=7.26 Hz, 1H); 7.09–7.78 (m, 11H); 7.89 (s, 1H); 8.05 (d, J=8.1 Hz, 1H); 8.29 (d, 8.3 Hz, 1H); 8.55 (s, 1H). MS (FAB): [M+H]$^+$=528.

Example 8

3-(3-{1-[Isopropyl-(4-methoxy-phenyl)-carbamoylmethyl]-2-oxo-5-phenyl-2,3-dihydro-1H-benzo[e][1,4]diazepin-3-yl}-ureido)-benzoic acid A. 3-(3-{1-[Isopropyl-(4-methoxy-phenyl)-carbamoylmethyl-2-oxo-5-phenyl-2,3-dihydro-1H-benzo[e][1,4]diazepin-3-yl}-ureido)-benzoic acid tert-butyl ester According to Process D, employing conditions similar to those described for Intermediate 18, 3-[3-(2-oxo-5-phenyl-2,3-dihydro-1H-benzo[e][1,4]diazepin-3-yl-ureido]-benzoic acid tert-butyl ester (0.400 g, 0.851 mmol), prepared as in Intermediate 21, and 2-bromo-N-isopropyl-N-(4-methoxyphenyl)-acetamide (0.244 g, 0.851 mmol), prepared as in Intermediate 5, are converted to the title compound, which is obtained as a white solid (0.417 g, 0.617 mmol). $^1$H NMR (300 MHz, CD$_3$Cl) δ=1.05 (d, J=6.7 Hz, 6H); 1.58 (s, 9H); 3.81 (s, 3H); 3.99 (d, J=16.5 Hz, 1H); 4.31 (d, J=16.5 Hz, 1H); 4.92–5.05 (m, 1H); 5.60 (d, J=7.7 Hz, 1H); 6.59–7.83 (m, 19H). MS (FAB): [M+H]$^+$=676.

B. 3-(3-{1-[Isopropyl-(4-methoxy-phenyl)-carbamoylmethyl-2-oxo-5-phenyl-2,3-dihydro-1H-benzo[e][1,4]diazepin-3yl}-ureido)-benzoic acid Employing similar procedures as described for example 5B, 3-(3-(1-[Isopropyl-(4-methoxy-phenyl)-carbamoylmethyl]-2-oxo-5-phenyl-2,3-dihydro-1H-benzo[e][1,4]diazepin-3yl}-ureido)-benzoic acid tert-butyl ester (150 mg, 0.222 mmol), prepared as in Example 8A, is converted to the title compound (94 mg, 0.132 mmol). $^1$H NMR (300 MHz, d6-DMSO) δ=0.94 (d, J=6.3 Hz, 6H); 3.77 (s, 3H); 4.12 (d, J=16.7 Hz, 1H); 4.22 (d, J=16.7 Hz, 1H); 4.65–6.78 (m, 1H); 5.24 (d, J=8.4 Hz, 1H); 6.97–7.72 (m, 18H); 8.02 (s, 1H); 9.22 (s, 1H). MS(FAB: [M+H]$^+$=620.

Example 9

3-(3-{1-[(4-Dimethylamino-phenyl)-isopropyl-carbamoylmethyl]-2-oxo-5-phenyl-2,3-dihydro-1H-benzo[e][1,4]diazepin-3-yl}-ureido)-benzoic acid A. 3-(3-{1-[-f(4-Dimethylamino-phenyl)-isopropyl-carbamoylmethyl]-2-oxo-5-phenyl-2,3-dihydro-1H-benzo[e][1,4]diazepin-3-yl}-ureido)-benzoic acid tert-butyl ester According to Process D, employing conditions similar to those described in Intermediate 18, 3-[3-(2-oxo-5-phenyl-2,3-dihydro-1H-benzo[e][1,4]diazepin-3-yl-ureido]-benzoic acid tert-butyl ester (0.400 g, 0.851 mmol), prepared as in Intermediate 21, and 2-bromo-N-(4-dimethylaminophenyl)-N-isopropyl-acetamide (0.255 g, 0.851 mmol), prepared as in Intermediate 4, are converted to the title compound, which is obtained as an off-white solid (0.470 g, 0.682 mmol). $^1$H NMR (300 MHz, CDCl$_3$) δ=1.06 (d, J=6.8 Hz, 6H); 1.58 (s, 9H); 2.96 (s, 6H); 3.99 (d, J=16.6 Hz, 1H); 4.37 (d, J=16.6 Hz, 1H); 4.92–5.03 (m, 1H); 5.59 (d, J=7.4 Hz, 1H); 6.58–7.84 (m, 19H). MS (FAB): [M+H]$^+$=689.

B. 3-(3-{1-[(4-Dimethylamino-phenyl)-isopropyl-carbamoylmethyl]-2-oxo-5-phenyl-2,3-dihydro-1H-benzo[e][1,4]diazepin-3-yl}-ureido)-benzoic acid According to procedures described for Example 5B, 3-(3-{1-[(4-Dimethylamino-phenyl)-isopropyl-carbamoylmethyl]-2-oxo-5-phenyl-2,3-dihydro-1H-benzo[e][1,4]diazepin-3-yl}ureido)-benzoic acid tert-butyl ester (180 mg, 0.261 mmol), prepared as in Example 9A, is converted to the title compound, which is obtained as a pink solid (133 mg, 0.210 mmol). The product is lyophilized from acetonitrile/water. $^1$H NMR (300 MHz, d6-DMSO) δ=0.87–0.98 (m, 6H); 2.07 (s, 6H); 4.09–6.27 (m, 2H); 4.64–6.75 (m, 1H); 5.24 (d, J=8.2 Hz, 1H); 6.67–6.83 (m, 2H); 7.02–7.13 (m, 2H); 7.18–7.72 (m, 14H); 8.02 (s, 1H); 9.26 (s, 1H). MS (FAB): [M+H]$^+$=633.

Example 10

3-(2-{1-[Isopropyl-(4-methoxy-phenyl)-carbamoylmethyl]-2-oxo-5-phenyl-2,3-dihydro-1H-benzo[e][1,4]diazepin-3-yl}-acetyl-amino)-benzoic acid A. of 3-(2-{1-[Isopropyl-(4-methoxy-phenyl)-carbamoylmethyl]-2-oxo-5-phenyl-2,3-dihydro-1H-benzo[e][1,4]diazepin-3-yl}-acetylamino)-benzoic acid tert-butyl ester According to Process F, employing conditions similar to those described in Example 11, {1-[Isopropyl-(4-methoxy-phenyl) carbamoylmethyl]-2-oxo-5-phenyl-2,3-dihydro-1H-benzo[e][1,4]diazepin-3-yl}-acetic acid (200 mg, 0.326 mmol), prepared as in Intermediate 29, and 3-amino-benzoic acid t-butyl ester (69.3 mg, 0.359 mmol), prepared as in Intermediate 16, are converted to the crude title compound. The product is purified by chromatography on flash grade silica gel using 60% ethyl acetate in n-hexane. Fractions containing the product are combined, concentrated in vacuo to a tacky foam, and dried under high vacuum to provide the title compound(155 mg, 0.233 mmol) of sufficient purity for the next step. $^1$H NMR (300 MHz, d6-DMSO) δ=0.90 (t, J=7.1 Hz, 6H); 1.51 (s, 9H); 3.12–3.23 (m, 2H); 3.76 (s, 3H); 3.99–6.11 (m, 2H); 4.23 (d, J=16.9 Hz, 1H); 4.61–6.71 (m, 1H); 6.98–7.83 (m, 16H); 8.14 (s, 1H); 10.35 (s, 1H). MS (FAB): [M+H]$^+$=675.

B. 3-(2-{1-[Isopropyl-(4-methoxy-phenyl)-carbamoylmethyl]-2-oxo-5-phenyl-2,3-dihydro-1H-benzo[e][1,4]diazepin-3-yl}-acetylamino)-benzoic acid According to procedures described for Example 5B, 3-(2-{1-[isopropyl-(4-methoxy-phenyl)-carbamoylmethyl]-2-oxo-5-phenyl-2,3-dihydro-1H-benzo[e][1,4]diazepin-3-yl}acetylamino)-benzoic acid tert-butyl ester (151 mg, 0.228 mmol), prepared as in Example 10A, is converted to the title compound, which is obtained as a white solid (99 mg, 0.160 mmol). The product is lyophilized from acetonitrile/water. $^1$H NMR (300 MHz, d6-DMSO) δ=0.85–0.96 (m, 6H); 2.16 (d, J=6.8 Hz, 2H); 3.77 (s, 3H); 4.01–6.31 (m, 3H); 4.54–6.76 (m, 1H); 7.00–7.68 (m, 16H); 7.77 (d, J=8.4 Hz, 1H); 8.24 (s, 1H); 10.34 (s,1H). MS(FAB): [M+H]$^+$=619.

Example 11

2-{1-[Isopropyl-(4-methoxy-phenyl)-carbamoylmethyl]-2-oxo-5-phenyl-2,3-dihydro-1H-benzo[e][1,4]diazepin-3-yl}N-phenyl-acetamide According to Process F, a mixture of {1-[Isopropyl-(4-methoxy-phenyl)-carbamoylmethyl]-2-oxo-5-phenyl-2,3-dihydro-1H-benzo[e][1,4]diazepin-3-yl}-acetic acid (200 mg, 0.400 mmol), prepared as in Intermediate 29, aniline (0.033 mL, 0.356 mmol), and bromo-tris-pyrrolidino-phosphonium hexafluorophosphate (167 mg, 0.356 mmol) in anhydrous DCM (3 mL) is treated with diisopropylethylamine (0.170 mL, 0.978 mmol) and stirred at ambient temperature under nitrogen. After 1.5 hrs., the solvent is removed in vacuo and the residue is purified by chromatography on flash grade silica gel using 60% ethyl acetate in n-hexane. Fractions containing the product are combined, concentrated in vacuo and triturated with n-hexane. After removing the solvent in vacuo, the product is dried overnight at ambient temperature under high vacuum to provide the title compound (123 mg, 0.214 mmol) as a white solid. The product is lyophilized from acetonitrile/water. $^1$H NMR (300 MHz, d6-DMSO) δ=0.86–0.96 (m, 6H); 3.14 (d, J=6.9 Hz, 2H); 3.77 (S, 3H); 4.03–6.12 (M, 2H); 4.23 (D, J=16.8 HZ, 1H); 4.59–6.73 (M, 1H); 6.97–7.08 (M, 3H); 7.15–7.32 (M, 6H); 7.36–7.66 (M, 9H); 10.15 (S, 1H). MS (FAB): [M+H]$^+$=575.

Example 12

(S)-3-{3-[1-(Isopropyl-phenyl-carbamoylmethyl)-2-oxo-5-phenyl-2,3-dihydro-1H-benzo[e][1,4]diazepin-3-yl]-ureido}-benzoic acid A. (S)-3-{3-[1-(Isopropyl-phenyl-carbamoylmethyl)-2-oxo-5-phenyl-2,3-dihydro-1H-benzo[e][1,4]diazepin-3-yl]-ureido}-benzoic acid tert butyl ester According to Process A, triphosgene (42.0 mg, 0.142 mmol) is added to a solution of 3-amino-benzoic acid t-butyl ester (76.9 mg, 0.425 mmol) and triethylamine (237.1 uL, 1.700 mmol) in anhydrous DCM (2.5 mL) under nitrogen at 0°–5° C. and stirred for 30 min. After 2-[3-(S)-amino-2-oxo-5-phenyl-2,3-dihydro-benzo[e][1,4]diazepin-1-yl]-N-isopropyl-N-phenylacetamide hydrobromide (250 mg, 0.425 mmol), prepared as in Intermediate 13, is added, the reaction is allowed to warm to ambient temperature and stirred for 48 hrs. The reaction mixture is diluted with DCM, washed with aqueous HCl (1N), dried over anhydrous magnesium sulfate, filtered and concentrated in vacuo. The crude product is purified by chromatography on flash grade silica gel using a gradient of 40–50% ethyl acetate in n-hexane. Fractions containing the product are combined, concentrated in vacuo, triturated with hexane, concentrated again in vacuo to a solid and then dried under high vacuum over 48 hrs. to provide the title compound as a white solid (176 mg, 0.273 mmol). The product is lyophilized from acetonitrile/water. $^1$H NMR δ=1.08 (d, J=6.7 Hz, 6H); 1.58 (s, 9H); 3.97 (d, J=16.6 Hz, 1H); 4.30 (d, 16.6 Hz, 1H); 4.97–5.08 (m, 1H); 5.59 (d, J=7.6 Hz, 1H); 6.63–6.71 (m, 1H); 7.14–7.80 (m, 19H). TLC: R$_f$=0.4 (1:1 ethyl acetate: n-hexane).

B. (S)-3-{3-[1-(Isopropyl-phenyl-carbamoylmethyl)-2-oxo-5-phenyl-2,3-dihydro-1H-benzo[e][1,4]diazepin-3-yl]-ureido}-benzoic acid Employing conditions similar to Example 5B, (S)-3-{3-[1-(Isopropyl-phenyl-carbamoylmethyl)-2-oxo-5-phenyl-2,3-dihydro-1H-benzo[e][1,4]diazepin-3-yl]-ureido}-benzoic acid tert-butyl ester (152 mg, 0.235 mmol), prepared as Example 12A, is converted to the title compound, which is obtained as a white solid (117 mg, 0.198 mmol). $^1$H NMR (300 MHz, d6-DMSO) δ=0.94 (d, J=6.3 Hz, 6H); 4.11 (d, J=16.9 Hz, 1H); 4.22 (d, J=16.9 Hz, 1H); 4.67–6.79 (m, 1H); 5.19–5.28 (m, 1H); 7.19–7.71 (m, 19H); 8.02 (s, 1H); 9.21 (1H). MS (FAB): [M+H]$^+$=590.

Example 13

(R)-3-{3-[1-(Isopropyl-phenyl-carbamoylmethyl)-2-oxo-5-phenyl-2,3-dihydro-1H-benzo[e][1,4]diazepin-3-yl]-ureido}-benzoic acid A. (R)-3-{3-[1-(Isopropyl-phenyl-carbamoylmethyl)-2-oxo-5-phenyl-2,3-dihydro-1H-benzo[e][1,4]diazepin-3-yl]-ureido}-benzoic acid tert butyl ester According to Process A, employing conditions similar to those described in Example 12, 2-[3-(R)-Amino-2-oxo-5-phenyl-2,3-dihydro-benzo[e][1,4]diazepin-1-yl]-N-isopropyl-N-phenyl-acetamide hydrobromide (250 mg, 0.425 mmol), prepared as in Intermediate 14, is converted to the title compound, which is obtained as a white solid (184 mg, 0.285 mmol). $^1$H NMR (300 MHz, CDCl$_3$) δ=1.06 (d, J=6.7 Hz, 6H); 1.57 (s, 9H); 4.11 (d, J=17.0 Hz, 1H); 4.27 (d, J=17.0 Hz, 1H); 4.90–5.02 (m, 1H); 5.76 (d, J=7.5 Hz, 1H); 7.08–7.74 (m, 19H); 7.84 (b, 1H). TLC: R$_f$=0.4 (1:1 ethyl acetate:n-hexane).

B. (R)-3-{3-[1-(Isopropyl-phenyl-carbamoylmethyl)-2-oxo-5-phenyl-2,3-dihydro-1H-benzo[e][1,4]diazepin-3-yl]-ureido}-benzoic acid By employing conditions similar to Example 5B, (R)-3-{3-[1-(Isopropyl-phenyl-carbamoylmethyl)-2-oxo-5-phenyl-2,3-dihydro-1H-benzo[e][1,4]diazepin-3-yl]-ureido)-benzoic acid tert-butyl ester (168 mg, 0.265 mmol), prepared as Example 13A, is converted to the title compound, which is obtained as white solid (112 mg, 0.190 mmol). $^1$H NMR (300 MHz, d6-DMSO) δ=0.94 (d, J=6.9 Hz, 6H); 4.11 (d, J=17.3 Hz, 1H); 4.22 (d, J=17.3 Hz, 1H);

4.64–6.82 (m, 1H); 5.18–5.27 (m, 1H); 7.17–7.71 (m, 19H); 8.02 (s, 1H); 9.22 (s, 1H). MS (FAB): [M+H]$^+$=590.

Example 14

1H-indolyl-2-carboxylic acid [1-(isopropyl-phenyl-carbamoylmethyl)-2-oxo-5-phenyl-2,3-dihydro-1H-benzo[e][1,4]diazepin-3-yl]-amide According to Process D, employing conditions similar to those described in Example 6, 2-(3-Amino-2-oxo-5-phenyl-2,3-dihydro-benzo[e][1,4]diazepin-1-yl)-N-isopropyl-N-phenyl-acetamide (132 mg, 0.246 mmol), prepared as in Intermediate 13, and indolyl-2-carboxylate (39.7 mg, 0.246 mmol) are converted to the title compound. The impure material is purified by reversed-phase HPLC on a C-18 column with a gradient elution of 42–60% acetonitrile in aqueous trifluoroacetic acid (0.1% v/v) over 30 min. at 100 mL/min. Fractions containing the product are combined, frozen, and lyophilized to provide the title compound as a white lyophile (81.3 mg, 0.147 mmol). $^1$H NMR (300 MHz, d6-DMSO) δ=1.10 (d, J=6.6 Hz, 6H); 3.97 (d, J=16.6 Hz, 1H); 4.34 (d, J=16.4 Hz, 1H); 5.01–5.06 (m, 1H); 5.79 (d, J=7.8 Hz, 1H); 7.11–7.72 (m, 19H); 8.04 (d, J=8.3 Hz, 1H); 9.10 (b, 1H). MS (ESI): [M+H]$^+$=570

Example 15

{2-[1-(Isopropyl-phenyl-carbamoylmethyl)-2-oxo-5-phenyl-2,3-dihydro-1H-benzo[e][1,4]diazepin-3-ylcarbamoyl]-indol-1-yl}-acetic acid A. {2-[1-(Isopropyl-phenyl-carbamoylmethyl)-2-oxo-5-phenyl-2,3-dihydro-1H-benzo[e][1,4]diazepin-3-ylcarbamoyl]-indol-1-yl}-acetic acid tert butyl ester According to Process H, 1H-indolyl-2-carboxylic acid [1-(isopropyl-phenyl-carbamoylmethyl)-2-oxo-5-phenyl-2,3-dihydro-1H-benzo[e][1,4]diazepin-3-yl]-amide (100 mg, 0.176 mmol), prepared as in Example 14, is added to a mixture of sodium hydride (60% dispersion in mineral oil, 4.2 mg, 0.184 mmol) in anhydrous DMF (2 mL) under nitrogen. After stirring for 15 min., tert-butyl bromoacetate (31.2 uL, 0.193 mmol) is added via micropipette. After approximately 2 hrs., the reaction mixture is concentrated in vacuo to residue. The crude product is purified by reversed-phase HPLC on a C-18 column with 60% acetonitrile in aqueous trifluoroacetic acid (0.1% v/v) at 100 mL/min. Fractions containing the product are combined, frozen and lyophilized to provide the title compound as a white lyophile (100.7 mg, 0147 mmol). $^1$H NMR (300 MHz, d6-DMSO) δ=0.99–1.05 (m, 6H); 1.38 (s, 9H); 4.19 (d, J=16.9 Hz, 1H); 4.32 (d, J=16.9 Hz, 1H); 4.75–6.81 (m, 1H); 5.29 (s, 2H); 5.62–5.66 (m, 1H); 7.17–7.79 (m, 19H); 9.53–9.56 (m, 1H). MS(ESI): [M+H]$^+$=684.

B. {2-[1-(Isopropyl-phenyl-carbamoylmethyl)-2-oxo-5-phenyl-2,3-dihydro-1H-benzo[e][1,4]diazepin-3-ylcarbamoyl]-indol-1-yl}-acetic acid By employing conditions similar to Example 5B, {2-[1-(Isopropyl-phenyl-carbamoylmethyl)-2-oxo-5-phenyl-2,3-dihydro-1H-benzo[e][1,4]diazepin-3-ylcarbamoyl]-indol-1-yl}acetic acid tert butyl ester (75 mg, 0.110 mmol), prepared as in Example 16A, is converted to the title compound, which is lyophilized from acetonitrile/water to provide a yellow lyophile (69 mg, 0.110 mmol). $^1$H NMR (300 MHz, d6-DMSO) δ=0.99–1.03 (m, 6H); 4.19 (d, J=16.8 Hz, 1H); 4.34 (d, J=16.8 Hz, 1H); 4.72–6.85 (m, 1H); 5.30 (s, 2H); 5.62–5.67 (m, 1H); 7.14–7.79 (m, 19H); 9.57 (d, J=7.9 Hz, 1H). MS(ESI): [M+H]$^+$=628.

Example 16

N-Isopropyl-2-[4-N-oxide-2-oxo-5-phenyl-3-(3-phenyl-ureido)-2,3-dihydro-benzo[e][1,4]diazepin-1-yl]-N-phenyl-acetamide According to Process I, a solution of N-Isopropyl-2-[2-oxo-5-phenyl-3-(3-phenyl-ureido)-2,3-dihydro-benzo[e][1,4]diazepin-1-yl]-N-phenyl-acetamide (100 mg, 0.183 mmol), prepared as in Example 3, in anhydrous DCM (5 mL) is treated with m-chloroperbenzoic acid (50%, 64 mg, 0.183 mmol) at ambient temperature overnight. After concentration in vacuo, the product is crystallized from methanol, filtered and dried under high vacuum to provide the title compound as white crystalline solid (74 mg, 0.132 mmol). MS(FAB): [M+H]+=562. $^1$H NMR (300 MHz, d6-DMSO) δ=0.96 (d, J=6.8 Hz, 6H); 4.03 (d, J=16.6 Hz, 1H); 4.13 (d, J=16.6 Hz, 1H); 4.78–6.89 (m, 1H); 6.12 (d, J=9.1 Hz, 1H); 6.75–7.71 (m, 20H); 7.87 (b, 1H).

Example 17

3-{1-[Isopropyl-(4-methoxy-phenyl)-carbamoylmethyl]-2-oxo-5-phenyl-2,3-dihydro-1H-benzo[e][1,4]diazepin-3-ylmethyl}-indolyl Sodium hydroxide (1.218 g, 10.03 mmol) is combined in methanol (20 mL) and heated at reflux under nitrogen until dissolution occurred. The solution is cooled slightly and 3-{1-[Isopropyl-(4-methoxy-phenyl)-carbamoylmethyl]-2-oxo-5-phenyl-2,3-dihydro-1H-benzo[e][1,4]diazepin-3-ylmethyl}-1-tert-butoxycarbonyl-indolyl (100 mg, 0.149 mmol), prepared as in Example 25, is added. After heating at reflux for 30 min., the reaction mixture is concentrated in vacuo to a residue and partitioned between dichloromethane and water. After separating the layers, the aqueous layer is back-extracted with dichloromethane. The combined organics are dried over anhydrous sodium sulfate, filtered and concentrated in vacuo. The residue is dissolved in methanol and precipitated by dropwise addition of water with vigorous agitation. The resulting slurry is filtered, washed with water, and the residual solids dried overnight under high vacuum to provide the title compound as an off-white solid (69 mg, 0.121 mmol). $^1$H NMR (300 MHz, CDCl$_3$) δ=1.11 (d, J=6.8 Hz, 6H); 3.64–3.83 (m, 6H); 3.90–3.97 (m, 1H); 4.43 (d, J=16.6 Hz, 1H); 4.99–5.09 (m, 1H); 6.87–7.56 (m, 17H); 7.71 (d, J=7.8 Hz, 1H); 8.00 (b, 1H). MS (FAB): [M+H]$^+$=571.

Example 18

N-Isopropyl-N-(4-methoxy-phenyl)-2-[2-oxo-3-(3-phenyl-ureido)-5-pyridin-3-yl-2,3-dihydro-benzo[e][1,4]diazepin-1-yl]-acetamide According to process A, a solution of 175 mg of 2-(3-amino-2-oxo-5-pyridin-3-yl-2,3-dihydro-benzo[e][1,4]diazepin-1-yl)-N-isopropyl-N-(4-methoxy-phenyl)-acetamide dihydrobromide (0.283 mmol), prepared as in Intermediate 31, in 3 mL of methylene chloride was treated with 98.5 µL of triethylamine (0.706 mmol) and 33.8 µL of phenyl isocyanate (0.311 mmol). After stirring under nitrogen for 20 min., the reaction mixture was diluted with methylene chloride and washed with aqueous potassium carbonate (5% w/v). The phases were separated and the organic layer was dried over anhydrous sodium sulfate, filtered and evaporated in vacuo to a residue. The residue was triturated with 5 mL of acetonitrile and the resulting slurry was heated to reflux under nitrogen. After stirring for 20 min., the slurry was cooled to ambient temperature, filtered and washed with cold acetonitrile. The product was combined again with 3 mL of acetonitrile and brought to reflux. After stirring for 30 min., the slurry was cooled to ambient temperature, filtered and washed with cold acetonitrile. The product was dried under high vacuum to provide 95 mg of the title compound as a white crystalline solid. $^1$H NMR (300 MHz, d6-DMSO) _=9.06 (b, 1H), 8.68 (m, 2H), 7.93 (d, 1H, J=8.0), 7.72 (m, 1H), 7.53 (m, 3H), 7.37 (m, 4H), 7.26 (m, 4H), 7.07 (m, 2H), 6.94 (m, 1H), 5.31 (d, 1H, J=8.3), 4.72 (m, 1H), 4.29 (d, 1H, J=16.4), 4.16 (d, 1H, J=16.4), 3.81 (s, 3H), 0.96 (d, 6H, J=6.1); MS (ESI) [M+H]$^+$=577.

Example 19

N-Isopropyl-N-phenyl-2-[5-oxo-4-(3-phenyl-ureido)-4,5-dihydro-1,2,3a,6-tetraaza-benzo[e]azulen-6-yl]-acetamide A mixture of 2-(4-Amino-5-oxo-4,5-dihydro-1,2,3a,6-tetraaza-benzo[e]azulen-6-yl)-N-isopropyl-N-phenyl-acetamide (140 mg, 0.361 mmol), prepared as in Intermediate 36, and phenyl isocyanate (39.2 uL, 0.361 mmol) in 5 mL dry DCM is stirred at ambient temperature under nitrogen overnight. After concentrating in vacuo, the residue is chromatographed on flash grade silica gel using 95% ethyl acetate in n-hexane. The fractions containing the product are combined, concentrated in vacuo, and triturated with hexane. After removing the solvent in vacuo, the product is dried overnight at ambient temperature under high vacuum to provide the title compound (84 mg, 0.165 mmol) as a white solid. The product is lyophilized from acetonitrile/water. $^1$H NMR (300 MHz, d6-DMSO): 0.89–0.96 (m, 6H); 4.02 (d, J=16.3 Hz, 1H); 4.16 (d, J=16.3 Hz, 1H); 4.62–6.73 (m, 1H); 5.99–6.05 (m, 1 H); 6.93 (t, J=7.2 Hz; 1H); 7.10–7.89 (m, 14H); 8.10 (s, 1H); 9.30 (s, 1H). MS (FAB): [M+H]$^+$510.

Example 20

(R)-2-[3-(1H-Indol-3-ylmethyl)-2,5-dioxo-2,3,4,5-tetrahydro-benzo[e][1,4]diazepin-1-yl]-N-isopropyl-N-(4-methyoxy-phenyl)-acetamide A mixture of 2-(2,4-Dioxo-6H-benzo[d][1,3]oxazin-1-yl)-N-isopropyl-N-(4-methyoxy-phenyl)-acetamide (1.00 g, 2.71 mmol), D-tryptophan (554 mg, 2.71 mmol) and triethylamine (0.378 mL, 2.71 mmol) are combined in water (20 mL) and stirred for 5 hrs. at 50° C. After concentration in vacuo, the reaction mixture is combined with glacial acetic acid (20 mL) and refluxed for 5 hrs. The reaction mixture is filtered and then concentrated in vacuo to an oil. The oil is dissolved in ethyl acetate and washed consecutively with water (2×), saturated aqueous sodium bicarbonate, and brine. The solution is dried over anyhydrous magnesium sulfate, filtered, treated with activated charcoal, filtered and concentrated in vacuo to a yellow foam. The product is crystallized from methanol (15 mL). The resulting slurry is cooled with an ice/water bath, filtered and washed with cold methanol (3×4 mL), and dried under high vacuum to provide the title compound as white solid (469 mg, 0.918 mmol). $^1$H NMR (300 MHz, CDCl$_3$): 1.11 (m, 6H); 3.22 (m, 1H); 3.46 (m, 1H); 3.69 (d, 1H, J=16.6 Hz); 3.83 (s, 3H); 4.20 (m, 1H); 4.45 (d, 1H, J=16.6 Hz); 5.06 (m, 1H); 6.06 (d, 1H, J=5.4 Hz); 6.88–7.37 (m, 10H); 7.50 (m, 2H); 7.73 (m, 1H); 8.14 (s, 1H). MS(FAB): [M+H]$^+$=511.

Example 21

(S)-2-[3-(1H-Indol-3-ylmethyl)-2,5-dioxo-2,3,4,5-tetrahydro-benzo[e][1,4]diazepin-1-yl]-N-isopropyl-N-(4-methyoxy-phenyl)-acetamide By employing conditions similar to Example 20 except L-tryptophan (554 mg, 2.71 mmol) is substituted for D-tryptophan, the title compound is obtained as a white solid (432 mg, 0.846 mmol). $^1$H NMR (300 MHz, CDCl$_3$): 1.11 (m, 6H); 3.22 (m, 1H); 3.46 (m, 1H); 3.69 (d, 1H, J=16.6 Hz); 3.83 (s, 3H); 4.20 (m, 1H); 4.45 (d, 1H, J=16.6 Hz); 5.06 (m, 1H); 6.06 (d, 1H, J=5.4 Hz); 6.88–7.37 (m, 10H); 7.50 (m, 2H); 7.73 (m, 1H); 8.14 (s, 1H). MS(FAB): [M+H]$^+$=511.

Example 22

S-2-[4-(1H-Indol-3-ylmethyl)-5-oxo-6,5-dihydro-1,2,3a,6-tetraaza-benzo[e]azulene-6-yl}-N-isopyropyl-N-(4-methoxy-phenyl)acetamide According to Process G, (S)-2-[5-chloro-3-(1H-indol-3-ylmethyl)-2-oxo-2,3-dihdihydro-benzo[e][1,4]diazepin-1-yl]-N-isopropyl-N-(4-methoxy-phenyl)-acetamide (167 mg, 0.315 mmol), prepared as in Intermediate 38, is dissolved in toluene (3 mL), formyl hydrazide (50 mg, 0.821 mmol) added and refluxed for 18 hours. The solvent is removed in vacuo and the crude reaction mixture purified by preparative reverse-phase HPLC chromatography with a gradient elution of 25–50% acetonitrile in water with 0.1% trifluoroacetic acid buffer over a 30 minute period with a flow rate of 150 mL/min. Fractions containing the desired material are frozen and lyophilized to provide the title compound (54 mg, 0.101 mmol) as a white lyophilizate. $^1$H NMR (300M Hz, CDCl$_3$): d 1.12 (m, 6H); 2.86 (m, 0.5H); 3.36 (m, 0.5H); 3.60–3.73 (m, 1.5H); 3.79 (s, 3H); 3.93 (m, 0.5H); 4.33–6.48 (m, 1H); 4.80 (m, 0.5H); 5.01 (m, 1H); 5.26 (m 0.5H); 6.55 (m, 0.5H); 6.85–7.71 (m, 10.5H); 7.95 (d, 1H, J=7.4 Hz); 8.08–8.21 (m, 2H); 8.47 (s, 1H). MS(FAB): [M+H]$^+$=535.1

Example 23

(R)-2-[4-(1H-Indol-3-ylmethyl)-5-oxo-6,5-dihydro-1,2,3a,6-tetraaza-benzo[e]azulene6-yl}-N-isopropyl-N-(4-methoxy-phenyl)-acetamide By employing conditions similar to Example 22 except (R)-2-[5-chloro-3-(1H-indol-3-ylmethyl)-2-oxo-2,3-dihydro-benzo[e][1,4]diazepin-1-yl]-N-isopropyl-N-(4-methoxy-phenyl)-acetamide (68 mg, 0.080 mmol), prepared as in Intermediate 39, was substituted for (S)-2-[5-chloro-3-(1H-indol-3-ylmethyl)-2-oxo-2,3-dihydro-benzo[e][1,4]diazepin-1-yl]-N-isopropyl-N-(4-methoxy-phenyl)-acetamide and other reagents scaled accordingly, the title compound (43 mg, 0.080 mmol) is obtained as a white lyophilizate. $^1$H NMR (300 MHz, CDCl$_3$): 1.12 (m, 6H); 2.86 (m, 0.5H); 3.36 (m, 0.5H); 3.60–3.73 (m, 1.5H); 3.79 (s, 3H); 3.93 (m, 0.5H); 4.33–6.48 (m, 1H); 4.80 (m, 0.5H); 5.01 (m, 1H); 5.26 (m 0.5H); 6.55 (m, 0.5H); 6.85–7.71 (m, 10.5H); 7.95 (d,1 H, J=7.4 Hz); 8.08–8.21 (m, 2H); 8.47 (s, 1H). MS(FAB): [M+H]$^+$=535

Example 24

(R)43-(1H-Indol-3-ylmethyl)-1-[isopropyl-(4-methoxy-phenyl)-carbamoylmethyl]-2,5-dioxo-1,2,3 5-tetrahydro-benzo[e][1,4]diazepin-6-yl}-acetic acid To a solution of the TFA salt of (R)-{3-(1H-Indol-3-ylmethyl)-1-[isopropyl-(4-methoxy-phenyl) carbamoylmethyl]-2,5-dioxo-1,2,3,5-tetrahydro-benzo[e][1,4]diazepin-6-yl}-acetic acid tert-butyl ester (84.6 mg, 0.115 mmol), prepared as in Intermediate 40, in DCM (5 mL) is added TFA (3 mL) and stirred 20 minutes at ambient temperature. DCM and TFA are removed in vacuo and the crude product purified by preparative HPLC on a Delta-Pak C-18 column eluted with a linear gradient from 30–60% CH$_3$CN in H$_2$O with 0.1% TFA buffer over a 30 minute period at a rate of 150 mL/min. The appropriate fraction is frozen and lyophilized to give the TFA salt of the title compound (44.3 mg, 0.065 mmol) as a white powder: MS(FAB) m/z=569.4 (MH$^+$); RP-HPLC (Vydac-C18, 30–60% CH$_3$CN in H$_2$O with 0.1% TFA buffer linear gradient, 30 min, 1.5 mL/min) t$_r$=17 min (t$_o$=2.5 min).

Example 25

3-{1-[Isopropyl-(4-methoxy-phenyl)-carbamoylmethyl]-2-oxo-5-phenyl-2,3-dihydro-1H-benzo[e][1,4]diazepin-3-ylmethyl}-1-tert-butoxycarbonyl-indolyl According to Process E, potassium hexamethyldisilylazide (0.5M in toluene, 2.38 mL, 1.189 mmol) is added dropwise to a solution of N-Isopropyl-N-(4-methoxy-phenyl)-2-(2-oxo-5-phenyl-2,3-dihydro-benzo[e][1,4]diazepin-1-yl)-acetamide (0.500 g, 1.133 mmol), prepared as in Intermediate 27, in THF (15 mL) under nitrogen at −5° C. After stirring for 15 min., 3-bromomethyl-indolyl-1-carboxylic acid tert-butyl ester (Liehigs Ann Chem. 1985, 413, 0.386 g, 1.246 mmol) is added in one portion and the mixture is stirred for 30 min. After concentration in vacuo, the reaction mixture is partitioned between ethyl acetate and water. The organic layer is separated, washed with brine, dried over anhydrous magnesium sulfate, filtered, and then concentrated in vacuo to a residue. The crude product is chromatographed on flash grade silica gel using 50% ethyl acetate in n-hexane. Fractions containing the product are combined, concentrated in vacuo to a residue, triturated with n-hexane and then reconcentrated in vacuo to provide the title compound as a white crystalline solid (0.550 g, 0.821 mmol). $^1$H NMR (300 MHz, d6-DMSO) δ=0.91–0.97 (m, 6H); 1.58 (s, 9H); 3.41 (d, 2H, 6.73 Hz); 3.73–3.79 (m, 4H); 4.07–6.21 (m, 2H); 4.67–6.77 (m, 1H); 6.98–7.62 (m, 17 H); 7.69 (d, 1H, J=7.24 Hz); 8.01 (d,1 H, J=8.24). MS (FAB): [M+H]$^+$=670.

Example 26

N-Isopropyl-N-(4-methoxy-phenyl)-2-[4-N-oxide-2-oxo-3-(3-phenyl-ureido)-5-cyclohexyl-2,3-dihydro-benzo[e][1,4]diazepin-1-yl]-acetamide A solution of 2-(3-amino-4-N-oxide-2-oxo-5-cyclohexyl-2,3-dihydro-benzo[e][1,4]diazepin-1-yl)-N-isopropyl-N-(4-methoxy-phenyl)-acetamide (125 mg, 0.261 mmol), prepared as in Intermediate 43, in 3 mL of dichloromethane under a nitrogen atmosphere was treated with phenyl isocyanate (28.4 mg, 0.134 mmol). After stirred at ambient temperature for 30 min., the reaction mixture was diluted with dichloromethane and washed with aqueous potassium carbonated (5% w/v). After separating the layers, the organic phase was dried over anhydrous sodium sulfate, filtered and evaporated in vacuo to a residue. The residue was triturated with diethyl ether and the resulting slurry was stirred for 20 min. The mixture was filtered and washed with diethyl ether. The wet cake was recombined with diethyl ether and sonicated for 20 min., filtered, washed with ether and dried under high vacuum to provide the title compound as a white crystalline solid (80 mg, 0.134 mmol). NMR (300 MHz, CDCl$_3$) δ=8.05 (s, 1H), 7.60 (d, 1H, J=7.9), 7.48 (m, 2H), 7.34 (m, 2H), 7.27 (m, 2H), 7.11 (m, 4H), 6.91 (m, 3H), 6.03 (d, 11H, J=5.9), 4.91 (m, 1H), 4.21 (d, 1H, J=16.4), 4.01 (d, 1H, J=16.4), 3.82 (s, 3H), 3.34 (m, 1H), 2.19 (m, 2H), 1.69 (m, 4H), 1.32 (m, 4H), 1.02 (m, 6H). MS (FAB): [M+H]$^+$=598.2.

What is claimed is:

1. A method of inducing a Cholescystokinin-A receptor agonist response in a mammal in need of treatment of a gastrointestinal or central nervous system related disease which comprises administering to such mammal a therapeutically effective amount of a 1,4-benzodiazepine compound of the following formula (I):

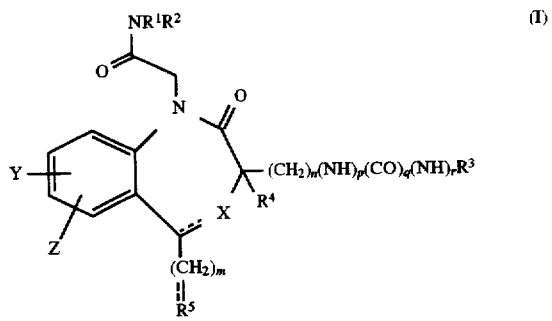

wherein:

R$^1$ is selected from the group consisting of C$_{1-6}$ alkyl, C$_{3-6}$cycloalkyl, phenyl, or phenyl mono-, di-, or trisubstituted independently with hydroxy, C$_{1-6}$alkyl, C$_{1-6}$alkyl substituted with 1–8 fluorine atoms, C$_{1-6}$alkoxy, carboxyC$_{1-6}$alkoxy, halo, amino, mono- or di(C$_{1-6}$alkyl)amino, —COO(C$_{1-6}$alkyl), C$_{1-6}$alkylthio, carboxymethylthio, trifluoromethylsulfonylamino, phenylC$_{1-6}$alkoxy, C$_{1-6}$alkylsulfonyl or C$_{1-6}$alkylsulfinyl substituents;

R$^2$ is selected from the group consisting of C$_{3-6}$ alkyl, C$_{3-6}$cycloalkyl, C$_{3-6}$alkenyl, benzyl, phenylC$_{1-3}$alkyl or phenyl mono-, di-, or trisubstituted independently in the ortho or para positions with hydroxy, C$_{1-6}$alkyl, C$_{1-6}$alkoxy, cyano, benzyloxy, pyrrolidino, morpholino, carboxyC$_{1-6}$alkoxy, halo, amino, mono- or di(C$_{1-6}$alkyl)amino, —COO(C$_{1-6}$alkyl), C$_{1-6}$alkylthio, carboxymethylthio, trifluoromethyl, trifluoromethylsulfonylamino, phenylC$_{1-6}$alkoxy, C$_{1-6}$alkylsulfonyl or C$_{1-6}$alkylsulfinyl substituents; or NR$^1$R$^2$ together form 1,2,3,4-tetrahydroquinoline or benzazepine mono-, di-, or trisubstituted independently with C$_{1-6}$alkyl, C$_{1-6}$alkoxy or halogen substituents;

n is an integer selected from the group consisting of 0, 1, 2, or 3;

p is the integer 0 or 1;

q is the integer 0 or 1;

r is the integer 0 or 1, provided that when q is 0 then r is 0;

R$^3$ is selected from the group consisting of hydrogen, C$_{1-6}$alkyl, C$_{1-6}$cycloalkyl, phenyl, phenyl mono-, di-, or trisubstituted independently with C$_{1-6}$alkyl, hydroxy, C$_{1-6}$alkoxy, halogen, amino, mono- or di(C$_{1-6}$alkyl) amino, nitro, carboxy, —COO(C$_{1-6}$alkyl), carboxy C$_{1-6}$alkoxy, carboxyC$_{1-6}$alkyl, carboxymethylthio, heteroaryl, mono- or di(C$_{1-6}$alkyl)aminoC$_{1-6}$alkyl, trifluoromethyl, trifluoromethoxy, C$_{1-6}$alkylthio, —SO$_v$(C$_{1-6}$alkyl), —SO$_v$NH(C$_{1-6}$alkyl), —SO$_v$CF$_3$, —SO$_v$C$_6$H$_5$, —(CH$_2$)$_v$NO$_2$, —(CH$_2$)$_v$CN, —(CH$_2$)$_v$COOH, —(CH$_2$)$_v$COO(C$_{1-6}$alkyl), —(CH$_2$)$_v$SCH$_3$, —(CH$_2$)$_v$SOCH$_3$, —(CH$_2$)$_v$SO$_2$CH$_3$, —(CH$_2$)$_v$CONH$_2$, —SCH$_2$COOH, —CONH(SO$_2$CH$_3$), —CONH(SO$_2$CF$_3$), —(CH$_2$)$_v$N(C$_{1-6}$alkyl)$_2$, —(CH$_2$)$_v$NH(SO$_2$CF$_3$), —(CH$_2$)$_v$N(SO$_2$CF$_3$)(C$_{1-6}$alkyl), —(CH$_2$)$_v$SO$_2$NHCO (C$_{1-6}$alkyl), —(CH$_2$)$_v$SO$_2$N(C$_{1-6}$alkyl)CO(C$_{1-6}$alkyl), —(CH$_2$)$_z$CONHSO$_2$(C$_{1-6}$alkyl), —(CH$_2$)$_z$CON(C$_{1-6}$alkyl)SO$_2$(C$_{1-6}$alkyl), —(CH$_2$)$_z$NHR$^6$ or —(CH$_2$)$_z$OR$^7$ substituents, heteroaryl, substituted heteroaryl, napthyl, bicycloheteroaryl or substituted bicycloheteroaryl, provided when R$^3$ is oxadiazole then R$^4$ is not hydrogen, further provided when n is 1, p is 0, q is 0 and r is 0 then R$^3$ is not 2-indolyl, substituted 3-indolyl or substituted 1-isoindolyl, still further provided that when n is 0, p is 1, q is 1 and r is 0 then R$^3$ is not 2-indolyl and substituted indolyl is bound at the 2 position, even still further provided that when n is 1, p is 1, q is 1 and r is 0 then R$^3$ is not phenyl or 2-indolyl;

R$^6$ is hydrogen, C$_{1-6}$ alkyl, —SO$_3$H, —SO$_2$CH$_3$, —SO$_2$CF$_3$, —SO$_2$C$_6$H$_5$, —COO(C$_4$H$_9$) or —COO(CH$_2$C$_6$H$_5$);

R$^7$ is hydrogen, C$_{1-6}$alkyl, C$_{3-6}$cycloalkyl, —CH$_2$C$_6$H$_5$, —CH$_2$COOH, —CH$_2$CONH$_2$, —CH$_2$CONH(C$_{1-6}$alkyl), —CH$_2$CON(C$_{1-6}$alkyl)$_2$ or

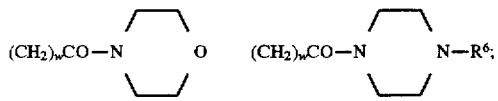

v is an integer selected from the group consisting of 0, 1 or 2;

w is an integer selected from the group consisting of 0, 1 or 2;

R$^4$ is selected from the group consisting of hydrogen, C$_{1-6}$alkyl, halogen, C$_{1-6}$alkoxy, C$_{1-6}$alkoxyC$_{1-3}$alkyl, carboxyC$_{1-3}$alkyl or C$_{1-6}$alkoxycarbonylC$_{1-3}$alkyl;

X is nitrogen, nitroso, or NR8, provided that when X is nitrogen or nitroso then ———— is a double bond between X and the C-5 position of the diazepine ring, and is a single bond when X is NR$^8$;

R$^8$ is selected from the group consisting of hydrogen, C$_{1-6}$alkyl or (CH$_2$)$_k$R$^9$;

k is an integer selected from the group consisting of 0, 1, 2, 3 or 4;

R$^9$ is selected from the group consisting of amino, mono- or di(C$_{1-6}$alkyl)amino, pyrrolidinyl, morpholinyl, piperidinyl, piperazinyl, phenyl, nitro, carboxyl, carboxamide, hydroxyl, heteroaryl, —COO(C$_{1-6}$alkyl), —CONH(C$_{1-6}$alkyl), —SO$_t$(C$_{1-6}$alkyl), —SO$_t$NH(C$_{1-6}$alkyl), —SO$_t$CF$_3$, —SO$_t$C$_6$H$_5$, —O(C$_{1-6}$alkyl) or —CON(C$_{1-6}$alkyl)$_2$;

t is an integer selected from the group consisting of 0, 1 or 2;

m is an integer selected from the group consisting of 0, 1, 2, or 3,

R$^5$ is selected from the group consisting of hydrogen, C$_1$–C$_6$ alkyl, C$_3$–C$_7$ cycloalkyl, oxygen, phenyl, phenyl mono or di-substituted with halogen substituents, heteroaryl, substituted heteroaryl or 5, 6 or 7 membered saturated heterocycle, provided that when R$^5$ is oxygen and m is 0 then ———— is a double bond between R$^5$ and the C-5 position of the diazepine ring, and is a single bond when R$^5$ is not oxygen; or XR$^5$ together form a heteroaryl or substituted hetearyl where X is nitrogen, provided ———— is a double bond between R5 and the C-5 position of the diazepine ring and m is 0;

Y and Z are independently hydrogen or halogen;

5, 6 or 7 membered saturated heterocycle in more detail is a 5, 6 or 7 membered saturated heterocycle interrupted by 1, 2, 3, or 4 N or O heteroatoms, with the proviso that any two O atoms are not bonded to each other;

heteroaryl in more detail includes a 5 or 6 membered aromatic ring optionally interrupted by 1, 2, 3 or 4 N, S, or O heteroatoms, with the proviso that any two O or S atoms are not bonded to each other;

substituted heteroaryl in more detail includes heteroaryl mono-, di-, or trisubstituted independently with hydroxy, C$_{1-6}$alkyl, C$_{1-6}$alkoxy, carboxyC$_{1-6}$alkoxy, halogen, amino, mono- or di(C$_{1-6}$alkyl)amino, nitro, carboxy, —COO(C$_{1-6}$alkyl), —CONH(C$_{1-6}$alkyl), C$_{1-6}$alkylthio, carbosamide, carboxymethylthio, phenyl, benzyl, benzoxy, cyano, trifluoromethyl, —CONH(C$_{1-6}$alkyl), —CONHC$_{1-6}$alkyl)$_2$, —SO$_z$(C$_{1-6}$alkyl), —SO$_z$NH(C$_{1-6}$alkyl), —SO$_z$CF$_3$ or —SO$_z$C$_6$H$_5$, pyrrolidinyl, morpholinyl, piperidinyl, piperazinyl, trifluoromethylsulfonylamino, phenyl C$_{1-6}$alkoxy, C$_{1-6}$alkylsulfonyl, C$_{1-6}$alkylsulfinyl, phenyl, carboxamide, or heteroaryl substituents;

z is an integer selected from the group consisting of 0, 1 or 2;

bicycloheteroaryl in more detail is a 9 or 10 membered bicyclo aromatic ring interrupted by 1, 2, 3 or 4 N, O or S heteroatoms, with the proviso that any two O or S heteroatoms are not bonded to each other, with the further proviso that bicycloheteroaryl is not quinoline;

substituted bicycloheteroaryl in more detail includes bicyclo heteroaryl mono-, di-, or trisubstituted independently with hydroxy, (C$_{1-6}$alkyl), C$_{1-6}$alkoxy, cyano, carboxy(C$_{1-6}$alkyl), phenyl, heteroaryl, phenyl(C$_{1-6}$alkyl) or (C$_{1-6}$alkyl)COO(C$_{1-6}$alkyl);

or a pharmaceutically acceptable acid-addition or organic base-addition salt thereof.

2. The method of claim 1, further comprising a 1,4-benzodiazepine compound of the following formula (Ia):

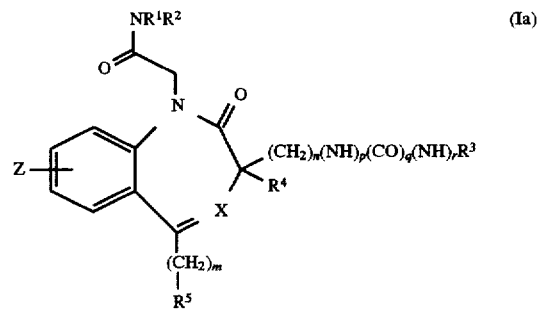

wherein:

R$^1$ is selected from the group consisting of C$_1$–C$_6$ alkyl, C$_3$–C$_6$cycloalkyl, phenyl, or phenyl mono-, di-, or trisubstituted independently with hydroxy, C$_{1-6}$alkyl, C$_{1-6}$alkyl substituted with 1–8 fluorine atoms, C$_{1-6}$alkoxy, carboxyC$_{1-6}$alkoxy, fluoro, amino, mono- or di(C$_{1-6}$alkyl)amino, —COO(C$_{1-6}$alkyl), C$_{1-6}$alkylthio, carboxymethylthio, trifluoromethyl, trifluoromethylsulfonylamino, phenylC$_{1-6}$alkoxy, C$_{1-6}$alkylsulfonyl or C$_{1-6}$alkylsulfinyl substituents;

R$^2$ is selected from the group consisting of C$_3$–C$_6$ alkyl, C$_3$–C$_6$cycloalkyl, C$_3$–C$_6$alkenyl, benzyl, phenylC$_1$–C$_3$alkyl or phenyl mono-, di-, or trisubstituted independently in the ortho or para positions with hydroxy, C$_{1-6}$alkyl, C$_{1-6}$alkoxy, cyano, benzyloxy, pyrrolidino, morpholino, carboxyC$_{1-6}$alkoxy, chloro, amino, mono- or di(C$_{1-6}$alkyl)amino, —COO(C$_{1-}$ 6alkyl), $C_{1-6}$alkylthio, carboxymethylthio, trifluoromethyl, trifluoromethylsulfonylamino, phenyl$C_{1-6}$alkoxy, $C_{1-6}$alkylsulfonyl or $C_{1-6}$alkylsulfinyl substituents; or $NR^1R^2$ together form 1,2,3,4-tetrahydroquinoline or benzazepine mono-, di-, or trisubstituted independently with $C_{1-6}$alkyl, $C_{1-6}$alkoxy or halogen substituents;

n is an integer selected from the group consisting of 0, 1, 2, or 3;

p is the integer 0 or 1;

q is the integer 0 or 1;

r is the integer 0 or 1, provided that when q is 0 then r is 0;

$R^3$ is selected from the group consisting of hydrogen, $C_{1-6}$alkyl, $C_{1-6}$cycloalkyl, phenyl, phenyl mono-, di-, or trisubstituted independently with $C_{1-6}$alkyl, hydroxy, $C_{1-6}$alkoxy, halogen, amino, mono- or di($C_{1-6}$alkyl)amino, nitro, carboxy, —COO($C_{1-6}$alkyl), carboxy$C_{1-6}$alkoxy, carboxy$C_{1-6}$alkyl, carboxymethylthio, heteroaryl, mono- or di($C_{1-6}$alkyl)aminoalkyl, or trifluoromethyl, trifluoromethoxy, $C_{1-6}$alkylthio, —$SO_v$($C_{1-6}$alkyl), —$SO_v$NH($C_{1-6}$alkyl), —$SO_vCF_3$ or —$SO_vC_6H_5$, —$(CH_2)_vNO_2$, —$(CH_2)_vCN$, —$(CH_2)_vCOOH$, —$(CH_2)_vCOO(C_{1-6}$alkyl), —$(CH_2)_vSCH_3$, —$(CH_2)_vSOCH_3$, —$(CH_2)_vSO_2CH_3$, —$(CH_2)_vCONH_2$, —$SCH_2COOH$, —$CONH(SO_2CH_3)$, —$CONH(SO_2CF_3)$, —$(CH_2)_vN(C_{1-6}$alkyl)$_2$, —$(CH_2)_vNH(SO_2CF_3)$, —$(CH_2)_vN(SO_2CF_3)(C_{1-6}$alkyl), —$(CH_2)_vSO_2NHCO(C_{1-6}$alkyl), —$(CH_2)_vSO_2N(C_{1-6}$alkyl)CO($C_{1-6}$alkyl), —$(CH_2)_vCONHSO_2(C_{1-6}$alkyl), —$(CH_2)_vCON(C_{1-6}$alkyl)$SO_2(C_{1-6}$alkyl), —$(CH_2)_vNHR^6$ or —$(CH_2)_vOR^7$ substituents, heteroaryl, heteroaryl substituted with halogen, $C_{1-6}$alkyl, hydroxy, nitro, cyano, carboxy, $C_{1-6}$alkoxy, benzoxy, —COO($C_{1-6}$alkyl), amino, mono- or di($C_{1-6}$alkyl)amino, phenyl or benzyl substituents, napthyl, bicycloheteroaryl or bicycloheteroaryl N-substituted independently with hydroxy, carboxyalkyl, phenyl, heteroaryl, $C_{1-6}$alkoxy or cyano substituents;

$R^6$ is hydrogen, $C_{1-6}$ alkyl, —$SO_3H$, —$SO_2CH_3$, —$SO_2CF_3$, —$SO_2C_6H_5$, —$COO(C_4H_9)$ or —$COO(CH_2C_6H_5)$;

$R^7$ is hydrogen, $C_{1-6}$alkyl, $C_{3-6}$cycloalkyl, —$CH_2C_6H_5$, —$CH_2COOH$, —$CH_2CONH_2$, —$CH_2CONH(C_{1-6}$alkyl), —$CH_2CON(C_{1-6}$alkyl)$_2$ or

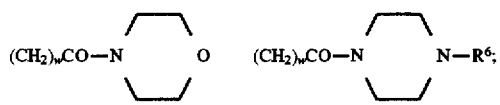

v is an integer selected from the group consisting of 0, 1 or 2;

w is an integer selected from the group consisting of 0, 1 or 2;

$R^4$ is selected from the group consisting of hydrogen, halogen, $C_{1-6}$alkyl, $C_{1-6}$alkoxy, $C_{1-6}$alkoxy$C_{1-3}$alkyl, carboxy$C_{1-3}$alkyl or $C_{1-6}$alkoxycarbonyl$C_{1-3}$alkyl;

X is nitrogen or nitroso, provided that when $R^2$ is methoxyphenyl, p is 1, q is 1 and r is 0 then X is nitroso;

m is an integer selected from the group consisting of 0, 1, 2, or 3;

$R^5$ is selected from the group consisting of hydrogen, $C_1-C_6$ alkyl, $C_{5-7}$cycloalkyl, phenyl or phenyl mono- or di-ortho-substituted independently with halogen substituents, or a heteroaryl selected from the group consisting of pyridyl, pyrimidinyl, pyridazinyl, pyrazinyl, furanyl, thiophenyl, pyrrolyl, oxazolyl, thiazolyl, imidazolyl, pyrazolyl, isoxazolyl, isothiazolyl, oxadiazolyl, thiazolyl, thiadiazolyl, pyrrolidinyl, piperidinyl, morpholinyl or thiomorpholinyl, where such heteroaryl may be mono- or di-ortho-substituted independently with halogen, $C_{1-6}$alkyl, nitro, carboxyl, $C_{1-6}$alkoxycarbonyl, $C_{1-6}$alkoxy, $C_{1-6}$alkylthio, amino or mono- or di($C_{1-6}$alkyl)amino substituents;

Z is hydrogen or halogen;

heteroaryl in more detail includes a 5 or 6 membered aromatic ring optionally interrupted by 1, 2, 3 or 4 N, S, or O heteroatoms, with the proviso that any two O or S atoms are not bonded to each other;

substituted heteroaryl in more detail includes heteroaryl mono-, di-, or trisubstituted independently with $C_{1-6}$alkyl or phenyl;

or a pharmaceutically acceptable acid-addition or base-addition salt thereof.

3. The method as claimed in claim 1 wherein $R^1$ is $C_{3-6}$ alkyl or $C_{3-6}$ cycloalkyl and $R^2$ is phenyl or phenyl substituted at the 4 position by methyl, methoxy, trifluoromethyl, trifluoromethoxy, dimethylamino, fluoro, pyrrolidino or morpholino.

4. The method as claimed in claim 1 when $R^1$ is isopropyl and $R^2$ is phenyl or 4-methoxyphenyl.

5. The method as claimed in claim 1 wherein $R^4$ is hydrogen.

6. The method as claimed in claim 1 when Z is hydrogen.

7. The method as claimed in claim 1 wherein n is 1, p, q and r are zero and $R^3$ is 3-indolyl.

8. The method as claimed in claim 1 wherein n is zero, p, q and r are 1 and $R^3$ is optionally substituted phenyl or 7-indazolyl.

9. The method as claimed in claim 1 wherein n is zero, p and q are 1, r is zero and $R^3$ is indolyl substituted on the nitrogen atom therein by carboxymethyl.

10. The method as claimed in claim 2 wherein m is zero and $R^5$ is a group selected from phenyl, methyl, pyridyl or cyclohexyl.

11. A method as described in claim 1 comprising the administration of the compounds of claim 1 in admixture with one or more physiologically acceptable carriers or excipients.

12. A compound of formula (Ia) as defined in claim 2, wherein $R^1$ is isopropyl and $R^2$ is phenyl or 4-methoxyphenyl.

* * * * *